(12) United States Patent
Ishihara et al.

(10) Patent No.: US 8,252,814 B2
(45) Date of Patent: Aug. 28, 2012

(54) AGENTS AND CRYSTALS FOR IMPROVING EXCRETORY POTENCY OF URINARY BLADDER

(75) Inventors: Yuji Ishihara, Itami (JP); Takayuki Doi, Izumi (JP); Hiroshi Nagabukuro, Osaka (JP); Yuji Ishichi, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 984 days.

(21) Appl. No.: 12/219,198

(22) Filed: Jul. 17, 2008

(65) Prior Publication Data
US 2009/0264467 A1 Oct. 22, 2009

Related U.S. Application Data

(60) Division of application No. 11/475,881, filed on Jun. 28, 2006, now abandoned, which is a continuation of application No. 09/960,477, filed on Sep. 24, 2001, now abandoned, which is a continuation-in-part of application No. 09/787,288, filed as application No. PCT/JP99/05367 on Sep. 30, 1999, now abandoned.

(30) Foreign Application Priority Data

Sep. 30, 1998 (JP) .................................. 10-276677
Mar. 23, 2001 (JP) .................................. 2001-85190

(51) Int. Cl.
*A01N 43/40* (2006.01)
*A61K 31/445* (2006.01)
(52) U.S. Cl. ...................... 514/319; 546/206
(58) Field of Classification Search .................. 514/319; 546/206
See application file for complete search history.

(56) References Cited

U.S. PATENT DOCUMENTS

| | | | |
|---|---|---|---|
| 4,472,320 A | 9/1984 | Ashani et al. | |
| 5,155,226 A | 10/1992 | Lee et al. | |
| 5,177,082 A | 1/1993 | Yu | |
| 5,527,800 A | 6/1996 | Goto et al. | |
| 5,686,466 A | 11/1997 | Goto et al. | |
| 5,864,039 A | 1/1999 | Kawakita et al. | |

FOREIGN PATENT DOCUMENTS

| | | |
|---|---|---|
| EP | 296560 | 12/1988 |
| EP | 500006 | 8/1992 |
| EP | 607864 | 7/1994 |
| JP | 4-21670 | 1/1992 |
| JP | 6-507617 | 9/1994 |
| JP | 8-245582 | 9/1996 |
| JP | 8-245583 | 9/1996 |
| JP | 08245582 | 9/1996 |
| JP | 08245583 | 9/1996 |
| JP | 9-20755 | 1/1997 |
| WO | 92/20327 | 11/1992 |
| WO | 94/27965 | 12/1994 |

OTHER PUBLICATIONS

S.L. Rogers et al., Dementia 7, 293-303 (1996).*
K. Maslow, Alzheimer's & Dementia, 4, 110-133, (2008).*
Sakakibara et al, Neurourology and Urodynamics, 34, 273-275, 273 (2005).*
N.M. Resnick et al., Journal of the American Medical Association 257(22), 3076-3081, 3076 (1987).*
T. Sugiyama et al., International Journal of Urology, 1, 337-340 (1994).*
J.W. Thuroff et al., World Journal of Urology 16, S1 S48-S61 (1998).*
European Search Report issued Dec. 16, 2008 in European Patent Application No. 07023437.2.
Ono, H. et al., "General Pharmacological Studies on Donepezil Hydrochloride", *Jpn. Pharmacol. Ther.*, (1998), 26: S1321-1338.
Hemingway-Eltomey, J. M. et al., "Adverse Effects of Donepezil in Treating Alzheimer's Disease Associated with Down's Syndrome", *Am. J. Psychiatry*, (1999), 156:9.
T. Yamanishi, et al., "Combination of a cholinergic drug and an α-blocker is more effective than monotherapy for the treatment of voiding difficulty in patients with underactive detrusor", *International Journal of Urology*, vol. 11, 2004, pp. 88-96.
T. Katsumi et ano., "Clinical Effects of Distigmine Bromide (UBRETID®), A Cholinesterase Inhibitor, on Micturition Disturbance by Benign Prostatic Hypertrophy", *Acta Urol. Jpn.*, vol. 38, 1992, pp. 1089-1092, Abstract only.
S.S. Hegde et al., "RS 39604: A Potent, Selective and Orally Active 5-$HT_4$ Receptor Antagonist", *British Journal of Pharmacology*, vol. 115, pp. 1087-1095, 1995.
Tobin et al., "In vivo an in vitro effect of muscarinic receptor antagonists . . . ", *Eur. J. Pharm.*, vol. 281, pp. 1-8, 1995.
Lai et al., "Characterization of Muscarinic Receptors . . . ", *Life Science*, vol. 62, No. 13, pp. 1179-1186, 1998.
Hisayama et al., "Mechanism of action of nicotine . . . ", Medline Abstract, PubMed ID #3228673, 1989 (*Br. J. Pharm.*, vol. 95, No. 2, pp. 465-472, 1989.

* cited by examiner

*Primary Examiner* — James O Wilson
*Assistant Examiner* — Alexander R Pagano
(74) *Attorney, Agent, or Firm* — Wenderoth, Lind & Ponack, L.L.P.

(57) ABSTRACT

Agents for improving potency of the urinary bladder which comprise an amine compound of non-carbamate-type having an acetylcholinesterase-inhibiting action. Particularly, crystals of a tricyclic, condensed, heterocyclic derivative are provided, which possess an excellent action to inhibit acetylcholinesterase and an action to improve the excretory potency of the urinary bladder. As an example, crystals of 8-[3-[1-[(3-fluorophenyl)-methyl]-4-piperidinyl]-1-oxopropyl]-1,2,5,6-tetrahydro-4H-pyrrolo[3,2,1-ij]quinolin-4-one or a salt thereof and pharmaceutical compositions containing them are disclosed.

3 Claims, 1 Drawing Sheet

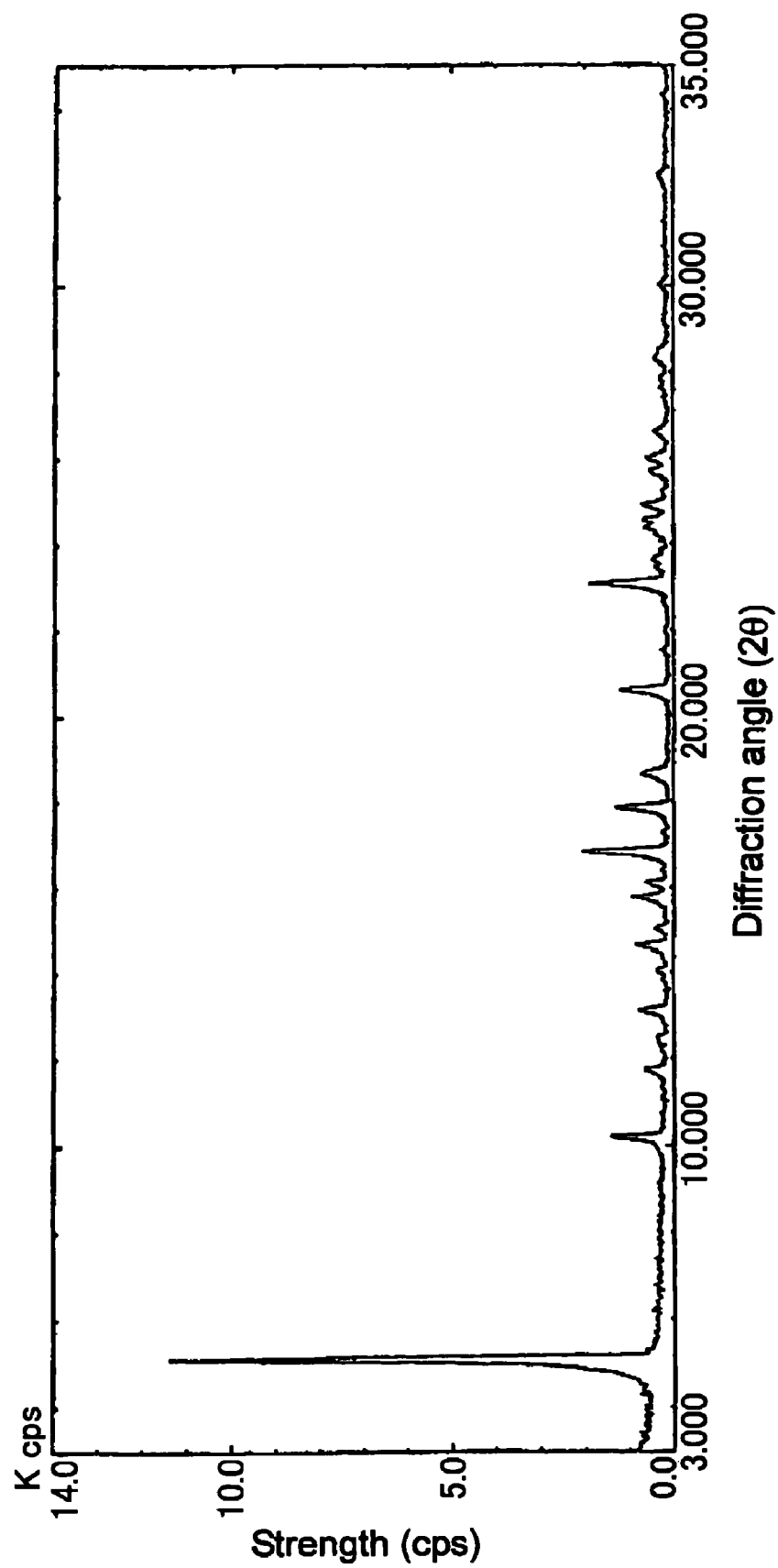

AGENTS AND CRYSTALS FOR IMPROVING EXCRETORY POTENCY OF URINARY BLADDER

This application is a divisional of U.S. Ser. No. 11/475,881, filed Jun. 28, 2006, now abandoned, which is a continuation of U.S. Ser. No. 09/960,477, filed Sep. 24, 2001, now abandoned, which is a continuation-in-part of U.S. Ser. No. 09/787,288, filed Mar. 15, 2001, now abandoned, which is the National Stage of PCT/JP99/05367 filed Sep. 30, 1999.

BACKGROUND OF THE INVENTION

1. Field of the Invention

The present invention relates to drugs, particularly agents for further improving excretory potency of the urinary bladder. The present invention further to relates to crystals and pharmaceutical compositions comprising the crystals of a tricyclic, condensed, heterocyclic compound which inhibit acetylcholinesterase and improve excretory potency of the urinary bladder.

2. Description of Related Art

Inferior uropathy is a general term for subjective or objective disorders in a process through accumulation of urine (urinary storage) till excretion (urination), which may be classified into urinary cumulative disorders (incontinence of urine, pollakiuria, etc.), dysuria (difficulty of urination, scalding, obstruction of urinary tract, etc.), and the like. Inferior uropathy in the aged, particularly dysuria, especially dysuria caused by prostatomegaly, becomes a great problem of public concern with the advance of a recent aging society, though inferior uropathy may also be found in the youth.

Urination is, under the control of the urination center, controlled by the peripheral nervous system involving a parasympathetic nerve such as the pelvic nerve, the sympathetic nerve such as the hypogastric nerve, and the somatic nerve such as the pudendal nerve, and it is suggested that a variety of neurotransmitters (e.g., acetylcholine, adrenaline, ATP, Substance P, neuropeptide Y, etc.) are involved in urination.

As agents for treatment of dysuria, particularly difficulty of urination, those for increasing contraction of the muscles of the urinary bladder (detrusor) or relaxing sphincter muscle of the urethra to reduce urethral resistance have been used. As the agents acting on the muscle of the urinary bladder to increase the contraction, for example, cholinergic agents such as bethanechol, acetylcholinesterase inhibitors such as distigmine, and the like have been used. Bethanechol however is incompatible with pregnant women, peptic ulcers, organic ileus, asthma, hyperthyroidism, etc., because it has adverse effects such as epiphora, sweating, gastro-intestinal disorders, stomachache, etc. No entirely satisfactory drugs have yet been found.

As the acetylcholinesterase inhibitors increasing contraction of the muscle of the urinary bladder, carbamate-type acetylcholinesterase inhibitors having a carbamate structure (—OCON—) in its molecule (e.g., distigmine, neostigmine, etc.) are known. These carbamate-type acetylcholinesterase inhibitors are known to express their inhibitory effect based on the carbamate structure which is characteristic of the molecule (Goodman & Gilman's The PHARMACOLOGICAL BASIS OF THERAPEUTICS, Ninth ed., McGraw-Hill, New York, p. 161-176). However, it is known that, for example, distigmine is insufficient in its clinical efficacy since it contracts the muscle of the urinary bladder with constriction of the muscle of the urethra to increase urethral resistance and consequently make the voiding flow rate worse. In addition, neostigmine has not been used in therapy because of the short duration of its action (Takamichi Hattori and Kosaku Yasuda, "Sinkeiinseiboukou-No-Sindan-To-Chiryou (Diagnosis and Therapy of Neurogenic Bladder)", 2nd Ed., p. 105-106, p. 139, Igaku-Shoin Ltd. Tokyo).

On the other hand, a variety of amine compounds which have an acetylcholinesterase inhibiting effect and are different from carbamate-type inhibitors in their structure have been reported as follows.

(1) Compounds of the following formula:

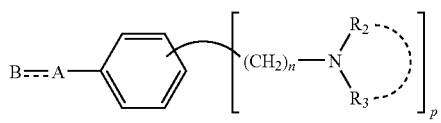

wherein B represents an optionally substituted saturated or unsaturated 5- to 7-membered aza-heterocyclic group; A is a bond or alkylene or alkenylene optionally substituted with hydrocarbon residue, oxo or hydroxy; ═ indicates a single bond or double bond (where when A is a bond, ═ indicates a single bond); $R_2$ and $R_3$ each represent independently hydrogen or optionally substituted hydrocarbon residue (but they are not hydrogen concurrently) or they may be taken with the adjacent nitrogen atom to form a cyclic amino group; n is 0, 1 or 2; and p is 1 or 2;
or salts thereof as described in EP-A-0 378 207.

Such compounds as described are exemplified by 3-[1-(phenylmethyl)piperidin-4-yl]-1-[4-(pyrrolidin-1-yl)phenyl]-1-propanone, 1-[4-(N,N-dimethylamino)phenyl]-3-[1-(phenylmethyl)piperidin-4-yl]-1-propanone, and the like.

(2) Compounds of the following formula:

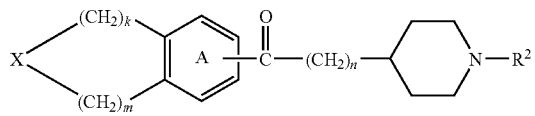

wherein X represents $R^1$—N< ($R^1$ is hydrogen, optionally substituted hydrocarbon group or optionally substituted acyl), oxygen or sulfur; $R^2$ represents hydrogen or optionally substituted hydrocarbon group; the ring A represents an optionally substituted benzene ring; k is an integer of 0-3; m indicates an is of 1-8; and n is an integer of 1-6;
or salts thereof as described in Japanese Patent Unexamined Publication No. (hereinafter referred to as JP-A) 5-140149/1993.

Such compounds as described above are exemplified by 3-[1-(phenylmethyl)piperidin-4-yl]-1-(2,3-dihydro-1H-indol-5-yl)-1-propanone, 3-[1-(phenylmethyl)piperidin-4-yl]-1-(2,3,4,5-tetrahydro-1H-1-benzazepin-8-yl)-1-propanone, and the like.

(3) Compounds of the following formula:

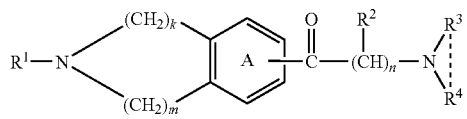

wherein $R^1$ represents hydrogen, optionally substituted hydrocarbon group or optionally substituted acyl; the ring A represents an optionally further substituted benzene ring; n is an integer of 1 to 10; $R^2$, $R^3$ and $R^4$ are the same or different representing hydrogen or optionally substituted hydrocarbon group, or $R^3$ and $R^4$ may be taken with the adjacent nitrogen atom to form an optionally substituted heterocyclic group, and $R^2$ may be different respectively according to repetition of n; k is an integer of 0 to 3; m is an integer of 1 to 8; provided that when k=0 and m=2, then n>1;
or salts thereof as described in JP-A 6-166676/1994.

Such compounds as described above are exemplified by 3-[1-(phenylmethyl)-2,3,4,5-tetrahydro-1H-3-benzazepin-7-yl]-3-[4-(phenylmethyl)piperazin-1-yl]-1-propanone, 1-[2-(phenylmethyl)-2,3,4,5-tetrahydro-1H-2-benzazepin-8-yl]-3-[4-(phenylmethyl)piperazin-1-yl]-1-propanone, and the like.

(4) Compounds of the following formula:

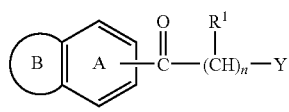

wherein the ring A represents an optionally further substituted benzene ring; the ring B represents an optionally substituted non-aromatic heterocyclic ring containing the same or different, two or more hetero atoms; $R^1$ represents hydrogen or optionally substituted to hydrocarbon group, which may be different according to a repetition of n; Y represents an optionally substituted amino or an optionally substituted nitrogen-containing saturated heterocycle; and n is an integer of 1 to 10; or salts thereof as described in JP-A 6-206875/1994.

Such compounds as described above are exemplified by 3-[1-(phenylmethyl)piperidin-4-yl]-1-(2,3,4,5-tetrahydro-1,4-benzoxazepin-7-yl]-1-propanone and the like.

(5) JP-A 7-206854/1995 discloses the formula:

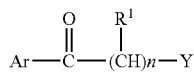

wherein Ar represents an optionally substituted tricyclic condensed benzene ring group condensed with at least one heterocycle; n is an integer of 2 to 10; $R^1$ represents hydrogen or optionally substituted hydrocarbon group, which may be different according to a repetition of n; Y represents 4-piperidinyl, 1-piperadinyl or 4-benzyl-1-piperidinyl, each of which may have a substituent or substituents.

Such compounds as described above are exemplified by 8-[3-[1-(phenylmethyl)-4-piperidinyl]-1-oxopropyl]-1,2,5, 6-tetrahydro-4H-pyrrolo[3,2,1-ij]quinolin-4-one, 1-(1,2,2a, 3,4,5-hexahydrobenz[cd]indol-6-yl)-3-[1-(phenylmethyl)-4-piperidinyl]-1-propanone, and the like.

Also described in the Japanese Patent Kokai Publication is an amorphous substance of 8-[3-[1-[(3-fluorophenyl)methyl]-4-piperidinyl]-1-oxopropyl]-1,2,5,6-tetrahydro-4H-pyrrolo[3,2,1-ij]quinolin-4-one or a salt thereof, which possesses an action to inhibit acetylcholine esterase.

(6) Compounds of the following formula:

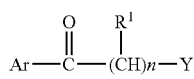

wherein Ar represents an optionally substituted tetracyclic condensed heterocyclic group; n is an integer of 1 to 10; $R^1$ represents hydrogen or optionally substituted hydrocarbon group, which may be different according to a repetition of n; Y represents an amino or nitrogen-containing saturated heterocyclic group, each of which may have a substituent or substituents; or salts thereof as described in JP-A 7-309835/1995.

Such compounds as described above are exemplified by 3-[3-[1-(phenylmethyl)-4-piperidinyl]-1-oxopropyl]-7,11b, 12,13-tetrahydro-5H-isoindolo[2,1-b][2]benzazepin-7-one, 2-[1-oxo-3-[1-(phenyl methyl)-4-piperidinyl]-4,5,7a,8,9,10, 11,11a-octahydro-6H-pyrido[3,2,1-jk]carbazol-6-one, and the like.

(7) Amine compounds described in WO 93/07140, PCT Japanese Patent Unexamined Publication No. (hereinafter referred to as PCT JP-A) 6-500794/1994, JP-A 4-234845/1992, JP-A 6-116237/1994, JP-A 7-109275/1995, WO 97/37992, JP-A 5-148228/1993, JP-A 5-194359/1993, JP-A 6-507387/1994, PCT JP-A 7-502272/1995, PCT JP-A 8-511515/1996, JP-A 6-41070/1994, JP-A 5-9188/1993, JP-A 5-279355/1993, JP-A 5-320160/1993, JP-A 6-41125/1994, JP-A 5-345772/1993, JP-A 7-502529/1995, JP-A 64-79151/1989, JP-A 62-234065/1987, JP-A 4-235161/1992, JP-A 4-21670/1992, JP-A 9-268176/1997, and so on.

(8) Amine compounds described in JP-A 2-167267/1990, JP-A 63-166881/1988, JP-A 2-96580/1990, JP-A 3-153667/1991, JP-A 61-148154/1986, Japanese Patent Examined Patent No. (hereinafter referred to as JP-B) 5-41141/1993, JP-A 63-284175/1988, JP-A 3-95161/1991, JP-A 3-220189/1991, JP-A 4-134083/1992, JP-A 4-66571/1992, PCT JP-A 11-500144/1999, PCT JP-A 10-511651/1998, JP-A 4-290872/1992, JP-A 2-231421/1990, JP-A 4-18071/1992, JP-A 4-159225/1992, JP-A 4-346975/1992, WO 99/11625, J. Am. Chem. Soc., 1991, 113, p. 4695-4696, J. Am. Chem. Soc., 1989, 111, p. 4116-4117, WO 97/11077, Heterocycles, 1977, 8, p. 277-282, J. Chem. Soc. (C), 1971, p. 1043-1047, and so on.

(9) Amine compounds described in fP-A 2-91052/1990, JP-A 3-95143/1991, JP-A 3-141244/1991, JP-A 3-223251/1991, JP-A 5-239024/1993, JP-A 2-138255/1990, and so on.

Moreover, amine compounds having various pharmacological actions have been reported as follows.

(1) WO 91/03243 describes compounds of the following formula:

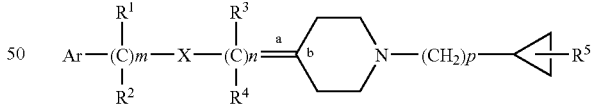

wherein m is 0 to 3, n is 0 to 3, and m and n are not 0 at the same time; p is 0 to 3; X is O, S, SO, $SO_2$, $NR^6$, $CR^7R^8CO$ or CHOH; $R^1$, $R^3$ and $R^7$ each represent hydrogen, $C_{1-5}$ alkyl, halogen, $NR^{10}R^{11}$, OR, COOH, $C_{2-6}$ carbalkoxy, CN, Ar, $C_{1-5}$ alkoxy or $C_{1-5}$ alkylthio; $R^2$, $R^4$ and $R^8$ each represent hydrogen, $C_{1-5}$ alkyl, $C_{2-6}$ carbalkoxy, CN, $C_{1-5}$ alkoxy or $Ar^1$; when X is O, S, SO, $SO_2$ or $NR^6$, then $R^1$, $R^2$, $R^3$ and $R^4$ are not $C_{1-5}$ alkoxy, $C_{1-5}$ alkylthio, $NR^{10}R^{11}$ or OH; $R^5$ represents hydrogen, alkyl, halogen, OH or alkenyl; $R^6$ represents hydrogen, $C_{1-5}$ alkyl or $Ar^1$; Ar and $Ar^1$ each represent naphthyl, pyridyl, pyrimidyl, indolyl, quinolinyl, isoquinolinyl or phenyl, and these groups may be substituted by $C_{1-3}$ alkyl, $C_{1-3}$ alkoxy, $C_{1-3}$ haloalkyl containing 1 to 7 halogen atoms, SH, $S(O)t-C_{1-3}$ alkyl (t is 1, 2 or 3), $C_{2-6}$ dialkylamino, halogen, $C_{1-3}$ alkylamino, $NH_2$, CN, $NO_2$, $SO_3H$, tetrazole, COOH, $C_{2-6}$ carboalkoxy, $CONH_2$, $SO_2$, $NO_2$, $COR^9$, $CONR^{12}R^{13}$, $SO_2NR^{12}R^{13}$, $Ar^2$, $OAr^2$ or $SAr^2$; $Ar^2$ is naphthyl or phenyl, and these groups may be substituted by $C_{1-3}$ alkyl, $C_{1-3}$ haloalkyl containing 1 to 7 halogen atoms, $C_{1-3}$ alkoxy, halogen or $C_{1-3}$ alkylthio; $R^9$, $R^{10}$, $R^{11}$, $R^{12}$ and $R^{13}$ each represent hydrogen, $C_{1-5}$ alkyl or phenyl, $R^{10}$ and $R^{11}$ together may form a $C_{3-6}$ alkylene chain, $R^{12}$ and $R^{13}$ together may form a $C_{3-6}$ alkylene chain; a or b indicates a double bond or single bond, but they are not double bonded at the same time;

or pharmacologically acceptable salts thereof which can be used as antipsychotics.

(2) JP-A 52-72829/1977 describes compounds of the following formula:

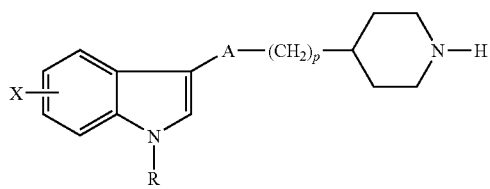

wherein R is hydrogen, alkyl containing 1 to 4 carbon atoms, or aralkyl of which the alkyl portion contains 1 or 2 carbon atoms; X is hydrogen or halogen, alkyl, alkoxy or alkylthio, each of which may contain 1 to 4 carbon atoms, trifluoromethyl, nitro, hydroxy or unsubstituted amino, or amino substituted by 1 or 2 alkyl groups or acyl or alkylsulfonyl; A is a group —CO— or —$CH_2$—; and n is 0, 1 or 2;

or salts thereof which can be used in treatment of diseases caused particularly by serotonergic dysfunction.

In these compounds, however, there is neither report, suggestion nor disclosure on their effect as prophylactics or therapeutic agents for dysuria (difficulty of urination) or on their effect as excretion improving agents for urinary bladder.

Therefore, it has been a desire to develop prophylactics or therapeutic agents for dysuria, particularly difficulty in urination, which have a high efficiency for urination and high versatility compared with known compounds known to have an effect in improving excretion of the urinary bladder.

There has also been a desire in the pharmaceutical industry to attain crystals that are good in absorbability and are used for an acetylcholine esterase inhibitor, an agent for improving the excretory potency of a urinary bladder, and a therapeutic agent against micturition disorders/dysuria disorders which are stable.

SUMMARY OF THE INVENTION

In view of such current realities, the present inventors searched for highly effective new agents for improving excretion of the urinary bladder with high efficiency of urination, that is, therapeutic agents for dysuria, particularly for difficulty in urination. As a result of diligent investigation, they have discovered that acetylcholinesterase-inhibiting amine compounds of the non-carbamate-type show an unexpectedly high effect in improving excretion of the urinary bladder as well as a prophylactic or therapeutic effect for dysuria, particularly, for difficulty in urination with an unexpectedly high effect of increasing the contraction potency of the muscle of the urinary bladder but with no effect of contracting the muscle of the urethra. The first aspect of the invention was completed based on these findings. That is, the present invention relates to:

(1) An agent for improving the excretory potency of the urinary bladder which comprises an amine compound of the non-carbamate-type having an acetylcholinesterase-inhibiting action, (2) An agent as described in the above item (1), wherein the amine compound is a non-carbamate-type compound of the formula:

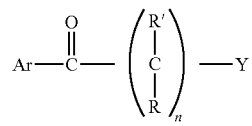

wherein Ar is an optionally condensed phenyl in which the phenyl moiety may be substituted by a substituent or substituents;

n is an integer of 1 to 10;

R and R' are hydrogen, halogen or an optionally substituted hydrocarbon group;

Y is an optionally substituted amino or optionally substituted nitrogen-containing saturated heterocyclic group; or a salt thereof, (3) An agent as described in the above item (2), wherein Ar is a group of the formula:

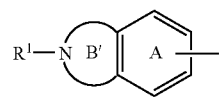

wherein $R^1$ is hydrogen, optionally substituted hydrocarbon group, acyl, or optionally substituted heterocyclic group; the ring A is an optionally substituted benzene ring; the ring B' is a 5- to 9-membered nitrogen-containing heterocycle which may further be substituted by oxo, (4) An agent as described in the above item (2), wherein Ar is a group of the formula:

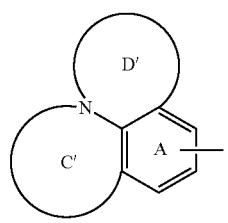

wherein the ring A is an optionally substituted benzene ring; the rings C' and D' each are a 5- to 9-membered nitrogen-containing heterocycle which may further be substituted by oxo, (5) An agent as described in the above item (2), wherein n is 2, (6) An agent as described in the above item (2), wherein R is hydrogen, (7) An agent as described in the above item (2), wherein Y is a group of the formula:

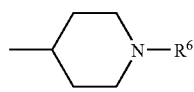

wherein $R^6$ is hydrogen, optionally substituted hydrocarbon group, acyl, or optionally substituted heterocyclic group;

(8) An agent as described in the above item (2), wherein Ar is a group of the formula:

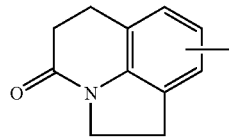

n is 2; R is hydrogen; and Y is a group of the formula:

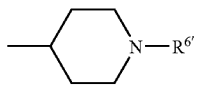

wherein $R^{6'}$ is benzyl which may be substituted by 1 or 2 substituents selected from halogen, $C_{1-3}$ alkyl, $C_{1-3}$ alkoxy, cyano, nitro and hydroxy;

(9) An agent as described in the above item (1) comprising 8-[3-[1-[(3-fluorophenyl)methyl]-4-piperidinyl]-1-oxopropyl]-1,2,5,6-tetrahydro-4H-pyrrolo[3,2,1-ij]quinolin-4-one,
8-[3-[1-(phenylmethyl)-4-piperidinyl]-1-oxopropyl]-1,2,5,6-tetrahydro-4H-pyrrolo[3,2,1-ij]quinolin-4-one,
8-[3-[1-[(2-hydroxyphenyl)methyl]-4-piperidinyl]-1-oxopropyl]-1,2,5,6-tetrahydro-4H-pyrrolo[3,2,1-ij]quinolin-4-one,
or a salt thereof;

(10) An agent as described in the above item (1) which is a prophylactic and therapeutic agent for dysuria;

(11) An agent as described in the above item (1) which is a prophylactic and therapeutic agent for difficulty in urination;

(12) Agent for improving excretory potency of the urinary bladder which comprises a combination of an α-blocker and an amine compound of non-carbamate-type having an acetylcholin-esterase-inhibiting action; and

(13) Crystals of a tricyclic, condensed, heterocyclic derivative and pharmaceutical compositions comprising the crystals, which possess an action to inhibit acetylcholine esterase and an action to improve the excretory potency of urinary bladder.

As a result of intensive investigations, the present inventors have succeeded in obtaining crystals of 8-[3-[1-[(3-fluorophenyl)methyl]-4-piperidinyl]-1-oxopropyl]-1,2,5,6-tetrahydro-4H-pyrrolo[3,2,1-ij]quinolin-4-one, which are high in purity, high in quality, low in hygroscopic property, and extremely excellent in stability without deteriorating upon long-term storage under usual conditions, thereby providing the second aspect of the present invention.

In other words, the present invention also relates to
(i) crystals of 8-[3-[1-[(3-fluorophenyl)methyl]-4-piperidinyl]-1-oxopropyl]-1,2,5,6-tetrahydro-4H-pyrrolo[3,2,1-ij]quinolin-4-one or a salt thereof,
(ii) the crystals described in the above-mentioned item (i), wherein the melting point is above 110° C.,
(iii) the crystals described in the above-mentioned item (i), wherein the melting point is about 113° C. to about 118° C.,
(iv) a pharmaceutical composition which comprises the crystals described in the above-mentioned item (i),
(v) the pharmaceutical composition described in the above-mentioned item (iv), which is an acetylcholine esterase inhibitor,
(vi) the pharmaceutical composition described in the above-mentioned item (iv), which is an agent for improving the excretory potency of urinary bladder,
(vii) the pharmaceutical composition described in the above-mentioned item (iv), which is a therapeutic agent against micturition disorders,
(viii) the pharmaceutical composition described in the above-mentioned item (iv), which is a therapeutic agent against dysuria disorders, and
(ix) agents for improving the excretory potency of urinary bladder, which are characterized by combining crystals of 8-[3-[1-[(3-fluorophenyl)methyl]-4-piperidinyl]-1-oxopropyl]-1,2,5,6-tetrahydro-4H-pyrrolo[3,2,1-ij]quinolin-4-one or a salt thereof with an α-blocker.

BRIEF DESCRIPTION OF THE DRAWING

FIG. 1 shows a powder X-ray crystal diffractometry pattern of the crystals obtained in Example 1.

DETAILED DESCRIPTION OF PREFERRED EMBODIMENTS

The "amine compounds of non-carbamate-type having an acetylcholinesterase-inhibiting action" used in the invention include those which have an acetylcholinesterase-inhibiting action but have no carbamate structure —OCON— in the molecule, and in which the hydrogen atom on ammonia is replaced by a hydrocarbon group, preferably including primary amine compounds, secondary amine compounds, and tertiary amine compounds. More preferably, the following compounds are exemplified. Among these compounds, those which contain at least one 5- to 7-membered nitrogen-containing heterocycle as a partial structure are preferred, and in particular, compounds as described in the following items, 1), 20), 23), 41), 42) and 43) are especially preferred. Among them, particularly preferred are compounds as described in the item 1).

1) Compounds of the formula:

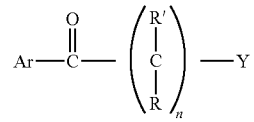

wherein Ar is an optionally condensed phenyl which may have a substituent or substituents;

n is an integer of 1 to 10;

R and R' are hydrogen, halogen or an optionally substituted hydrocarbon group;

Y is an optionally substituted amino or optionally substituted nitrogen-containing saturated heterocyclic group;

or salts thereof (hereinafter also abbreviated to as Compound (I)).

Of particular significance are compounds of the above formula wherein R' is hydrogen:

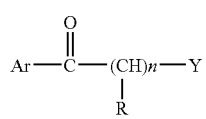

In the above-mentioned formulas, the "substituent" in "the optionally condensed phenyl which may have a substituent or substituents" represented by Ar includes, for example, (i) optionally halogenated lower alkyl, (ii) halogen (e.g., fluoro, chloro, bromo, iodo, etc.), (iii) lower alkylenedioxy (e.g., $C_{1-3}$ alkylenedioxy such as methylenedioxy, ethylenedioxy, etc.), (iv) nitro, (v) cyano, (vi) hydroxy, (vii) optionally halogenated lower alkoxy, (viii) cycloalkyl (e.g., $C_{3-6}$ cycloalkyl such as cyclopropyl, cyclobutyl, cyclopentyl, cyclohexyl, etc.), (ix) optionally halogenated lower alkylthio, (x) amino, (xi) mono-lower alkylamino (e.g., mono-$C_{1-6}$ alkylamino such as methylamino, ethylamino, propylamino, etc.), (xii) di-lower alkylamino (e.g., di-$C_{1-6}$ alkylamino such as dimethylamino, diethylamino, etc.), (xiii) 5- to 7-membered cyclic amino (e.g., 5- to 7-membered cyclic amino which may contain 1 to 3 heteroatoms selected from nitrogen, oxygen and sulfur, etc., in addition to one nitrogen atom (e.g., pyrrolidino, piperidino, piperazino, morpholino, thiomorpholino, etc.)), (xiv) lower alkyl-carbonylamino (e.g., $C_{1-6}$ alkyl-carbonylamino such as acetylamino, propionylamino, butyrylamino, etc.), (xv) lower alkyl-sulfonylamino (e.g., $C_{1-6}$ alkylsulfonylamino such as methylsulfonylamino, ethylsulfonylamino, propylsulfonylamino, etc.), (xvi) lower alkoxy-carbonyl (e.g., $C_{1-6}$ alkoxy-carbonyl such as methoxycarbonyl, ethoxycarbonyl, propoxycarbonyl, isobutoxycarbonyl, etc.), (xvii) carboxy, (xviii) lower alkylcarbonyl (e.g., $C_{1-6}$ alkylcarbonyl such as methylcarbonyl, ethylcarbonyl, butylcarbonyl, etc.), (xix) cycloalkylcarbonyl (e.g., $C_{3-6}$ cycloalkylcarbonyl such as cyclopropylcarbonyl, cyclobutylcarbonyl, cyclopentylcarbonyl, cyclohexylcarbonyl, etc.), (xx) carbamoyl, thiocarbamoyl, (xxi) mono-lower alkyl-carbamoyl (e.g., mono-$C_{1-6}$ alkyl-carbamoyl such as methylcarbamoyl, ethylcarbamoyl, propylcarbamoyl, butylcarbamoyl, etc.), (xxii) di-lower alkyl-carbamoyl (e.g., di-$C_{1-6}$ alkyl-carbamoyl such as diethylcarbamoyl, dibutylcarbamoyl, etc.), (xxiii) lower alkylsulfonyl (e.g., $C_{1-6}$ alkylsulfonyl such as methylsulfonyl, ethylsulfonyl, propylsulfonyl, etc.), (xxiv) cycloalkylsulfonyl (e.g., $C_{3-6}$ cycloalkylsulfonyl such as cyclopentylsulfonyl, cyclohexylsulfonyl, etc.), (xxv) phenyl, (xxvi) naphthyl, (xxvii) mono-phenyl-lower alkyl (e.g., mono-phenyl-$C_{1-6}$ alkyl such as benzyl, phenylethyl, etc.), (xxviii) di-phenyl-lower alkyl (e.g., di-phenyl-$C_{1-6}$ alkyl such as diphenylmethyl, diphenylethyl, etc.), (xxix) mono-phenyl-lower alkyl-carbonyloxy (e.g., mono-phenyl-$C_{1-6}$ alkyl-carbonyloxy such as phenyl-methylcarbonyloxy, phenylethylcarbonyloxy, etc.), (xxx) di-phenyl-lower alkyl-carbonyloxy (e.g., diphenyl-$C_{1-6}$ alkyl-carbonyloxy such as diphenylmethylcarbonyloxy, diphenylethylcarbonyloxy, etc.), (xxxi) phenoxy, (xxxii) mono-phenyl-lower alkyl-carbonyl (e.g., mono-phenyl-$C_{1-6}$ alkyl-carbonyl such as phenylmethylcarbonyl, phenyl-ethylcarbonyl, etc.), (xxxiii) di-phenyl-lower alkyl-carbonyl (e.g., di-phenyl-$C_{1-6}$ alkyl-carbonyl such as diphenylmethylcarbonyl, diphenylethylcarbonyl, etc.), (xxxiv) benzoyl, (xxxv) phenoxycarbonyl, (xxxvi) phenyl-lower alkyl-carbamoyl (e.g., phenyl-$C_{1-6}$ alkyl-carbamoyl such as phenyl-methylcarbamoyl, phenyl-ethylcarbamoyl, etc.), (xxxvii) phenylcarbamoyl, (xxxviii) phenyl-lower alkyl-carbonylamino (e.g., phenyl-$C_{1-6}$ alkyl-carbonylamino such as phenyl-methylcarbonylamino, phenyl-ethylcarbonylamino, etc.), (xxxix) phenyl-lower alkylamino (e.g., phenyl-$C_{1-6}$ alkylamino such as phenyl-methylamino, phenyl-ethylamino, etc.), (xxxx) phenyl-lower alkylsulfonyl (e.g., phenyl-$C_{1-6}$ alkylsulfonyl such as phenyl-methyl-sulfonyl, phenyl-ethylsulfonyl, etc.), (xxxxi) phenylsulfonyl, (xxxxii) phenyl-lower alkylsulfinyl (e.g., phenyl-$C_{1-6}$ alkylsulfinyl such as phenyl-methylsulfinyl, phenyl-ethylsulfinyl, etc.), (xxxxiii) phenyl-lower alkylsulfonylamino (e.g., phenyl-$C_{1-6}$ alkylsulfonylamino such as phenyl-methylsulfonylamino, phenyl-ethylsulfonylamino, etc.), and (xxxxiv) phenylsulfonylamino (wherein the phenyl, naphthyl, mono-phenyl-lower alkyl, di-phenyl-lower alkyl, mono-phenyl-lower alkyl-carbonyloxy, di-phenyl-lower alkyl-carbonyloxy, phenoxy, mono-phenyl-lower alkyl-carbonyl, di-phenyl-lower alkyl-carbonyl, benzoyl, phenoxycarbonyl, phenyl-lower alkyl-carbamoyl, phenylcarbamoyl, phenyl-lower alkyl-carbonylamino, phenyl-lower alkylamino, phenyl-lower alkylsulfonyl, phenylsulfonyl, phenyl-lower alkylsulfinyl, phenyl-lower alkylsulfonylamino and phenylsulfonylamino as mentioned above in (xxv) to (xxxxiv) may further be substituted by 1 to 4 substituents selected from lower alkyl (e.g., $C_{1-6}$ alkyl such as methyl, ethyl, propyl, isopropyl, butyl, sec-butyl, tert-butyl, pentyl, hexyl, etc.), lower alkoxy (e.g., $C_{1-6}$ alkoxy such as methoxy, ethoxy, propoxy, isopropoxy, butoxy, isobutoxy, sec-butoxy, tert-butoxy, etc.), halogen (e.g., chloro, bromo, iodo, etc.), hydroxy, benzyloxy, amino, mono-lower alkylamino (e.g., mono-$C_{1-6}$ alkylamino such as methylamino, ethylamino, propylamino, etc.), di-lower alkylamino (e.g., di-$C_{1-6}$ alkylamino such as dimethylamino, diethylamino, etc.), nitro, lower alkyl-carbonyl (e.g., $C_{1-6}$ alkyl-carbonyl such as methylcarbonyl, ethylcarbonyl, butylcarbonyl, etc.), benzoyl, and the like). Said phenyl may be substituted by 1 to 4 of these substituents.

The "optionally halogenated lower alkyl" as mentioned above includes, for example, lower alkyl (e.g., $C_{1-6}$ alkyl such as methyl, ethyl, propyl, isopropyl, butyl, sec-butyl, tert-butyl, pentyl, hexyl, etc.) which may have 1 to 3 halogen atoms (e.g. chloro, bromo, iodo, etc.), and is exemplified by methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, and the like.

The "optionally halogenated lower alkoxy" as mentioned above to includes, for example, lower alkoxy (e.g., $C_{1-6}$ alkoxy such as methoxy, ethoxy, propoxy, isopropoxy, butoxy, isobutoxy, sec-butoxy, tert-butoxy, etc.) which may have 1 to 3 halogen atoms (e.g. chloro, bromo, Iodo, etc.), and is exemplified by methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, and the like.

The "optionally halogenated lower alkylthio" as mentioned above includes, for example, lower alkylthio (e.g., $C_{1-6}$ alkylthio such as methylthio, ethylthio, propylthio, isopropylthio, butylthio, isobutylthio, sec-butylthio, tert-butylthio, etc.) which may have 1 to 3 halogen atoms (e.g. chloro, bromo, iodo, etc.), and is exemplified by methylthio, difluoromethylthio, trifluoromethylthio, ethylthio, propylthio, isopropylthio, butylthio, 4,4,4-trifluorobutylthio, isobutylthio, sec-butylthio, tert-butylthio, pentylthio, hexylthio, and the like.

The "substituent" in "optionally condensed phenyl which may have a substituent or substituents" includes preferably, (i) amino, (ii) mono-lower alkylamino (e.g., mono-$C_{1-6}$ alkylamino such as methylamino, ethylamino, propylamino, etc.), (iii) di-lower alkylamino (e.g., di-$C_{1-6}$ alkylamino such as dimethylamino, diethylamino, etc.), (iv) 5- to 7-membered cyclic amino which may contain, for example, 1 to 3 heteroatoms selected from nitrogen, oxygen and sulfur, etc., in addition to one nitrogen atom (e.g., pyrrolidino, piperidino, piperazino, morpholino, thiomorpholino, etc.), (v) lower alkyl-carbonylamino (e.g., $C_{1-6}$ alkyl-carbonylamino such as acetylamino, propionylamino, butyrylamino, etc.), (vi) lower alkyl-sulfonylamino (e.g., $C_{1-6}$ alkylsulfonylamino such as methylsulfonylamino, ethylsulfonylamino, propylsulfonylamino etc.), (vii) phenyl-lower alkylamino (e.g., phenyl-$C_{1-6}$ alkylamino such as phenyl-methylamino, phenyl-ethylamino, etc.), (viii) phenyl-lower alkylsulfonylamino (e.g., phenyl-lower $C_{1-6}$ alkylsulfonylamino such as phenyl-methylsulfonylamino, phenyl-ethylsulfonylamino, etc.), (ix) phenylsulfonylamino, (x) halogen (e.g. fluoro, chloro, etc.), (xi) optionally halogenated lower alkyl (e.g., methyl, ethyl, isopropyl, tert-butyl, trifluoromethyl, etc.) and (xii) optionally halogenated lower alkoxy (e.g., methoxy, ethoxy, isopropoxy, tert-butoxy, trifluoromethoxy, etc.). Particularly preferred are di-lower alkylamino (e.g., di-$C_{1-6}$ alkylamino such as dimethylamino, di-ethylamino, etc.), 5- to 7-membered cyclic amino which may contain 1 to 3 heteroatoms selected from nitrogen, oxygen and sulfur, etc., in addition to one nitrogen atom (e.g., pyrrolidino, piperidino, piperazino, morpholino, thiomorpholino, etc.), and the like.

The condensed "phenyl" of "optionally condensed phenyl which may have a substituent or substituents" is exemplified by, for example, (1) an example in which the phenyl is condensed with an optionally substituted mono-cyclic heterocycle;

(2) an example in which the phenyl is condensed with an optionally substituted bicyclic heterocycle or with two of the same or different mono-cyclic groups (provided that at least one of two is a mono-cyclic heterocycle); and (3) an example in which the phenyl is condensed with an optionally substituted tricyclic heterocycle.

When the phenyl of "optionally condensed phenyl which may have a substituent or substituents" is condensed with a mono-cyclic heterocycle, a group of the formula:

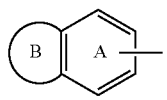

wherein ring A is an optionally substituted benzene ring; and ring B is an optionally substituted heterocycle;
is exemplified.

As for the substituent on ring A, the "substituent" of "optionally condensed phenyl which may have a substituent or substituents" are exemplified. The number of substituents is 1 to 3.

The "heterocycle" of "optionally substituted heterocycle" represented by ring B includes 4- to 14-membered (preferably 5- to 9-membered) aromatic or non-aromatic heterocycles which contain 1 to 4 heteroatoms selected from, for example, nitrogen, oxygen and sulfur. Such heterocycles are exemplified by pyridine, pyrazine, pyrimidine, imidazole, furan, thiophene, dihydropyridine, diazepine, oxazepine, pyrrolidine, piperidine, hexamethyleneimine, heptamethyleneimine, tetrahydrofuran, piperazine, homopiperazine, tetrahydroxazepine, morpholine, thiomorpholine, pyrrole, pyrazole, 1,2,3-triazole, oxazole, oxazolidine, thiazole, thiazolidine, isoxazole, imidazoline, and the like. Among these heterocycles, 5- to 9-membered non-aromatic heterocycles containing 1 heteroatom or 2 identical or different heteroatoms (e.g., pyrrolidine, piperidine, hexamethyleneimine, heptamethyleneimine, tetra-hydrofuran, piperazine, homopiperazine, tetrahydroxazepine, morpholine, thiomorpholine, etc.) are preferred. Particularly preferred are (1) non-aromatic heterocycles containing 1 heteroatom selected from, for example, nitrogen, oxygen and sulfur, and (2) non-aromatic heterocycles containing 1 nitrogen atom and 1 heteroatom selected from nitrogen, oxygen and sulfur.

As the "substituent" of "optionally substituted heterocycle" represented by ring B, the following 1 to 5 substituents may be used: (i) halogen (e.g., fluoro, chloro, bromo, iodo, etc.), (ii) nitro, (iii) cyano, (iv) oxo, (v) hydroxy, (vi) lower alkyl (e.g., $C_{1-6}$ alkyl such as methyl, ethyl, propyl, isopropyl, butyl, isobutyl, tert-butyl, sec-butyl, etc.), (vii) lower alkoxy (e.g., $C_{1-6}$ alkoxy such as methoxy, ethoxy, propyloxy, isopropyloxy, butyloxy, etc.), (viii) lower alkylthio (e.g., $C_{1-6}$ alkylthio such as methylthio, ethylthio, propylthio, etc.), (ix) amino, (x) mono-lower alkylamino (e.g., mono-$C_{1-6}$ alkylamino such as methylamino, ethylamino, propylamino, etc.), (xi) di-lower alkylamino (e.g., di-$C_{1-6}$ alkylamino such as dimethylamino, diethylamino, etc.), (xii) 5- to 7-membered cyclic amino which may contain 1 to 3 heteroatoms selected from, for example, nitrogen, oxygen and sulfur, in addition to carbon atoms and one nitrogen atom (e.g., pyrrolidino, piperidino, piperazino, morpholino, thiomorpholino, etc.), (xiii) lower alkyl-carbonylamino (e.g., $C_{1-6}$ alkyl-carbonylamino such as acetylamino, propionylamino, butyrylamillo, etc.), (xiv) lower alkylsulfonylamino (e.g., $C_{1-6}$ alkylsulfonylamino such as methylsulfonylamino, ethylsulfonylamino, etc.), (xv) lower alkoxy-carbonyl (e.g., $C_{1-6}$ alkoxy-carbonyl such as methoxycarbonyl, ethoxycarbonyl, propoxycarbonyl, etc.), (xvi) carboxy, (xvii) lower alkylcarbonyl (e.g., $C_{1-6}$ alkylcarbonyl such as methylcarbonyl, ethylcarbonyl, propylcarbonyl, etc.), (xviii) carbamoyl, (xix) mono-lower alkylcarbamoyl (e.g., mono-$C_{1-6}$ alkyl-carbamoyl such as methylcarbamoyl, ethylcarbamoyl, etc.), (xx) di-lower alkylcarbamoyl (e.g., di-$C_{1-6}$ alkyl-carbamoyl such as dimethylcarbamoyl, diethylcarbamoyl, etc.), (xxi) lower to alkylsulfonyl (e.g., $C_{1-6}$ alkylsulfonyl such as methylsulfonyl, ethylsulfonyl, propylsulfonyl, etc.), and the like. Among these substituents, oxo, lower alkyl (e.g., $C_{1-6}$ alkyl such as methyl, ethyl, propyl, isopropyl, butyl, isobutyl, tert-butyl, sec-butyl, etc.), and the like are preferred. Particularly preferred is oxo.

When ring B contains a nitrogen atom in the ring, it may have a group of the formula:

wherein $R^1$ is hydrogen, optionally substituted hydrocarbon group, acyl, or optionally substituted heterocyclic group;
in the ring. In addition, ring B may contain 1 to 3 of the above-mentioned substituents (i) to (xxi).

The "hydrocarbon group" of "optionally substituted hydrocarbon group" indicates a group which is formed from a hydrocarbon compound by removing one hydrogen atom, and is exemplified, for example, by the following: alkyl, alkenyl, alkynyl, cycloalkyl, aryl, aralkyl, a combination of these groups, and the like. Among these groups, $C_{1-16}$ hydrocarbon group is preferred.

(1) Alkyl (e.g., $C_{1-6}$ alkyl such as methyl, ethyl, propyl, isopropyl, butyl, isobutyl, tert-butyl, sec-butyl, pentyl, hexyl, etc.)

(2) Alkenyl (e.g., $C_{2-6}$ alkenyl such as vinyl, allyl, isopropenyl, butenyl, isobutenyl, sec-butenyl, etc.)

(3) Alkynyl (e.g., $C_{2-6}$ alkynyl such as propargyl, ethynyl, butynyl, 1-hexynyl, etc.)

(4) Cycloalkyl (e.g., $C_{3-6}$ cycloalkyl such as cyclopropyl, cyclobutyl, cyclopentyl, cyclohexyl, etc.)

(5) Bridged cyclic lower saturated hydrocarbon group (e.g., bridged cyclic $C_{8-14}$ saturated hydrocarbon group such as bicyclo[3.2.1]oct-2-yl, bicyclo[3.3.1]non-2-yl, adamantan-1-yl, etc.)

(6) Aryl (e.g., $C_{6-14}$ aryl such as phenyl, 1-naphthyl, 2-naphthyl, biphenyl, 2-indenyl, 2-anthryl, etc. Phenyl is preferred.)

(7) Aralkyl (e.g., $C_{7-16}$ aralkyl such as: phenyl-$C_{1-10}$ alkyl such as benzyl, phenylethyl, phenylpropyl, phenylbutyl, phenylpentyl, phenylhexyl, etc.; naphthyl-$C_{1-6}$ alkyl such as α-naphthylmethyl, etc.; a $C_{7-10}$ aralkyl exampled by diphenyl-$C_{1-3}$ alkyl such as diphenylmethyl, diphenylethyl, etc.)

(8) Aryl-alkenyl (e.g., $C_{6-14}$ aryl-$C_{2-12}$ alkenyl such as: phenyl-$C_{2-12}$ alkenyl such as styryl, cinnamyl, 4-phenyl-2-butenyl, 4-phenyl-3-butenyl, etc.)

(9) Aryl-$C_{2-12}$ alkynyl (e.g., $C_{6-14}$ aryl-$C_{2-12}$ alkynyl such as: phenyl-$C_{2-12}$ alkynyl such as phenylethynyl, 3-phenyl-2-propynyl, 3-phenyl-1-propynyl, etc.)

(10) Cycloalkyl-alkyl (e.g., $C_{3-7}$ cycloalkyl-$C_{1-6}$ alkyl such as cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, cycloheptylethyl, cyclopropylpropyl, cyclobutylpropyl, cyclopentylpropyl, cyclohexylpropyl, cycloheptylpropyl, cyclopropylbutyl, cyclobutylbutyl, cyclopentylbutyl, cyclohexylbutyl, cycloheptylbutyl, cyclopropylpentyl, cyclobutylpentyl, cyclopentylpentyl, cyclohexylpentyl, cycloheptylpentyl, cyclopropylhexyl, cyclobutylhexyl, cyclopentylhexyl, cyclohexylhexyl, etc.)

(11) Aryl-aryl-$C_{1-10}$ alkyl (e.g., biphenylmethyl, biphenylethyl, etc.)

The "hydrocarbon group" of "optionally substituted hydrocarbon group" represented by $R^1$ preferably includes, for example, $C_{1-6}$ alkyl, $C_{3-6}$ cycloalkyl, $C_{7-16}$ aralkyl, and the like. Particularly preferred are $C_{7-16}$ aralkyl (e.g., phenyl-$C_{1-4}$ alkyl such as benzyl, phenylethyl, phenylpropyl, etc.), and the like.

As the "substituent" of "optionally substituted hydrocarbon group" represented by $R^1$, the following 1 to 5 substituents (preferably, 1 to 3 substituents) may be used: (i) halogen (e.g., fluoro, chloro, bromo, Iodo, etc.), (ii) nitro, (iii) cyano, (iv) oxo, (v) hydroxy, (vi) optionally halogenated lower alkyl, (vii) optionally halogenated lower alkoxy, (viii) optionally halogenated lower alkylthio, (ix) amino, (x) mono-lower alkylamino (e.g., mono-$C_{1-6}$ alkylamino such as methylamino, ethylamino, propylamino, etc.), (xi) di-lower alkylamino (e.g., di-$C_{1-6}$ alkylamino such as dimethylamino, diethylamino, etc.), (xii) 5- to 7-membered cyclic amino which may contain 1 to 3 heteroatoms selected from, for example, nitrogen, oxygen and sulfur, etc., in addition to carbon atoms and one nitrogen atom (e.g., pyrrolidino, piperidino, piperazino, morpholino, thio-morpholino, etc.), (xiii) lower alkyl-carbonylamino (e.g., $C_{1-6}$ alkyl-carbonylamino such as acetylamino, propionylamino, butyrylamino, etc.), (xiv) lower alkyl-sulfonylamino (e.g., $C_{1-6}$ alkyl-sulfonylamino such as methylsulfonylamino, ethylsulfonylamino, etc.), (xv) lower alkoxy-carbonyl (e.g., $C_{1-6}$ alkoxy-carbonyl such as methoxycarbonyl, ethoxycarbonyl, propoxycarbonyl, etc.), (xvi) carboxy, (xvii) lower alkyl-carbonyl (e.g., $C_{1-6}$ alkyl-carbonyl such as methylcarbonyl, ethylcarbonyl, propylcarbonyl, etc.), (xviii) carbamoyl, thiocarbamoyl, (xix) mono-lower alkyl-carbamoyl (e.g., mono-$C_{1-6}$ alkyl-carbamoyl such as methylcarbamoyl, ethylcarbamoyl, etc.), (xx) di-lower alkyl-carbamoyl (e.g., di-$C_{1-6}$ alkyl-carbamoyl such as dimethylcarbamoyl, diethylcarbamoyl, etc.), (xxi) lower alkylsulfonyl (e.g., $C_{1-6}$ alkylsulfonyl such as methylsulfonyl, ethylsulfonyl, propylsulfonyl, etc.), (xxii) lower alkoxycarbonyl-lower alkyl (e.g., $C_{1-6}$ alkyl-carbonyl-$C_{1-6}$ alkyl such as methoxycarbonylmethyl, ethoxycarbonylmethyl, tert-butoxycarbonyl methyl, methoxycarbonylethyl, methoxycarbonylmethyl, methoxycarbonyl(di methyl) methyl, ethoxycarbonyl(dimethyl)methyl, tert-butoxycarbonyl(dimethyl)methyl, etc.), (xxiii) carboxy-lower alkyl (e.g., carboxy-$C_{1-6}$ alkyl such as carboxylmethyl, carboxylethyl, carboxyl(dimethyl)methyl, etc.), (xxiv) optionally substituted heterocycle, (xxv) $C_{6-14}$ aryl (e.g., phenyl, naphthyl, etc.), (xxvi) $C_{7-16}$ aralkyl (e.g., benzyl, etc.), (xxvii) optionally substituted ureido (e.g., ureido, 3-methylureido, 3-ethylureido, 3-phenylureido, 3-(4-fluorophenyl)ureido, 3-(2-methylphenyl)ureido, 3-(4-methoxyphenyl)ureido, 3-(2,4-difluorophenyl)ureido, 3-[3,5-bis(trifluoromethyl)phenyl]ureido, 3-benzylphenylureido, 3-(1-naphthyl)ureido, 3-(2-biphenyl)ureido, etc.), (xxviii) optionally substituted thioureido (e.g., thioureido, 3-methylthioureido, 3-ethylthioureido, 3-phenylthioureido, 3-(4-fluorophenyl)thioureido, 3-(4-methylphenyl)thioureido, 3-(4-methoxyphenyl)thioureido, 3-(2,4-dichlorophenyl)thioureido, 3-benzylthioureido, 3-(1-naphthyl)thioureido, etc.), (xxix) optionally substituted amidino (e.g., amidino, N'-methylamidino, N'-ethylamidino, N'-phenylamidino, $N^1,N^1$-dimethylamidino, $N^1,N^2$-dimethylamidino, $N^1$-methyl-$N^1$-ethylamidino, $N^1,N^1$-diethylamidino, $N^1$-methyl-$N^1$-phenylamidino, $N^1,N^1$-di(4-nitrophenyl)amidino, etc.), (xxx) optionally substituted guanidino (e.g., guanidino, 3-methylguanidino, 3,3-dimethylguanidino, 3,3-diethylguanidino, etc.), (xxxi) optionally substituted cyclic aminocarbonyl (e.g., pyrrolidinocarbonyl, piperidinocarbonyl, (4-methylpiperidino)carbonyl, (4-phenylpiperidino)carbonyl, (4-benzylpiperidino)carbonyl, (4-benzoylpiperidino)carbonyl, [4-(4-fluorobenzoyl)piperidino]carbonyl, (4-methylpiperazino)carbonyl, (4-phenylpiperazino)carbonyl, [4-(4-nitrophenyl)piperazino]-carbonyl, (4-benzylpiperazino)carbonyl, morpholinocarbonyl, thiomorpholinocarbonyl, etc.), (xxxii) optionally substituted aminothiocarbonyl (e.g., aminothiocarbonyl, methylaminothiocarbonyl, dimethylaminothiocarbonyl, etc.), (xxxiii) optionally substituted aminosulfonyl (e.g., aminosulfonyl, methylaminosulfonyl, dimethylaminosulfonyl, etc.), (xxxiv) optionally substituted phenylsulfonylamino (e.g., phenylsulfonylamino, (4-methylphenyl)sulfonylamino, (4-chlorophenyl)sulfonylamino, (2,5-dichlorophenyl)sulfonylamino, (4-methoxyphenyl)sulfonylamino, (4-acetylamino-phenyl)sulfonylamino, (4-nitrophenyl)sulfonylamino, etc.), (xxxv) sulfo, (xxxvi) sulfino, (xxxvii) sulfeno, (xxxviii) $C_{1-6}$ alkylsulfo (e.g., methylsulfo, ethylsulfo, propylsulfo, etc.), (xxxix) $C_{1-6}$ alkylsulfino (e.g., methylsulfino, ethylsulfino, propylsulfino, etc.), (xxxx) $C_{1-6}$ alkylsulfeno (e.g., methylsulfeno, ethylsulfeno, propylsulfeno, etc.), (xxxxi) phosphono, (xxxxii) di-$C_{1-6}$ alkoxyphosphoryl (e.g., dimethoxyphosphoryl, di-ethoxyphosphoryl, dipropoxyphosphoryl, etc.).

Among these substituents, preferred ones include halogen, optionally halogenated alkyl, optionally halogenated alkoxy, hydroxy, nitro, cyano, carboxy, $C_{1-6}$ alkoxy-carbonyl, carbamoyl, aminothiocarbonyl, mono-$C_{1-6}$ alkyl-carbamoyl, di-$C_{1-6}$ alkyl-carbamoyl, amino, mono-$C_{1-6}$ alkylamino, di-$C_{1-6}$ alkylamino, 5- to 7-membered cyclic amino, $C_{1-6}$ alkyl-carbonylamino, phenylsulfonylamino, $C_{1-6}$ alkylsulfonylamino, and the like.

As the "heterocyclic group" of "optionally substituted heterocyclic group" above-mentioned, for example, a group may be used which is formed from a 5- to 14-membered (monocyclic or bi- to tetra-cyclic) heterocycle containing 1 to 6 (preferably, 1 to 4) heteroatoms selected from nitrogen, oxygen, sulfur and the like by removing one hydrogen atom.

The monocyclic heterocyclic group includes those derived from the following monocyclic heterocycles by removing one hydrogen atom: pyridine, pyrazine, pyrimidine, imidazole, furan, thiophene, dihydropyridine, diazepine, oxazepine, pyrrolidine, piperidine, hexamethylenimine, heptamethylenimine, tetrahydrofuran, piperazine, homopiperazine, tetrahydrooxazepine, morpholine, thiomorpholine, pyrrole, pyrazole, 1,2,3-triazole, oxazole, oxazolidine, thiazole, thiazolidine, isoxazole, imidazoline, triazole, thiadiazole, oxadiazole, oxathiadiazole, triazine, tetrazole, and the like.

The bicyclic heterocyclic group includes those derived from the following bicyclic heterocycles by removing one hydrogen atom: indole, dihydroindole, isoindole, dihydroisoindole, benzofuran, dihydrobenzofuran, benzimidazole, benzoxazole, benzisoxazole, benzothiazole, indazole, quinoline, tetrahydroquinoline, isoquinoline, tetrahydroisoquinoline, tetrahydro-1H-1-benzazepine, tetrahydro-1H-2-benzazepine, tetrahydro-1H-3-benzazepine, tetrahydrobenzoxazepine, quinazoline, tetrahydroquinazoline, quinoxaline, tetrahydroquinoxaline, benzodioxane, benzodioxole, benzothiazine, imidazopyridine, and the like.

The tri- or tetra-cyclic heterocyclic group includes those derived from the following tri- or tetra-cyclic heterocycles by removing one hydrogen atom: acridine, tetrahydroacridine, pyrroloquinol ine, pyrro loindole, cyclopentaindole, isoindolobenzazepine, and the like.

The "heterocyclic group" preferably includes those derived from monocyclic or bicyclic heterocycles by removing one hydrogen atom.

As for the "substituent" in said "optionally substituted heterocyclic group", those of the "optionally substituted heterocycle" represented by the above-mentioned ring B are exemplified. The number of substituents is 1 to 5.

The "optionally substituted hydrocarbon group" represented by $R^1$ preferably includes $C_{7-16}$ aralkyl (preferably, benzyl, etc.) which may contain 1 to 5 of substituents selected from halogen, $C_{1-6}$ alkyl, $C_{1-6}$ alkoxy, nitro, cyano and hydroxy.

The "acyl" represented by the above-mentioned $R^1$ includes those indicated by the formula: —(C=O)—$R^2$, —(C=O)—$OR^2$, —(C=O)—$NR^2R^3$, —$SO_2$—$R^2$, —SO—$R^2$, —(C=S)—$OR^2$ or —(C=S)$NR^2R^3$ wherein $R^2$ and $R^3$ each is (i) hydrogen, (ii) optionally substituted hydrocarbon group or (iii) optionally substituted heterocyclic group, or $R^2$ and $R^3$ taken together with the adjacent nitrogen atom may form an optionally substituted nitrogen-containing cyclic group.

Among these groups, the acyl of the formula —(C=O)—$R^2$ or —(C=O)—$NR^2R^3$ wherein each symbol has the same meaning as mentioned above is preferred.

The "optionally substituted hydrocarbon group" and "optionally substituted heterocyclic group" represented by $R^2$ or $R^3$, respectively include the same groups as the "optionally substituted hydrocarbon group" and "optionally substituted heterocyclic group" represented by the above-mentioned $R^1$.

The "optionally substituted nitrogen-containing cyclic group" formed by $R^2$ and $R^3$ includes 5- to 9-membered (preferably, 5- to 7-membered) nitrogen-containing saturated heterocyclic group which may contain 1 to 3 heteroatoms selected from, for example, nitrogen, oxygen and sulfur, in addition to carbon atoms and one nitrogen atom. Such a group is exemplified, for example, by groups of formulae:

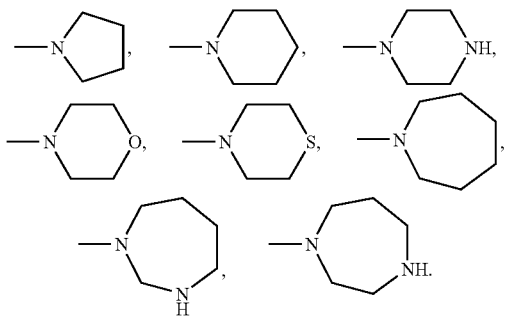

As for the "substituent" of "optionally substituted nitrogen-containing cyclic group", the same ones as in the "optionally substituted heterocycle" represented by the aforementioned ring B are exemplified. The number of substituents is 1 to 5.

$R^2$ and $R^3$ preferably includes (i) hydrogen, (ii) optionally halogenated $C_{1-6}$ alkyl, (iii) $C_{6-10}$ aryl optionally substituted by 1 to 3 substituents selected from $C_{1-6}$ alkyl and $C_{1-6}$ alkoxy, (iv) $C_{7-16}$ aralkyl (e.g., benzyl, etc.), (v) 5- or 6-membered, heterocyclic group (e.g., pyridyl, thienyl, furyl, etc.), and the like.

The "acyl" represented by the above-mentioned $R^1$, preferably, includes formyl, optionally halogenated $C_{1-6}$ alkyl-carbonyl (e.g., acetyl, trifluoroacetyl, propionyl, etc.), 5- or 6-membered heterocycle-carbonyl (e.g., pyridylcarbonyl, thienylcarbonyl, furylcarbonyl, etc.), $C_{6-14}$ aryl-carbonyl (e.g., benzoyl, 1-naphthoyl, 2-naphthoyl, etc.), $C_{7-16}$ aralkyl-carbonyl (e.g., phenylacetyl, 3-phenylpropionyl, etc.), $C_{6-10}$ aryl-sulfonyl (e.g., benzenesulfonyl, naphthylsulfonyl, etc.), and the like.

$R^1$ is, preferably, hydrogen, $C_{1-6}$ alkyl, $C_{1-6}$ alkyl-carbonyl, $C_{6-14}$ aryl-carbonyl, and the like.

The group of the above-mentioned formula:

includes groups derived from bicyclic condensed benzene rings by removing one hydrogen atom, which are exemplified by 2,3-dihydrobenzofuran; 3,4-dihydro-2H-1-benzothiopyran; 2,3-dihydro-1H-indole; 1,2,3,4-tetrahydroquinoline; 2,3-dihydro-1H-isoindole; 1,2,3,4-tetrahydroisoquinoline; benzazepine such as 2,3,4,5-tetrahydro-1H-1-benzazepine, 2,3,4,5-tetrahydro-1H-2-benzazepine, 2,3,4,5-tetrahydro-1H-3-benzazepine, etc.; benzazocine such as 1,2,3,4,5,6-hexahydro-1-benzazocine, 1,2,3,4,5,6-hexahydro-2-benzazocine, 1,2,3,4,5,6-hexahydro-3-benzazocine, etc.; benzazonine such as 2,3,4,5,6,7-hexahydro-1H-1-benzazonine, 2,3,4,5,6,7-hexahydro-1H-2-benzazonine, 2,3,4,5,6,7-hexahydro-1H-3-benzazonine, 2,3,4,5,6,7-hexahydro-1H-4-benzazonine, etc.; benzoxazole such as 2,3-dihydrobenzoxazole, etc.; benzothiazole such as 2,3-dihydrobenzothiazole, etc.; benzimidazole such as 2,3-dihydro-1H-benzimidazole, etc.; benzoxazine such as 3,4-dihydro-1H-2,1-benzoxazine, 3,4-dihydro-1H-2,3-benzoxazine, 3,4-dihydro-2H-1,2-benzoxazine, 3,4-dihydro-2H-1,4-benzoxazine, 3,4-dihydro-2H-1,3-benzoxazine, 3,4-dihydro-2H-3,1-benzoxazine, etc.; benzothiazine such as 3,4-dihydro-1H-2,1-benzothiazine, 3,4-dihydro-1H-2,3- benzothiazine, 3,4-dihydro-2H-1,2-benzothiazine, 3,4-dihydro-2H-1,4-benzothiazine, 3,4-dihydro-2H-1,3-benzo-thiazine, 3,4-dihydro-2H-3,1-benzothiazine, etc.; benzodiazine such as 1,2,3,4-tetrahydrocinnoline, 1,2,3,4-tetrahydrophthalazine, 1,2,3,4-tetrahydroquinazoline, 1,2,3,4-tetrahydroquinoxaline, etc.; benzoxathiin such as 3,4-dihydro-1,2-benzoxathiin, 3,4-dihydro-2,1-benzoxathiin, 2,3-dihydro-1,4-benzoxathiin, 1,4-dihydro-2,3-benzoxathiin, 4H-1,3-benzoxathiin, 4H-3,1-benzoxathiin, etc.; benzodioxin such as 3,4-dihydro-1,2-benzodioxin, 2,3-dihydro-1,4-benzodioxin, 1,4-dihydro-2,3-benzodioxin, 4H-1,3-benzodioxin, etc.; benzdithiin such as 3,4-dihydro-1,2-benzdithiin, 2,3-dihydro-1,4-benzdithiin, 1,4-dihydro-2,3-benzdithiin, 4H-1,3-benzdithiin, etc.; benzoxazepine such as 2,3,4,5-tetrahydro-1,2-benzoxazepine, 2,3,4,5-tetrahydro-1,3-benzoxazepine, 2,3,4,5-tetrahydro-1,4-benzoxazepine, 2,3,4,5-tetrahydro-1,5-benzoxazepine, 1,3,4,5-tetrahydro-2,1-benzoxazepine, 1,3,4,5-tetrahydro-2,3-benzoxazepine, 1,3,4,5-tetrahydro-2,4-benzoxazepine, 1,2,4,5-tetrahydro-3,1-benzoxazepine, 1,2,4,5-tetrahydro-3,2-benzoxazepine, 1,2,3,5-tetrahydro-4,1-benzoxazepine, etc.; benzothiazepine such as 2,3,4,5-tetrahydro-1,2-benzothiazepi ne, 2,3,4,5-tetrahydro-1,4-benzothiazepine, 2,3,4,5-tetrahydro-1,5-benzothiazepine, 1,3,4,5-tetrahydro-2,1-benzothiazepine, 1,3,4,5-tetrahydro-2,4-benzothiazepine, 1,2,4,5-tetrahydro-3,1-benzothiazepine, 1,2,4,5-tetrahydro-3,2-benzothiazepine, 1,2,3,5-tetrahydro-4,1-benzothiazepine, etc.; benzodiazepine such as 2,3,4,5-tetrahydro-1H-1,2-benzodiazepine, 2,3,4,5-tetrahydro-1H-1,3-benzodiazepine, 2,3,4,5-tetrahydro-1H-1,4-benzodiazepine, 2,3,4,5-tetrahydro-1H-1,5-benzodiazepine, 2,3,4,5-tetrahydro-1H-2,3-benzodiazepine, 2,3,4,5-tetrahydro-1H-2,4-benzodiazepine, etc.; benzodioxepine such as 4,5-dihydro-1,3-benzodioxepine, 4,5-dihydro-3H-1,2-benzodioxepine, 2,3-dihydro-5H-1,4-benzodioxepine, 3,4-dihydro-1H-1,5-benzodioxepine, 4,5-dihydro-1H-2,3-benzodioxepine, 1,5-dihydro-2,4-benzodioxepine, etc.; benzothiepine such as 4,5-dihydro-1H-2,3-benzothiepine, 1,5-dihydro-2,4-benzothiepine, 3,4-dihydro-2H-1,5-benzothiepine, 2,3-dihydro-5H-1,4-benzothiepine, etc.; benzoxazocine such as 3,4,5,6-tetrahydro-2H-1,5-benzoxazocine, 3,4,5,6-tetrahydro-2H-1,6-benzoxazocine, etc.; benzothiazocine such as 3,4,5,6-tetrahydro-2H-1,5-benzothiazocine, 3,4,5,6-tetrahydro-2H-1,6-benzothiazocine, etc.; benzodiazocine such as 1,2,3,4,5,6-hexahydro-1,6-benzodiazocine, etc.; benzoxathiocine such as 2,3,4,5-tetrahydro-1,6-benzoxathiocine, etc.; benzodioxocine such as 2,3,4,5-tetrahydro-1,6-benzodioxocine, etc.; benzotrioxepine such as 1,3,5-benzotrioxepine, SH-1,3,4-benzotrioxepine, etc.; benzoxathiazepine such as 3,4-dihydro-1H-5,2,1-benzoxathiazepine, 3,4-dihydro-2H-5,1,2-benzoxathiazepine, 4,5-dihydro-3,1,4-benzoxathiazepine, 4,5-di hydro-3H-1,2,5-benzoxathiazepine, etc.; benzoxadiazepine such as 2,3,4,5-tetrahydro-1,3,4-benzoxadiazepine, etc.; benzothiadiazepine such as 2,3,4,5-benzothiadiazepine, etc.; benzotriazepine such as 2,3,4,5-tetrahydro-1H-1,2,5-benzotriazepine, etc.; benzoxathiepine such as 4,5-dihydro-1,3,2-benzoxathiepine, 4,5-dihydro-1H-2,3-benzoxathiepine, 3,4-dihydro-2H-1,5-benzoxathiepine, 4,5-dihydro-3H-1,2-benzoxathiepine, 4,5-dihydro-3H-2,1-benzoxathiepine, 2,3-dihydro-5H-1,4-benzoxathiepine, 2,3-dihydro-5H-4,1-benzoxathiepine, etc.; particularly, 2,3,4,5-tetrahydro-1H-3-benzazepine, 2,3,4,5-tetrahydro-1H-2-benzazepine, 2,3-dihydro-1H-indole, 2,3,4,5-tetrahydro-1,4-benzoxazepine, and the like.

Among these groups, preferred ones are exemplified by groups of the formula:

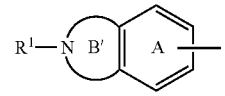

wherein ring B' is a 5- to 9-membered nitrogen-containing heterocycle which may further be substituted by oxo; the other symbols have the same meaning as mentioned above.

The "5- to 9-membered nitrogen-containing heterocycle" of said "5- to 9-membered nitrogen-containing heterocycle which may further be substituted by oxo" includes 5- to 9-membered nitrogen-containing heterocycles which may contain 1 to 3 heteroatoms selected from, for example, nitrogen, oxygen and sulfur, in addition to carbon atoms and one nitrogen atom. Preferably, 5- to 9-membered non-aromatic nitrogen-containing heterocycles (e.g., pyrrolidine, piperidine, hexamethyleneimine, heptamethyleneimine, piperazine, homopiperazine, tetrahydroxazepine, morpholine, thiomorpholine, etc.) may be used.

Among these heterocycles, particularly preferred ones are exemplified by groups of the formula:

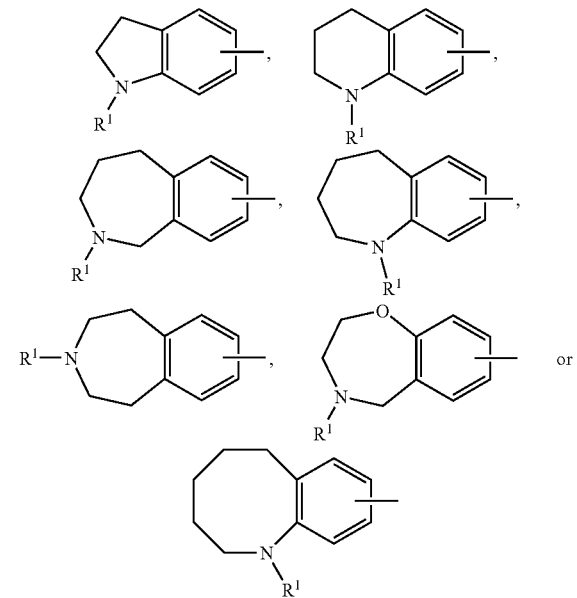

wherein $R^1$ has the same meaning as mentioned above.

Particularly preferred are the groups represented by the formula:

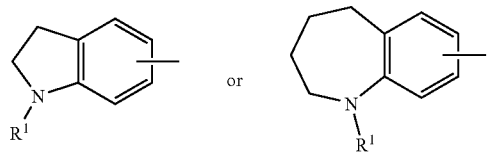

wherein $R^1$ has the same meaning as mentioned above.

When the phenyl of "optionally condensed phenyl which may have a substituent or substituents" in the above-mentioned item (2), is condensed with an optionally substituted bicyclic heterocycle or with two identical or different monocycles (provided that at least one of them is a monocyclic heterocycle), such groups are exemplified by those of formula:

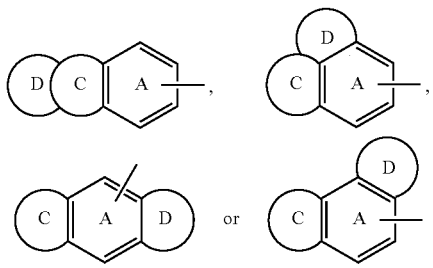

wherein the ring A has the same meaning as mentioned above; one of the rings C and D is an optionally substituted heterocycle and the other is an optionally substituted 5- to 9-membered ring.

As for the "heterocycle" of "optionally substituted heterocycle" represented by the ring C or D, those of "optionally substituted heterocycle" represented by ring B are exemplified.

The "5- to 9-membered ring" of "optionally substituted 5- to 9-membered ring" represented by the ring C or D may have 1 to 3 heteroatoms selected from nitrogen, oxygen and sulfur, and includes, for example, 5- to 9-membered heterocycles (e.g., pyridine, pyrazine, pyrimidine, imidazole, furan, thiophene, dihydropyridine, diazepine, oxazepine, pyrrolidine, piperidine, hexamethyleneimine, heptamethyleneimine, tetrahydrofuran, piperazine, homopiperazine, tetrahydroxazepine, morpholine, thiomorpholine, etc.), 5- to 9-membered carbocycles (e.g., benzene, cyclopentane, cyclopentene, cyclohexane, cyclohexene, cyclohexadiene, cycloheptane, cycloheptene, cycloheptadiene, etc.), and the like. Among them, those of the 5- to 7-membered rings are preferred. Benzene, cyclohexane, and the like are particularly preferred.

As for the "substituent" of "optionally substituted 5- to 9-membered ring", the same "substituent" as in "optionally substituted heterocycle" represented by the above-mentioned ring B may be exemplified.

The group of the above-mentioned formula:

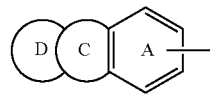

wherein each symbol has the same meaning as mentioned above includes groups derived from tricyclic condensed benzene rings by removing one hydrogen atom, which are exemplified by carbazole, 1,2,3,4,4a,9a-hexahydrocarbazole, 9,10-dihydroacridine, 1,2,3,4-tetrahydroacridine, 10,11-dihydro-5H-dibenz[b,f]azepine, 5,6,7,12-tetraydrodibenz[b,g]azocine, 6,11-dihydro-5H-dibenz[b,e]azepine, 6,7-dihydro-5H-dibenz[c,e]azepine, 5,6,11,12-tetrahydrodibenz[b,f]azocine, dibenzofuran, 9H-xanthene, 10,11-dihydrodibenz[b,f]oxepine, 6,11-dihydrodibenz[b,e]oxepine, 6,7-dihydro-5H-dibenz[b,g]oxocine, dibenzothiophene, 9H-thioxanthene, 10,11-dihydro-dibenzo[b,f]thiepine, 6,11-dihydrodibenzo[b,e]thiepine, 6,7-dihydro-5H-dibenz[b,g]thiocine, 10H-phenothiazine, 10H-phenoxazine, 5,10-dihydrophenazine, 10,11-dibenzo[b,f][1,4]thiazepine, 10,11-dihydrodibenz[b,f][1,4]oxazepine, 2,3,5,6,11,11a-hexahydro-1H-pyrrolo[2,1-b][3]benzazepine, 10,11-dihydro-5H-dibenzo[b,e][1,4]diazepine, 5,11-dihydrodibenz[b,e][1,4]oxazepine, 5,11-dihydrodibenzo[b,f][1,4]thiazepine, 10,11-dihydro-5H-dibenzo[b,e][1,4]diazepine, 1,2,3,3a,8,8a-hexahydropyrrolo[2,3-b]indole, and the like.

The group of the above-mentioned formula:

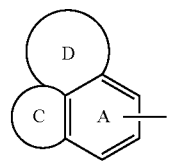

wherein each symbol has the same meaning as mentioned above
includes groups derived from tricyclic condensed benzene rings by removing one hydrogen atom, which are exemplified by 1H,3H-naphtho[1,8-cd][1,2]oxazine, naphtho[1,8-de]-1,3-oxazine, naphtho[1,8-de]-1,2-oxazine, 1,2,2a,3,4,5-hexahydrobenz[cd]indole, 2,3,3a,4,5,6-hexahydro-1H-benzo[de]quinoline, 4H-pyrrolo[3,2,1-ij]quinoline, 1,2,5,6-tetrahydro-4H-pyrrolo[3,2,1-ij]quinoline, 5,6-dihydro-4H-pyrrolo-[3,2,1-ij]quinoline, 1H,5H-benzo[ij]quinolizine, azepino[3,2,1-hj]indole, 1,2,4,5,6,7-hexahydroazepino[3,2,1-hi]indole, 1H-pyrido[3,2,1-jk][1]benzazepine, 5,6,7,8-tetrahydro-1H-pyrido[3,2,1-jk][1]benzazepine, 1,2,5,6,7,8-hexahydro-1H-pyrido[3,2,1-jk][1]benzazepine, 2,3-dihydro-1H-benz[de]isoquinoline, 1,2,3,4,4a,5,6,7-octahydronaphtho-[1,8-bc]azepine, 2,3,5,6,7,8-hexahydro-1H-pyrido[3,2,1-jk][1]benzazepine, and the like.

The group of the above-mentioned formula:

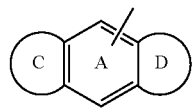

wherein each symbol has the same meaning as mentioned above
includes groups derived from tricyclic condensed benzene rings by removing one hydrogen atom, which are exemplified by 1,2,3,5,6,7-hexahydrobenzo[1,2-b:4,5-b']dipyrrole, 1,2,3,5,6,7-hexahydrocyclopent[f]indole, and the like.

The group of the above-mentioned formula:

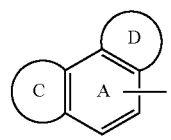

wherein each symbol has the same meaning as mentioned above
includes groups derived from tricyclic condensed benzene rings by removing one hydrogen atom, which are exemplified by 1,2,3,6,7,8-hexahydrocyclopent[e]indole, 2,3,4,7,8,9-hexahydro-1H-cyclopenta[f]quinoline, and the like.

Among these groups, preferred ones are exemplified by groups of formula:

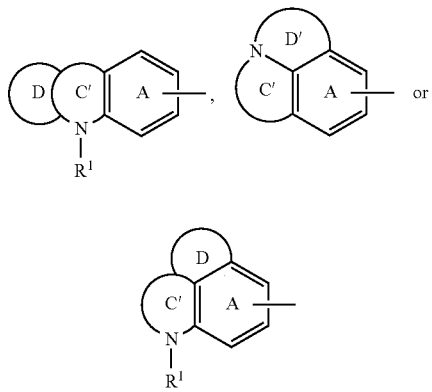

wherein the rings C' and D' each is a 5- to 9-membered nitrogen-containing heterocycle which may further be substituted by oxo; the other symbols have the same meaning as mentioned above.

Among them, groups of the formula:

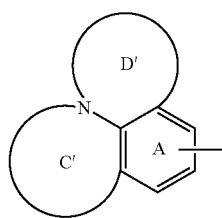

wherein each symbol has the same meaning as mentioned above are particularly preferred.

As for the "5- to 9-membered nitrogen-containing heterocycle which may further be substituted by oxo" represented by the ring C' or D', the same as in "5- to 9-membered nitrogen-containing heterocycle which may further be substituted by oxo" represented by the ring B' may be exemplified.

Among them, groups of formula:

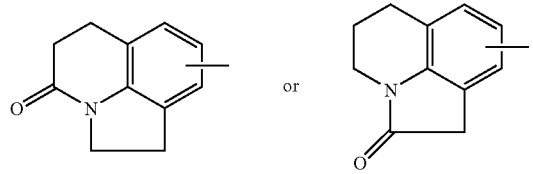

is particularly preferred.

When the phenyl group of "optionally condensed phenyl group which may have a substituent or substituents" in the above-mentioned item (3), is condensed with an optionally substituted tricyclic heterocycle, such groups are exemplified by those of formula:

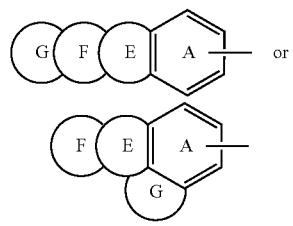

wherein ring A has the same meaning as mentioned above; at least one of rings E, F and G is an optionally substituted heterocycle and the other is an optionally substituted 5- to 9-membered ring.

The "optionally substituted heterocycle" and "optionally substituted 5- to 9-membered ring" represented by ring E, F or G are exemplified by "optionally substituted heterocycle" and "optionally substituted 5- to 9-membered ring" represented by ring B or C.

Among them, the followings are preferred:
(i) Groups of the formula:

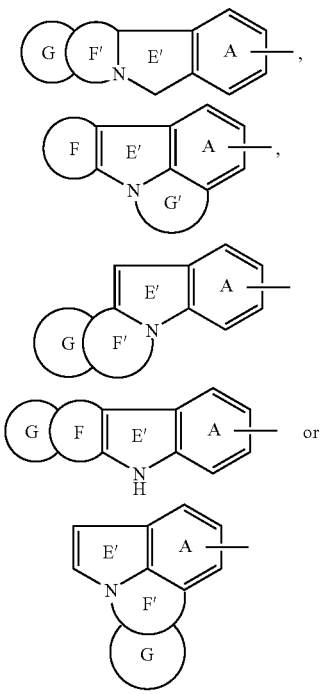

wherein ring A has the same meaning as mentioned above; the rings E', F' and G' each is a 5- to 9-membered nitrogen-containing heterocycle which may further be substituted by oxo; and --- indicates a single bond or double bond;

(ii) Groups derived from cyclic compounds by removing one hydrogen atom, which are exemplified by fluoranthene, acephenanthrylene, aceanthrylene, triphenylene, pyrene, chrysene, naphthacene, pleiadene, benzo[α]anthracene, indeno[1,2-a]indene, cyclopenta[α]phenanthrene, pyrido-[1',2':1,2]imidazo[4,5-b]quinoxaline, 1H-2-oxapyrene, spiro [piperidin-4,9'-xanthene], and the like; and their dihydro-, tetrahydro-, hexahydro-, octahydro-, decahydro-derivatives, etc.

As for the "5- to 9-membered nitrogen-containing heterocycle which may further be substituted by oxo" represented by ring E', F' or G', the same as in "5- to 9-membered nitrogen-containing heterocycle which may further be substituted by oxo" represented by ring B' may be exemplified.

The group of the above-mentioned formula:

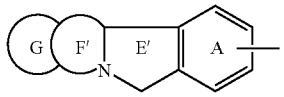

wherein each symbol has the same meaning as mentioned above,
includes the groups derived from tetracyclic condensed benzene rings by removing one hydrogen atom, which are exemplified by 2H-isoindolo[2,1-e]purine, 1H-pyrazolo[4',3':3,4]pyrido[2,1-a]isoindole, 1H-pyrido[2',3':4,5]imidazo[2,1-a]isoindole, 2H,6H-pyrido[1',2':3,4]imidazo[5,1-a]isoindole, 1H-isoindolo[2,1-a]benzimidazole, 1H-pyrido[3',4':4,5]pyrrolo[2,1-a]isoindole, 2H-pyrido[4', 3':4,5]pyrrolo[2,1-a]isoindole, 1H-isoindolo[2,1-a]indole, 2H-isoindolo[1,2-a]isoindole, 1H-cyclopenta[4,5]pyrimido[2,1-a]isoindole, 2H,4H-pyrano[4',3':4,5][1,3]oxazino[2,3-a]isoindole, 2H-isoindolo[2,1-a][3,1]benzoxazine, 7H-isoindolo-[1,2-b][1,3]benzoxazine, 2H-pyrido[2',1':3,4]pyrazino[2,1-a]isoindole, pyrido[2',3':4,5]pyrimido[2,1-a] isoindole, pyrido[3',2':5,6]pyrimido[2,1-a]isoindole, 1H-pyrido[1',2':3,4]pyrimido[2,1-a]isoindole, isoindolo[2,1-a]quinazoline, isoindolo[2,1-a]quinoxaline, isoindolo[1,2-a]isoquinoline, isoindolo[2,1-b]isoquinoline, isoindolo[2,1-a]quinoline, 6H-oxazino-[3',4':3,4][1,4]diazepino[2,1-a]isoindole, azepino[2',1':3,4]pyrazino[2,1-a]isoindole, 2H,6H-pyrido[2',1':3,4][1,4]diazepino[2,1-a]isoindole, 1H-isoindolo[1,2-b][1,3,4]benzotriazepine, 2H-isoindolo[2,1-a][1,3,4]benzotriazepine, isoindolo[2,1-d][1,4]benzoxazepine, 1H-isoindolo[2,1-b][2,4]-benzodiazepine, 1H-isoindolo[2,1-c][2,3]benzodiazepine, 2H-isoindolo[1,2-a][2,4]benzodiazepine, 2H-isoindolo[2,1-d]-[1,4]benzodiazepine, 5H-indolo[2,1-b][3]benzazepine, 2H-isoindolo[1,2-a][2]benzazepine, 2H-isoindolo[1,2-b][3]-benzazepine, 2H-isoindolo[2,1-b][2]benzazepine, 2H-isoindolo[1,2-b][1,3,4]benzoxadiazocine, isoindolo[2,1-b][1,2,6]benzotriazocine, 5H-4,8-methano-1H-[1,5]diazacyclo-undecino[1,11-a]indole, and the like.

The group of the above-mentioned formula:

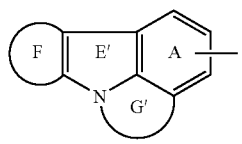

wherein each symbol has the same meaning as mentioned above,
includes groups derived from tetracyclic condensed benzene rings by removing one hydrogen atom, which are exemplified by 1H,4 μl-pyrrolo[3',2':4,5]pyrrolo[3,2,1-ij]quinoline, pyrrolo[3,2,1-jk]carbazole, 1H-furo[2',3':4,5]pyrrolo[3,2,1-ij]-quinoline, 1H,4H-cyclopenta[4, S]pyrrolo[1,2,3-de]quinoxaline, 1H,4H-cyclopenta[4,5]pyrrolo[3,2,1-ij]quinoline, pyrido[3',4':4,5]pyrrolo[1,2,3-de]benzoxazine, [1,4]oxazino[2,3,4-jk]carbazole, 1H,3H-[1,3]oxazino[5,4,3-jk]carbazole, pyrido[3',4':4,5]pyrrolo[1,2,3-de][1,4]benzothiazine, 4H-pyrrolo[3,2,1-de]phenanthridine, 4H, 5H-pyrido[3,2,1-de]phenanthridine, 1H,4H-3 a,6a-diazafluoroanthene, 1-oxa-4,6a-diazafluoroanthene, 4-oxa-2,10b-diazafluoroanthene, 1-thia-4,6a-diazafluoroanthene, 1H-pyrazino[3,2,1-jk]carbazole, 1H-indolo[3,2,1-de][1,5]naphthyridine, benzo[b]pyrano[2,3,4-hi]indolizine, 1H,3H-benzo[b]pyrano[3,4,5-hi]indolizine, 1H,4H-pyrano[2', 3':4,5]pyrrolo[3,2,1-ij]quinoline, 1H,3H-benzo[b]thiopyrano[3,4,5-hi]indolizine, 1H-pyrido[3,2,1-jk]carbazole, 4H-3-oxa-11b-azacyclohepta[jk]fluorene, 2H-azepino[1',2':1,2]pyrimidino[4,5-b]indole, 1H,4H-cyclohepta[4,5]pyrrolo[1,2,3-de]quinoxaline, 5H-pyrido[3',4':4,5]pyrrolo[1,2,3-ef][1,5]benzoxazepine, 4H-pyrido[3',4':4,5]pyrrolo[3,2,1-jk][4,1]benzothiazepine, 5H-pyrido[3',4':4,5]pyrrolo[1,2,3-ef][1,5]benzothiazepine, 5H-pyrido[4',3':4,5]pyrrolo[1,2,3-ef][1,5]benzothiazepine, [1,2,4]triazepino[6,5,4-jk]carbazole, [1,2,4]triazepino[6,7,1-jk]carbazole, [1,2,5]triazepino[3,4,5-jk]carbazole, 5H-[1,4]oxazepino-[2,3,4-jk]carbazole, 5H-[1,4]thiazepino[2,3,4-jk]carbazole, [1,4]diazepino[3,2,1-jk]carbazole, [1,4]diazepino[6,7,1-jk]carbazole, azepino[3,2,1-jk]carbazole, 1H-cyclooctaoyo[4,5]pyrrolo[1,2,3-de]quinoxaline, 1H-cycloocta[4,5]pyrrolo[3,2,1-ij]quinoline, and the like.

The group of the above-mentioned formula:

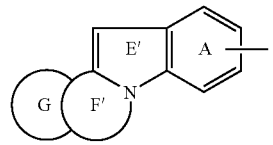

wherein each symbol has the same meaning as mentioned above,
includes the groups derived from tetracyclic condensed benzene rings by removing one hydrogen atom, which are exemplified by 1H-indolo[1,2-a]benzimidazole, 1H-indolo[1,2-b]indazole, pyrrolo[2', 1':3,4]pyrazino[1,2-a]indole, 1H,5H-pyrrolo[1',2':4,5]pyrazino[1,2-a]indole, 2H-pyrido[2',3':3,4]pyrrolo[1,2-a]indole, 1H-pyrrolo[2',3':3,4]pyrido[1,2-a]indole, 1H-indolo[1,2-a]indole, 6H-isoindolo[2,1-a]indole, 6H-indolo[1,2-c][1,3]benzoxazine, 1H-indolo[1,2-b][1,2]benzothiazine, pyrimido[4',5':4,5]pyrimido[1,6-a]indole, pyrazino[2',3':3,4]pyrrido[1,2-a]indole, 6H-pyrido[1',2':3,4]pyrimido[1,6-a]indole, indolo[1,2-b]cinnoline, indolo-[1,2-a]quinazoline, indolo[1,2-c]quinazoline, indolo[2,1-b]quinazoline, indolo[1,2-a]quinoxaline, indolo[1,2-a]-[1,8]naphthyridine, indolo[1,2-b]-2,6-naphthyridine, indolo[1,2-b][2,7]naphthyridine, indolo[1,2-h]-1,7-naph-thyridine, indolo[1,2-b]isoquinoline, indolo[1,2-a]isoquinoline, indolo[1,2-a]quinoline, 2H,6H-pyrido[2',1':3,4][1,4]diazepino[1,2-a]indole, 1H-indolo[2,1-c][1,4]benzodiazepine, 2H-indolo[1,2-d][1,4]benzodiazepine, 2H-indolo[2,1-a][2,3]benzodiazepine, 2H-indolo[2,1-b][1,3]benzodiazepine, 1H-indolo[1,2-b][2]benzazepine, 2H-indolo[1,2-a][1]benzazepine, 2H-indolo[2,1-a][2]benzazepine, indolo[1,2-e][1,5]benzodiazocine, indolo[2,1-b][3]benzazocine, and the like.

The group of the above-mentioned formula:

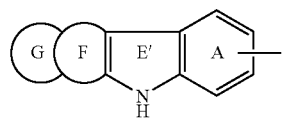

wherein each symbol has the same meaning as mentioned above
includes the groups derived from tetracyclic condensed benzene rings by removing one hydrogen atom, which are exemplified by 1H-imidazo[1',2':1,2]pyrido[3,4-b]indole, 1H-imidazo[1',2':1,6]pyrido[4,3-b]indole, 1H-imidazo[1',5':1,2]pyrido[3,4-b]indole, 1H-imidazo[1',5':1,6]pyrido[4,3-b]indole, 1H-imidazo-[2',1':2,3]pyrido[4,5-b]indole, imidazo[4,5-a]-carbazole, imidazo[4,5-c]carbazole, pyrazolo[3,4-c]carbazole, 2H-pyrazino[1',2':1,5]pyrrolo[2,3-b]indole, 1H-pyrrolo[1',2':1,2]pyrimido[4,5-b]indole, 1H-indolizino[6,7-b]indole, 1H-indolizino[8,7-b]indole, indolo[2,3-b]indole, indolo[3,2-b]indole, pyrrolo[2,3-a]carbazole, pyrrolo[2,3-b]carbazole, pyrrolo[2,3-c]carbazole, pyrrolo[3,2-a]carbazole, pyrrolo-[3,2-b]carbazole, pyrrolo[3,2-c]carbazole, pyrrolo[3,4-a]-carbazole, pyrrolo[3,4-b]carbazole, pyrrolo[3,4-c]carbazole, 1H-pyrido[3',4':4,5]furo[3,2-b]indole, 1H-furo[3,4-a]-carbazole, 1H-furo[3,4-b]carbazole, 1H-furo[3,4-c]carbazole, 2H-furo[2,3-a]carbazole, 2H-furo[2,3-c]carbazole, 2H-furo-[3,2-a]carbazole, 2H-furo[3,2-c]carbazole, 1H-pyrido[3',4':4,5]thieno[2,3-b]indole, thieno[3',2':5,6]thiopyrano[4,3-b]indole, thieno[3',4':5,6]thiopyrano[4,3-b]indole, 1H-[1]-benzothieno[2,3-b]indole, 1H-[1]-benzothieno[3,2-b]indole, 1H-thieno[3,4-a]carbazole, 2H-thieno[2,3-b]carbazole, 2H-thieno[3,2-a]carbazole, 2H-thieno[3,2-b]carbazole, cyclopenta[4,5]pyrrolo[2,3-f]quinoxaline, cyclopenta[5,6]pyrido[2,3-b]indole, pyrido[2',3':3,4]cyclopenta[1,2-b]indole, pyrido[2',3':4,5]cyclopenta[1,2-b]indole, pyrido[3',4':3,4]cyclopenta[1,2-b] indole, pyrido[3',4':4,5]cyclopenta[1,2-b]indole, pyrido[4',3':4,5]cyclopenta[1,2-b]indole, 1H-cyclopenta[5,6]pyrano[2,3-b]indole, 1H-cyclopenta[5,6]thio-pyrano[4,3-b] indole, cyclopenta[a]carbazole, cyclopenta[c]-carbazole, indeno[1,2-b]indole, indeno[2,1-b]indole, [1,2,4]triazino[4',3':1,2]pyrido[3,4-b]indole, 1,3,5-triazino[1',2':1,1]pyrido[3,4-b]indole, 1H-[1,4]oxazino-[4',3':1,2]pyrido[3,4-b]indole, 1H-[1,4]oxazino[4',3':1,6]-pyrido[3,4-b]indole, 4H-[1,3]oxazino[3',4':1,2]pyrido[3,4-b]indole, indolo[3,2-b][1,4]benzoxazine, 1,3-oxazino[6,5-b]carbazole, 2H-pyrimido[2',1':2,3][1,3]thiazino[5,6-b]indole, 2H-[1,3]thiazino[3',2':1,2]pyrido[3,4-b]indole, 4H-[1,3]thiazino[3',4':1,2]pyrido[3,4-b]indole, indolo[2,3-b][1,4]benzothiazine, indolo[3,2-b][1,4]benzothiazine, indolo[3,2-c][2,1]benzothiazine, 1,4-thiazino[2,3-a]carbazole, [1,4]-thiazino[2,3-b]carbazole, [1,4]thiazino[2,3-c]carbazole, 1,4-thiazino[3,2-b]carbazole, 1,4-thiazino[3,2-c]carbazole, 1H-indolo[2,3-g]pteridine, 1H-indolo[3,2-g]pteridine, pyrazino[1',2':1,2]pyrido[3,4-b]indole, pyrazino[1',2':1,2]pyrido[4,3-b]indole, 1H-pyrido[2',3':5,6]pyrazino[2,3-b]indole, 1H-pyrido[3',2':5,6]pyrazino[2,3-b]indole, 1H-pyrido[3',4':5,6]pyrazino[2,3-b]indole, pyrido[1',2':1,2]-pyrimido[4,5-b]indole, pyrido[1',2':1,2]pyrimido[5,4-b]-indole, pyrido[2',1':2,3]pyrimido[4,5-b]indole, pyrido-[1',2':1,2]pyrido[3,4-b]indole, pyrimido[1',2':1,6]pyrido-[3,4-b]indole, pyrimido[5',4':5,6]pyrano[2,3-b]indole, pyridazino[4',5':5,6]thiopyrano[4,5-b]indole, 1H-indolo-[3,2-c]cinnoline, 1H-indolo[2,3-b]quinoxaline, 1H-pyrazino-[2,3-a]carbazole, 1H-pyrazino[2,3-b]carbazole, 1H-pyrazino-[2,3-c]carbazole, 1H-pyridazino[3,4-c]carbazole, 1H-pyridazino[4,5-b]carbazole, 1H-pyrimido[4,5-a]carbazole, 1H-pyrimido[4,5-c]carbazole, 1H-pyrimido[5,4-a]carbazole, 1H-pyrimido[5,4-b]carbazole, 1H-pyrimido[5,4-c]carbazole, 7H-1,4-dioxino[2',3':5,6][1,2]dioxino[3,4-b]indole, 6H-[1,4]benzodioxino[2,3-b]indole, 6H-[1,4]benzodithiino[2,3-b]indole, 1H-indolo[2,3-b]-1,5-naphthyridine, 1H-indolo-[2,3-b][1,6]naphthyridine, 1H-indolo[2,3-b][1,8]naphthyridine, 1H-indolo[2,3-c]-1,5-naphthyridine, 1H-indolo[2,3-c][1,6]naphthyridine, 1H-indolo[2,3-c][1,7]naphthyridine, 1H-indolo[2,3-c][1,8]naphthyridine, 1H-indolo[3,2-b]-1,5-naphthyridine, 1H-, indolo[3,2-b][1,7]naphthyridine, 1H-indolo[3,2-b][1,8]naphthyridine, 1H-indolo[3,2-c][1,8]naphthyridine, indolo[2,3-a]quinolizine, indolo[2,3-b]quinolizine, indolo[3,2-a]quinolizine, indolo[3,2-b]quinolizine, pyrano[4', 3':5,6]pyrido[3,4-b]indole, pyrano[4',3':4,5]pyrano[3,2-b]indole, pyrido[4',3':5,6]pyrano[2,3-b]indole, pyrido[4',3':5,6]pyrano[3,4-b]indole, 1H-indolo[2,3-c]isoquinoline, 1H-indolo[3,2-c]isoquinoline, 1H-indolo[2,3-c]quinoline, 1H-indolo[3,2-c]quinoline, 1H-pyrido[2,3-a]carbazole, 1H-pyrido[2,3-b]carbazole, 1H-pyrido[2,3-c]carbazole, 1H-pyrido[3,2-a]carbazole, 1H-pyrido[3,2-b]carbazole, 1H-pyrido[3,2-c]carbazole, 1H-pyrido[3,4-a]carbazole, 1H-pyrido[3,4-b]carbazole, 1H-pyrido[3,4-c]carbazole, 1H-pyrido[4,3-a]carbazole, 1H-pyrido[4,3-b]carbazole, 1H-pyrido[4,3-c]carbazole, 1H-quindoline, 1H-quindoline, 1H-pyrano[3',4':5,6]pyrano[4,3-b]indole, [1]-benzopyrano[2,3-b]indole, [1]benzopyrano[3,2-b]indole, [1]-benzopyrano[3,4-b]indole, [1]benzopyrano[4,3-b]indole, [2]-benzopyrano[4,3-b]indole, pyrano[2,3-a]carbazole, pyrano[2,3-b]carbazole, pyrano[2,3-c]carbazole, pyrano[3,2-a]-carbazole, pyrano[3,2-c]carbazole, pyrano[3,4-a]carbazole, 1H-phosphinolino[4,3-b]indole, [1]benzothiopyrano[2,3-b]indole, [1]benzothiopyrano[3,2-b]indole, [1]benzothiopyrano[3,4-b]indole, [1]benzothiopyrano[4,3-b]indole, [2]benzothiopyrano[4,3-b]indole, 1H-benzo[a]carbazole, 1H-benzo[b]carbazole, 1H-benzo[c]carbazole, [1,6,2]oxathiazepino[2',3':1,2]pyrido[3,4-b]indole, 1H-azepino[1',2':1,2]pyrido[3,4-b]indole, 1H-pyrido[1',2':1,2]azepino[4,5-b]indole, 2H-pyrido[1',2':1,2]azepino[3,4-b]indole, 1H-pyrido[3',2':5,6]oxepino[3,2-b]indole, 1H-pyrido[4',3':5,6]oxepino[3,2-b]indole, 2H-pyrido[2',3':5,6]oxepino[2,3-b]indole, 2H-pyrido[2',3':5,6]oxepino[3,2-b]indole, 2H-pyrido-[3',4':5,6]oxepino[3,2-b]indole, pyrido[2',3':4,5]cyclohepta[1,2-b]indole, pyrido[3',2':3,4]cyclohepta[1,2-b]indole, pyrido[3',4':4,5]cyclohepta[1,2-b]indole, pyrido[3',4':5,6]cyclohepta[1,2-b]indole, 2H-pyrano[3',2':2,3]azepino[4,5-b]indole, 1H-indolo[3,2-b][1,5]benzoxazepine, 1H-indolo[3,2-d][1,2]benzoxazepine, 1H-indolo[2,3-c][1,5]benzothiazepine, [1,4]diazepino[2,3-a]carbazole, indolo[2,3-b][1,5]benzodiazepine, indolo[2,3-d][1,3]benzodiazepine, indolo[3,2-b][1,4]benzodiazepine, indolo[3,2-b][1,5]benzodiazepine, indolo[3,2-d][1,3]benzodiazepine, indolo[3,2-d][2,3]benzodiazepine, indolo[2,3-a][3]benzazepine, indolo[2,3-c][1]benzazepine, indolo[2,3-d][1]benzazepine, indolo[2,3-d][2]benzazepine, indolo[3,2-b][1]benzazepine, indolo[3,2-c][1]benzazepine, indolo[3,2-d][1]benzazepine, 1H-indolo[2,1-b][3]benzazepine, 1H-[1]benzoxepino[5,4-b]indole, 1H-[2]benzoxepino[4,3-b]indole, 1H-[1]benzothiepino[4,5-b]-indole, 1H-[1]benzothiepino[5,4-b]indole, benzo[3,4]cyclohepta[1,2-b]indole, benzo[4,5]cyclohepta[1,2-b]indole, benzo[5,6]cyclohepta[1,2-b]indole, benzo[6,7]cyclohepta[1,2-b]indole, cyclohepta[b]carbazole, 4H-[1,5]oxazocino[5',4':1,6]pyrido[3,4-b]indole, azocino[1',2':1,2]pyrido[3,4-b]indole, 2,6-methano-2H-azecino[4,3-b]indole, 3,7-methano-3H-azecino-[5,4-b]indole, pyrido[1',2':1,8]azocino[5,4-b]indole, pyrido-[4',3':6,7]oxocino[2,3-b]indole, pyrido-[4',3':6,7]oxocino[4,3-b]indole, 1,5-methano-1H-azecino[3,4-b]indole, 2,6-methano-1H-azecino[5,4-b]indole, 1H-pyrido[3',4':5,6]cycloocta[1,2-b]indole, 1,4-ethanooxocino[3,4-b]indole, pyrano[3',4':5,6]cycloocta[1,2-b]indole, 1H-indolo[2,3-c][1,2,5,6]benzotetrazocine, 1H-indolo[2,3-c][1,6]benzodiazocine, 6,13b-methano-13bH-azecino[5,4-b]indole, oxocino[3,2-a]carbazole, 1H-benzo[g]cycloocta[b]indole, 6,3-(iminomethano)-2H-1,4-thiazonino[9,8-b]indole, 1H,3H-[1,4]oxazonino[4',3':1,2]

pyrido[3,4-b]indole, 2H-3,6-ethanoazonino[5,4-b]indole, 2H-3,7-methanoazacycloundecino[5,4-b]indole, 1H-6,12b-ethanoazonino[5,4-b]indole, indolo[3,2-e][2]benzazonine, 5,9-methanoazacycloundecino[5,4-b]indole, 3,6-ethano-3H-azecino[5,4-b]indole, 3,7-methano-3H-azacycloundecino[5,4-b]indole, pyrano[4',3':8,9]azecino[5,4-b]-indole, 1H-indolo[2,3-c][1,7]benzodiazecine, 1H-indolo[3,2-e][2]benzazecine, benzo[e]pyrrolo[3,2-b]indole, benzo[e]pyrrolo[3,2-g]indole, benzo[e]pyrrolo[3,2,1-hi]indole, benzo[e]pyrrolo[3,4-b]indole, benzo[g]pyrrolo[3,4-b]indole, 1H-benzo[f]pyrrolo[1,2-a]indole, 1H-benzo[g]pyrrolo[1,2-a]indole, 2H-benzo[e]pyrrolo[1,2-a]indole, 1H-benzo[f]-pyrrolo[2,1-a]isoindole, 1H-benzo[g]pyrrolo[2,1-a]isoindole, 2H-benzo[e]pyrrolo[2,1-a]isoindole, isoindolo[6,7,1-cde]-indole, spiro[cyclohexane-1,5'-[5H]pyrrolo[2,1-a]isoindole], isoindolo[7,1,2-hij]quinoline, 7,11-methanoazocino[1,2-a]-indole, 7,11-methanoazocino[2,1-a]isoindole, dibenz[cd,f]-indole, dibenz[cd,g]indole, dibenz[d,f]indole, 1H-dibenz-[e,g]indole, 1H-dibenz[e,g]isoindole, naphtho[1,2,3-cd]-indole, naphtho[1,8-ef]indole, naphtho[1,8-fg]indole, naphtho[3,2,1-cd]indole, 1H-naphtho[1,2-e]indole, 1H-naphtho[1,2-f]indole, 1H-naphtho[1,2-g]indole, 1H-naphtho-[2,1-e]indole, 1H-naphtho[2,3-e]indole, 1H-naphtho[1,2-f]-isoindole, 1H-naphtho[2,3-e]isoindole, spiro[1H-carbazole-1,1'-cyclohexane], spiro[2H-carbazol-2,1'-cyclohexane], spiro[3H-carbazol-3,1'-cyclohexane], cyclohepta[4,5]pyrrolo[3,2-f]quinoline, cyclohepta[4,5]pyrrolo[3,2-h]quinoline, azepino[4,5-b]benz[e]indole, 1H-azepino[1,2-a]benz[f]indole, 1H-azepino[2,1-a]benz[f]isoindole, benzo[e]cyclohepta[b]-indole, benzo[g]cyclohepta[b]indole, and the like.

The group of the above-mentioned formula:

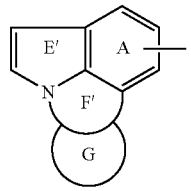

wherein each symbol has the same meaning as mentioned above,
includes groups derived from tetracyclic condensed benzene rings by removing one hydrogen atom, which are exemplified by 1H-dipyrrolo[2,3-b:3',2',1'-hi]indole, spiro[cyclopentane-1,2'(1'H)-pyrrolo[3,2,1-hi]indole], spiro[imidazolizine-4,1'(2'H)-1-[4H]pyrrolo[3,2,1-ij]quinoline], pyrido[2,3-b]pyrrolo[3,2,1-hi]indole, pyrido[4,3-b]pyrrolo[3,2,1-hi]indole, benzo[de]pyrrolo[3,2,1-ij]quinoline, 3H-pyrrolo[3,2,1-de]acridine, 1H-pyrrolo[3,2,1-de]phenanthridine, spiro[cyclohexane-1,6'-[6H]pyrrolo[3,2,1-ij]quinoline], 4,9-methanopyrrolo[3,2,1-lm][1]benzazocine, spiro[cycloheptane-1,6'-[6H]pyrrolo[3,2,1-ij]quinoline], 1H-pyrrano[3,4-d]pyrrolo[3,2,1-jk][1]benzazepine, 3H-benzo[b]pyrrolo[3,2,1-jk][4,l]benzoxazepine, 7H-indolo[1,7-ab][4,1]benzoxazepine, benzo[b]pyrrolo[3,2,1-jk][1,4]benzodiazepine, indolo[1,7-ab][1,4]benzodiazepine, indolo[1,7-ab][1]benzazepine, indolo[7,1-ab][3]benzazepine, 1H-cyclohepta[d][3,2,1-jk][1]benzazepine, spiro[azepino[3,2,1-hi]indole-7(4H), 1'-cycloheptane], 4H-5,11-methanopyrrolo[3,2,1-no][1]benzazacycloundecine, spiro[azepino[3,2,1-hi]indole-7(4H), 1'-cyclooctane], and the like.

Among them, particularly preferred is a group of the formula:

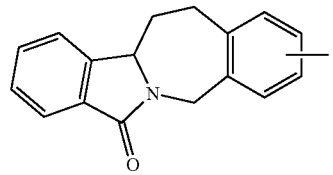

The "optionally condensed phenyl which may have a substituent or substituents" represented by Ar preferably includes, for example, optionally substituted groups of formula:

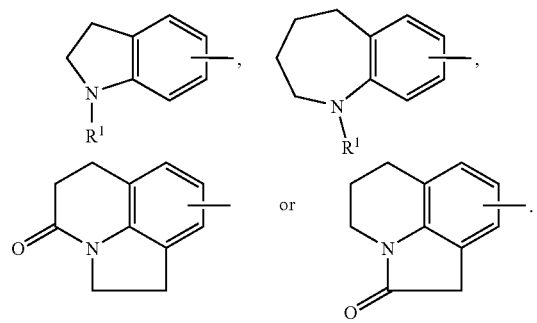

Particularly preferred is a group of formula:

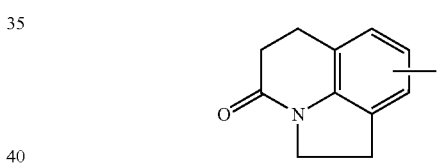

n is, preferably, an integer of 1 to 6. Particularly preferred are 2 to 6, and especially preferred is 2.

Each of R and R' is a hydrogen, halogen or optionally substituted hydrocarbon group, which may be different according to a repetition of n.

"Halogen" indicated by R and R' is exemplified by fluorine, chlorine, bromine, iodine, or the like, where fluorine is especially preferable.

As for the "optionally substituted hydrocarbon group" represented by R and R', the same as in "optionally substituted hydrocarbon group" represented by $R^1$ may be exemplified.

Each of R and R' is a hydrogen atom or fluorine, more preferably a hydrogen atom.

The "optionally substituted amino" represented by Y includes, for example, groups of the formula:

wherein $R^4$ and $R^5$ each is hydrogen, optionally substituted hydrocarbon group, or acyl.

As for the "optionally substituted hydrocarbon group" and "acyl" represented by $R^4$ and $R^5$, the same as in "optionally substituted hydrocarbon group" and "acyl" represented by $R^1$ may be exemplified.

The "nitrogen-containing saturated heterocyclic group" of "optionally substituted nitrogen-containing saturated heterocyclic group" represented by Y includes 5- to 9-membered (preferably, 5- to 7-membered) nitrogen-containing saturated heterocyclic group which may contain 1 to 3 heteroatoms selected from nitrogen, oxygen and sulfur, in addition to carbon atoms and one nitrogen atom. Such a group is exemplified, for example, by groups of the formula:

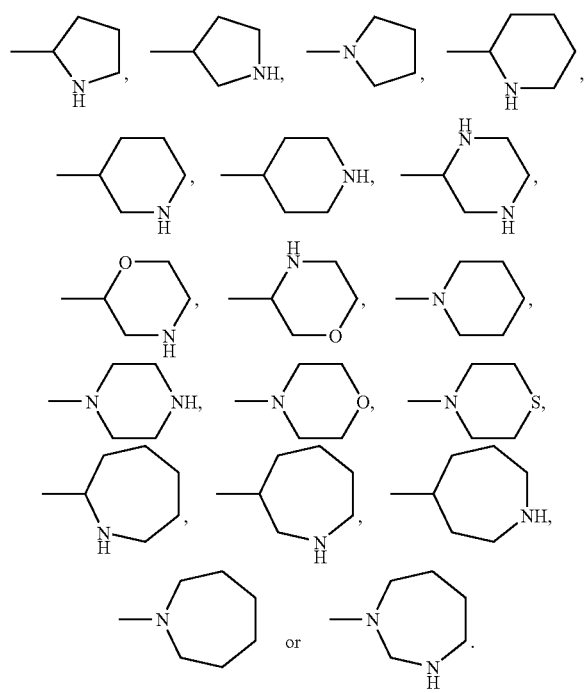

Among them, 6-membered cyclic groups are preferred. Particularly preferred is a group of formula:

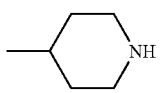

As for the "substituent" of "optionally substituted nitrogen-containing saturated heterocyclic group", the same "substituent" as in "heterocyclic group that may have substituents" represented by the above-mentioned ring B may be exemplified. The number of the substituent is 1 to 5. In addition, the nitrogen atom on the "nitrogen-containing saturated heterocyclic group" of "optionally substituted nitrogen-containing saturated heterocyclic group" may have the same group as those represented by the above-mentioned $R^1$.

Preferably, Y is a group of the formula:

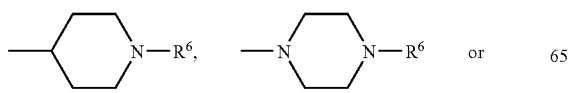

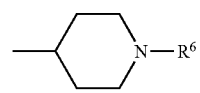

wherein $R^6$ has the same meaning as $R^1$.
Particularly preferred is a group of the formula:

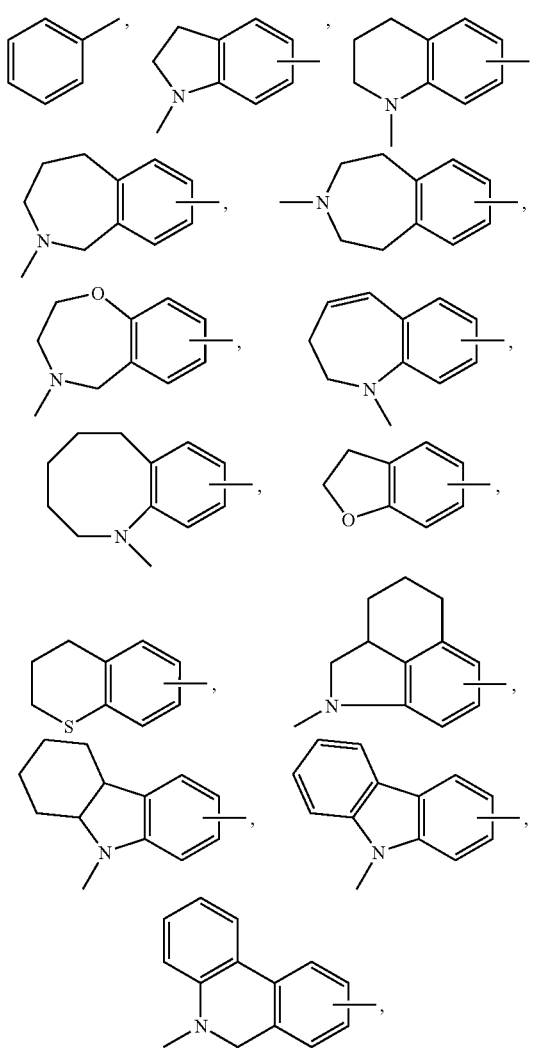

wherein $R^6$ has the same meaning as mentioned above.

$R^6$ is preferably hydrogen or optionally substituted hydrocarbon group. Particularly preferred are $C_{7-16}$ aralkyl (preferably, benzyl) and the like, which may be substituted by 1 to 3 substituents selected from halogen (preferably, fluoro, etc.), $C_{1-6}$ alkyl (preferably, methyl, etc.), $C_{1-6}$ alkoxy (preferably, methoxy, etc.), cyano, nitro and hydroxy.

Compound (I) preferably includes those in which Ar is a group of the formula:

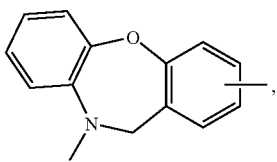

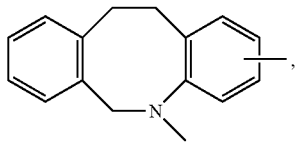

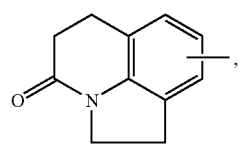

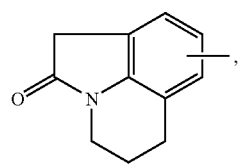

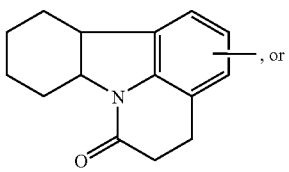, or

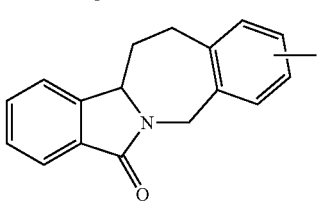

among which, when Ar is phenyl, it may be substituted by substituent(s) selected from (1) halogen (fluoro, etc.), (2) $C_{1-6}$ alkoxy(methoxy, etc.), (3) amino, (4) (mono- or di-) $C_{1-6}$ alkylamino (methylamino, ethylamino, dimethylamino, diethylamino, etc.), (5) pyrrolidino, (6) piperidino, (7) piperazino, (8) N-methylpiperazino, (9) N-acetylpiperazino, (10) morpholino, (11) hexamethylenimino, (12) imidazolyl, and (13) $C_{1-6}$ alkyl(propyl, etc.) which may be substituted by a carboxy optionally esterified by $C_{1-6}$ alkyl(methyl, etc.);

when Ar is condensed phenyl, its heterocyclic portion may be substituted by substituent(s) selected from (1) $C_{1-6}$ alkyl (methyl, ethyl, propyl, n-butyl, etc.), (2) $C_{7-16}$ aralkyl(benzyl, phenyethyl, etc.) which may be substituted by substituent(s) selected from halogen (fluoro, chloro, etc.), $C_{1-6}$ alkyl(methyl, etc.), $C_{1-6}$ alkoxy (methoxy, etc.) and nitro, (3) $C_{1-6}$ alkyl-carbonyl(acetyl, propionyl, isobutyryl, pivaloyl, etc.), (4) $C_{7-16}$ aralkyl-carbonyl(phenylacetyl, etc.), (5) $C_{6-14}$ aryl-carbonyl(benzoyl, etc.), (6) $C_{1-6}$ alkyl-carbonyl-$C_{6-14}$ aryl(methylbenzoyl, etc.), (7) $C_{1-6}$ alkoxy-carbonyl-$C_{6-14}$ aryl (methoxybenzoyl, etc.) and (8) pyridyl;

n is 2;

each of R and R' is the hydrogen atom or fluorine (more preferably the hydrogen atom);

in other words,
formula

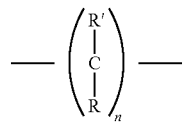

is —$CH_2CH_2$—, —$CHFCH_2$—, or —$CF_2CH_2$—;
Y is a group of the formula:

wherein the symbol has the same meaning as mentioned above;
wherein the symbol has the same meaning as mentioned above;
and $R^6$ is (1) hydrogen atom, (2) $C_{1-6}$ alkyl(methyl, ethyl, isopropyl, etc.) which may have substituent(s) selected from cyano, hydroxy, (mono- or di-)$C_{1-6}$ alkylamino (diethylamino, etc.), pyridyl, and carboxy optionally esterified (by $C_{1-6}$ alkyl (ethyl, etc.)), (3) $C_{7-16}$ aralkyl(benzyl, α-methylbenzyl, phenylethyl, etc.) which may be substituted by substituent(s) selected from halogen (fluoro, chloro, etc.), $C_{1-6}$ alkyl (methyl, t-butyl, etc.), halogeno $C_{1-6}$ alkyl(trifluoromethyl, etc.), hydroxy, $C_{1-4}$ alkoxy (methoxy, etc.), nitro, amino, cyano, carbamoyl, $C_{1-6}$ alkoxy optionally substituted by carboxy ($OCH_2CO_2H$, $OCH_2CO_2Et$, etc.) which may be esterified (by $C_{1-6}$ alkyl, etc.), carbamoyl optionally substituted by $C_{1-6}$ alkyl or amino optionally substituted by formyl (NHCHO, $NHCONH_2$, NHCONHMe, etc.), and $C_{1-3}$ alkylenedioxy(methylenedioxy, etc.), (4) $C_{1-6}$ alkyl(methyl, propyl, etc.) which may be substituted by carboxy optionally esterified (by $C_{1-6}$ alkyl(ethyl, etc.), etc.), or (5) $C_{1-4}$ alkyl-carbonyl(acetyl, etc.) optionally substituted by (mono- or di-)$C_{1-6}$ alkylamino (dimethylamino, etc.).

Particularly preferred Compound (I) includes those in which Ar is a group of the formula:

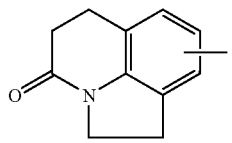

n is 2;
each of R and R' is the hydrogen atom or fluorine (more preferably the hydrogen atom);
in other words,
formula

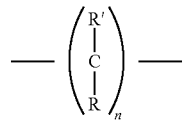

is —$CH_2CH_2$—, —$CHFCH_2$—, or —$CF_2CH_2$—;

Y is a group of the formula:

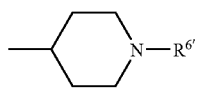

wherein $R^{6'}$ is benzyl which may be substituted by 1 or 2 substituents selected from halogen, $C_{1-3}$ alkyl, $C_{1-3}$ alkoxy, cyano, nitro and hydroxy.

Particularly preferred are:
8-[3-[1-[(3-fluorophenyl)methyl]-4-piperidinyl]-1-oxopropyl]-1,2,5,6-tetrahydro-4H-pyrrolo[3,2,1-ij]quinolin-4-one;
8-[3-[1-(phenyl methyl)-4-piperidinyl]-1-oxopropyl]-1,2,5,6-tetrahydro-4H-pyrrolo[3,2,1-ij]quinolin-4-one;
8-[3-[1-[(2-hydroxyphenyl)methyl]-4-piperidinyl]-1-oxopropyl]-1,2,5,6-tetrahydro-4H-pyrrolo[3,2,1-ij]quinolin-4-one; and
8-[2-fluoro-3-[1-[(3-fluorophenyl)methyl]-4-piperidinyl]-1-oxopropyl]-1,2,5,6-tetrahydro-4H-pyrrolo[3,2,1-ij]quinolin-4-one, or salts thereof,
wherein the crystals of the present invention are most preferable from the point of the stability and the effectiveness of the active ingredient.

Compounds (I) or salts thereof may be produced by a per se known process or its equivalent process. For example, the objective compounds of the above formula may be produced according to:

(1) the methods as described in JP-A 3-173867/1991 (EP-A 0378207) and JP-A 64-79151/1989 (EP-A 0296560), wherein the "optionally condensed phenyl which may have a substituent or substituents" represented by Ar does not form a condensed ring;

(2) the methods as described in JP-A 5-140149/1993 (EP-A 0487071), JP-A 6-166676/1994 (EP-A 0560235), IP-A 6-206875/1994 (EP-A 0567090), and JP-A 2-169569/1990 (U.S. Pat. No. 4,895,841), wherein the "optionally condensed phenyl which may have a substituent or substituents" represented by Ar is condensed with an optionally substituted monocyclic heterocycle;

(3) the methods as described in JP-A 7-206854/1995 (EP-A 0607864), wherein the "optionally condensed phenyl which may have a substituent or substituents" represented by Ar is condensed with an optionally substituted bicyclic heterocycle or with two identical or different monocyclic heterocycle (provided that at least one of two is a monocyclic heterocycle); and (4) the methods as described in JP-A 7-309835/1995 (EP-A0655451), wherein the "optionally condensed phenyl which may have a substituent or substituents" represented by Ar is condensed with an optionally substituted tricyclic heterocycle.

Salt

As for the salt of 8-[3-[1-[(3-fluorophenyl)methyl]-4-piperidinyl]-1-oxopropyl]-1,2,5,6-tetrahydro-4H-pyrrolo[3,2,1-ij]quinolin-4-one, a pharmacologically permissible salt is preferred, which is exemplified by a salt with an inorganic acid, a salt with an organic acid, or the like.

Preferable examples of a salt with an inorganic acid include, for example, salts with hydrochloric acid, hydrobromic acid, nitric acid, sulfuric acid, phosphoric acid, and the like.

Preferable examples of a salt with an organic acid include, for example, salts with formic acid, acetic acid, trifluoroacetic acid, fumaric acid, oxalic acid, tartaric acid, maleic acid, citric acid, methanesulfonic acid, benzenesulfonic acid, and the like.

Properties of Crystals

The crystals of the present invention are exemplified by crystals, which have the melting point of, for example, above 110° C. and exhibit a diffraction pattern by the powder X-ray crystal diffractometry, which possesses characteristic peaks at the spacing (the d value) of about 17.4, about 8.68, about 5.27, about 4.97, about 4.76, about 4.31, and about 3.85 angstrom. Preferably exemplified are crystals, which have the melting point of, for example, above about 113° C. to about 118° C. and exhibit a diffraction pattern by the powder X-ray crystal diffractometry, which possesses characteristic peaks at the spacing (the d value) of about 17.4, about 8.68, about 5.27, about 4.97, about 4.76, about 4.31, and about 3.85 angstrom.

The crystals of the present invention are high in the purity (purity: 99.9%), high in the quality, low in the hygroscopic property, and extremely excellent in the stability without being deteriorated upon a long-term storage under the usual conditions.

Process for Production of Crystals

The crystals of 8-[3-[1-[(3-fluorophenyl)methyl]-4-piperidinyl]-1-oxopropyl]-1,2,5,6-tetrahydro-4H-pyrrolo[3,2,1-ij]quinolin-4-one of the present invention (herein may be abbreviated as "the crystals of the present invention") can be produced by subjecting crystals of 8-[3-[1-[(3-fluorophenyl)methyl]-4-piperidinyl]-1-oxopropyl]-1,2,5,6-tetrahydro-4H-pyrrolo[3,2,1-ij]quinolin-4-one to crystallization by the well-known method.

Such a method for crystallization is exemplified by crystallization from a solution, crystallization from a vapor, and crystallization from a melt.

Examples of the method for said "crystallization from a solution" include the concentration method, the slow cooling method, the reaction method (the diffusion method or the electrolysis method), the hydrothermal formation method, the fluxing agent method, and the like. Examples of the solvent to be used include an aromatic hydrocarbon (for example, benzene, toluene, xylene, or the like), a halogenated hydrocarbon (for example, dichloromethane, chloroform, or the like), a saturated hydrocarbon (for example, hexane, heptane, cyclohexane, or the like), an ether (for example, diethyl ether, diisopropyl ether, tetrahydrofuran, dioxane, or the like), a nitrile (for example, acetonitrile or the like), a ketone (for example, acetone or the like), a sulfoxide (for example, dimethyl sulfoxide or the like), an acid amide (for example, N,N-dimethylformamide or the like), an ester (for example, ethyl acetate or the like), an alcohol (for example, methanol, ethanol, isopropyl alcohol, or the like), water, and the like. These solvents are used singly or by mixing two or more kinds of solvents in an adequate ratio (for example, 1:1 or 1:100).

The method for said "crystallization from a vapor" is exemplified by the evaporation method (the sealed tube method or the air stream method), the vapor phase reaction method, the chemical transportation method, or the like.

Examples of the method for said "crystallization from a melt" include the normal freezing method (the pulling up method, the temperature gradient method, or the Bridgman method), the zone melting method (the zone leveling method or the float zone method), the special growth method (the VLS method or the liquid-phase epitaxy method), and the like.

As for the method for analyzing the thus-obtained crystals, the crystal analysis by the X-ray diffraction method is general. Furthermore, the method for determining the orientation of the crystals is exemplified by the mechanical method, the optical method, or the like.

An amorphous form of 8-[3-[1-[(3-fluorophenyl)methyl]-4-piperidinyl]-1-oxopropyl]-1,2,5,6-tetrahydro-4H-pyrrolo[3,2,1-ij]quinolin-4-one or a salt thereof is a well-known substance, which can be produced, for example, according to the method described in Japanese Patent Kokai Publication No. 1995-206854 or a modification thereof. The crystals of the present invention can be obtained by application of the above-mentioned method for crystallization to this substance.

2) Compounds of the formula:

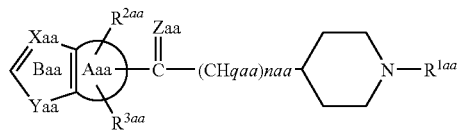

wherein one of the side chain containing C=Zaa, $R^{2aa}$ and $R^{3aa}$ is attached to the carbon atom indicated by an asterisk * on the ring Baa; the ring Aaa is benzo, thieno, pyrido, pyrazino, pyrimido, furano, seleno, pyrrolo, thiazolo or imidazolo; $R^{1aa}$ is phenyl, phenyl-$C_{1-6}$ alkyl, cinnamyl or heteroarylmethyl (where the heteroaryl includes imidazolo, thiazolo, thieno, pyrido or isoxazolo), and the phenyl and heteroaryl may be substituted by 1 or 2 substituents selected from $C_{1-6}$ alkyl, $C_{1-6}$ alkoxy and halogen; $R^{2aa}$ and $R^{3aa}$ each represent independently a hydrogen atom, $C_{1-6}$ alkoxy, $C_{1-6}$ alkyl optionally substituted by 1-3 fluorine atoms, benzyloxy, hydroxy, phenyl, benzyl, halogen, nitro, cyano, $COOR^{4aa}$, $CONHR^{4aa}$, $NR^{4aa}R^{5aa}$, $NR^{4aa}COR^{5aa}$ or $SOpaaCH_2Ph$ (where paa is 0, 1 or 2), or $R^{2aa}$ and $R^{3aa}$ taken with the adjacent carbon atoms may form a 5- or 6-membered ring (carbon, nitrogen and oxygen atoms constitute the ring), for example, methylenedioxy, ethylenedioxy or lactam ring; $R^{4aa}$ and $R^{5aa}$ each represent independently hydrogen or $C_{1-6}$ alkyl, or $R^{4aa}$ and $R^{5aa}$ in $NR^{4aa}R^{5aa}$ taken with the adjacent nitrogen atom may form a 4- to 8-membered ring containing at least one nitrogen atom (the other atoms constituting the ring are carbon, oxygen and nitrogen); in addition, $R^{4aa}$ and $R^{5aa}$ in $NR^{4aa}COR^{5aa}$ taken with the adjacent nitrogen atom and carbon atom may form a 4- to 8-membered lactam ring; Xaa is nitrogen or CH, and Yaa is oxygen, sulfur or $NR^{6aa}$; $R^{6aa}$ is hydrogen, $C_{1-6}$ alkyl, CO—$C_{1-6}$ alkyl or $SO_2$-phenyl (where the phenyl may be substituted by 1 to 5 substituents independently selected from $C_{1-4}$ alkyl); naa is an integer of 1 to 4; qaa each is independently 1 or 2; Zaa is oxygen or sulfur; or salts thereof. Such compounds are exemplified by 1-(2-methyl-1H-benzimidazol-5-yl)-3-[1-(phenyl methyl)-4-piperidinyl]-1-propanone, 1-(6-methylbenzo[b]thien-2-yl)-3-[1-(phenyl methyl)-4-piperidinyl]-1-propanone, 1-(6-methyl-indol-2-yl)-3-[1-(phenylmethyl)-4-piperidinyl]-1-propanone, and the like.

The above-mentioned compounds or salts thereof may be produced according to the process described in WO 93/07140 or its equivalent process.

3) Compounds of the formula:

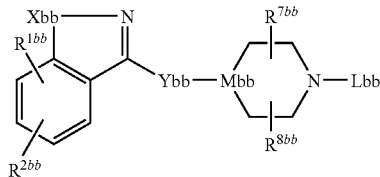

wherein $R^{1bb}$ and $R^{2bb}$ each is hydrogen, $C_{1-6}$ alkoxy, benzyloxy, phenoxy, hydroxy, phenyl, benzyl, halogen, nitro, cyano, group of the formula: $COR^{5bb}$, —$COOR^{5bb}$, —$CONHR^{5bb}$, $NR^{5bb}R^{6bb}$ or $NRbbCOR^{6bb}$ (where $R^{5bb}$ and $R^{6bb}$ each is i] hydrogen atom, ii]$C_{1-6}$ alkyl, iii]phenyl or benzyl which may be substituted by 1 or 2 substituents selected from halogen, $C_{1-4}$ alkyl, trifluoromethyl, $C_{1-4}$ alkoxy, cyano, nitro and hydroxy; or $R^{5bb}$ and $R^{6bb}$ in —$NR^{5bb}R^{6bb}$ taken together may form a 4- to 8-membered nitrogen-containing ring; $R^{5bb}$ and $R^{6bb}$ in —$NR^{5bb}COR^{6bb}$ taken together may form a 4- to 8-membered lactam ring), $C_{1-6}$ alkyl optionally substituted by 1 to 3 fluorine atoms, group of the formula: $SO_{pbb}CH_2$-phenyl or $SO_{pbb}C_{1-6}$ alkyl (where pbb is 0, 1 or 2), pyridylmethyloxy, thienylmethyloxy, 2-oxazolyl, 2-thiazolyl or benzenesulfonamido (said phenoxy, benzyloxy, phenyl, benzyl, benzenesulfonamido, pyridylmethyloxy, thienylmethyloxy, 2-oxazolyl, and 2-thiazolyl may be substituted by 1 or 2 substituents selected from halogen, $C_{1-6}$ alkyl, trifluoromethyl, $C_{1-6}$ alkoxy, cyano, nitro and hydroxy); or $R^{1bb}$ and $R^{2bb}$, when they are attached to the adjacent carbon atoms and when Xbb is oxygen, sulfur or $NR^{4bb}$ ($R^{4bb}$ is hydrogen or $C_{1-4}$ alkyl), taken with the attached carbon atoms may form a group of the formula:

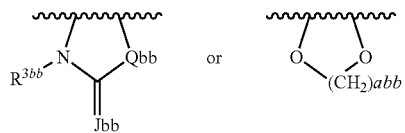

wherein Jbb is oxygen, sulfur or $NR^{4bb}$; abb is 1 or 2; $R^{3bb}$ is hydrogen or $C_{1-6}$ alkyl; Qbb is oxygen, sulfur, NH, $CHCH_3$, $C(CH_3)_2$, —CH=CH— or $(CH_2)_{1bb}$; and 1bb is an integer of 1 to 3;

Xbb is oxygen, sulfur, —CH=CH—, —CH=N—, —NH=CH—, —N=N— or $NR^{4bb}$ ($R^{4bb}$ has the same meaning as mentioned above);

Ybb is —$(CH_2)_{mbb}$—, —CH=CH$(CH_2)_{nbb}$—, —$NR^{4bb}$$(CH_2)_{mbb}$— or °$(CH_2)_{mbb}$— ($R^{4bb}$ has the same meaning as mentioned above; nbb is an integer of 0 to 3; mbb is an integer of 1 to 3);

Mbb is —CH— or nitrogen;

Lbb is i) phenyl or phenyl-$C_{1-6}$ alkyl which may be substituted by 1 to 3 substituents selected from halogen, $C_{1-6}$ alkyl, $C_{1-6}$ alkoxy, $C_{1-6}$ alkoxy-carbonyl and $C_{1-6}$ alkyl-carbonyl, ii) cinnamyl, iii) pyridylmethyl, or iv) group of the formula:

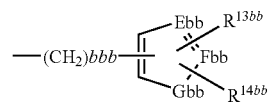

wherein bbb is an integer of 1 to 4; $R^{13bb}$ and $R^{14bb}$ each is hydrogen, $C_{1-4}$ alkyl, halogen or phenyl; Ebb and Fbb each is —CH— or nitrogen; Gbb is oxygen, sulfur or $NR^{4bb}$ ($R^{4bb}$ has the same meaning as mentioned above); provided that when both of Ebb and Fbb are nitrogen, then one of $R^{13bb}$ and $R^{14bb}$ is absent.

$R^{7bb}$ and $R^{8bb}$ each is hydrogen, $C_{1-6}$ alkyl, $C_{1-6}$ alkoxy-carbonyl, $C_{1-6}$ alkyl-carbonyl, or $C_{1-6}$ alkoxy; provided that said $C_{1-6}$ alkoxy is not attached to the carbon atom adjacent to the nitrogen]

or salts thereof. Such compounds are exemplified by 3-[2-[1-(phenylmethyl)-4-piperidinyl]ethyl]-5,6,8-trihydro-7H-isoxazolo[4,5-g]quinolin-7-one, 6,8-dihydro-3-[2-[1-(phenylmethyl)-4-piperidinyl]ethyl]-7H-pyrrolo[5,4-g]-1,2-benzisoxazol-7-one, 5,7-dihydro-3-[2-[1-(phenylmethyl)-4-piperidyl]ethyl]-6H-pyrrolo[5,4-f]-1,2-benzisoxazol-6-one, and the like.

The above-mentioned compounds or salts thereof may be produced according to the process described in PCT JP-A 6-500794/1994 (WO 92/17475) or its equivalent process.

4) Compounds of the formula:

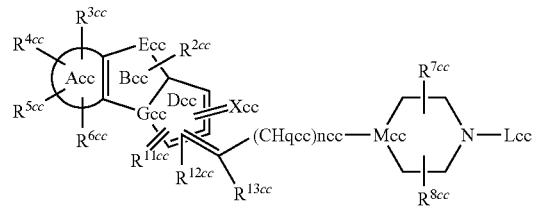

wherein ring Acc is benzo, thieno, pyrido, pyrazino, pyrimido, furano, seleno or pyrrolo;

$R^{2cc}$ is hydrogen, $C_{1-4}$ alkyl, benzyl, fluoro or cyano;

$R^{3cc}$, $R^{4cc}$, $R^{5cc}$ and $R^{6cc}$ each is hydrogen, $C_{1-6}$ alkoxy, benzyloxy, phenoxy, hydroxy, phenyl, benzyl, halogen, nitro, cyano, —$COOR^{9cc}$, —$CONHR^{9cc}$, $NR^{9cc}R^{10cc}$, —$NR^{9cc}COR^{10cc}$, or $C_{1-6}$ alkyl which may be substituted by 1 to 3 fluorine atoms; $SO_{pcc}CH_2$-phenyl (pcc is 0, 1 or 2), pyridylmethyloxy or thienylmethyloxy (said phenoxy, benzyloxy, phenyl, pyridylmethyloxy and thienylmethyloxy may be substituted by 1 or 2 substituents selected from halogen, $C_{1-4}$ alkyl, trifluoromethyl, $C_{1-4}$ alkoxy, cyano, nitro and hydroxy); or two of $R^{3cc}$, $R^{4cc}$, $R^{5cc}$ and $R^{6cc}$, taken with the adjacent carbon atoms, may form a saturated 5- or 6-membered ring (e.g., methylenedioxy, ethylenedioxy or lactam ring) in which each atom is carbon, nitrogen or oxygen in addition to the adjacent carbon atoms;

$R^{9cc}$ and $R^{10cc}$ each is hydrogen or $C_{1-6}$ alkyl; or $R^{9cc}$ and $R^{10cc}$ in $NR^{9cc}R^{10cc}$ (taken together may form a 4- to 8-membered cyclic amino in which one of the ring-constituting atoms is nitrogen and the others are carbon; or $R^{9cc}$ and $R^{10cc}$ in $NR^{9cc}COR^{10cc}$ taken together may form a 4- to 8-membered lactam ring;

Gcc is carbon or nitrogen;

Ecc is carbon, nitrogen, oxygen, sulfur, sulfoxide or sulfone;

≡≡≡ is a single bond or double bond;

the carbon located at any of the 1-, 2- or 3-position adjacent to a carbonyl group on the ring Dcc may be replaced by an appropriate nitrogen (to form a lactam ring as said carbon is located at the 1-, 2- or 3-position on the ring Dcc);

Xcc is O, S, $NOR^{1cc}$, hydrogen or $C_{1-6}$ alkyl (provided that a double bond is formed between Xcc and the ring Dcc, only when the atom on the ring Dcc to which Xcc is attached is carbon, and Xcc is O, S or $NOR^{1cc}$).

$R^{1cc}$ is hydrogen or $C_{1-6}$ alkyl;

qcc is 1 or 2;

when the ring Dcc is a lactam, ncc is an integer of 1 to 3, and when the ring Dcc is not lactam, ncc is 0 or an integer of 1 to 3;

Mcc is carbon or nitrogen;

Lcc is phenyl, phenyl-$C_{1-6}$ alkyl, cinnamyl or pyridylmethyl (said phenyl and phenyl-$C_{1-6}$ alkyl may be substituted by 1 to 3 substituents selected from $C_{1-6}$ alkyl, $C_{1-6}$ alkoxy, $C_{1-6}$ alkoxy-carbonyl, $C_{1-6}$ alkyl-carbonyl and halogen);

$R^{11cc}$ is hydrogen, halogen, hydroxy, $C_{1-4}$ alkyl, $C_{1-4}$ alkoxy or oxygen;

$R^{12cc}$ and $R^{13cc}$ each is hydrogen, fluoro, hydroxy, acetoxy, O-mesylate, O-tosylate, $C_{1-4}$ alkyl or $C_{1-4}$ alkoxy; or when both of $R^{12cc}$ and $R^{13cc}$ are attached to carbon atoms, they taken with the atoms to which they are attached may form a 3- to 5-membered ring in which the constituting atoms are carbon or oxygen;

$R^{7cc}$ and $R^{8cc}$ each is hydrogen, $C_{1-6}$ alkyl or $C_{1-6}$ alkoxy (said $C_{1-6}$ alkoxy is not bound to the carbon adjacent to the nitrogen, $C_{1-6}$ alkoxy-carbonyl and $C_{1-6}$ alkyl-carbonyl); or $R^{8cc}$ and $R^{12cc}$, taken with the atoms to which they are attached, may form a 4- to 7-membered saturated carboycle (one of the above-mentioned carbon atoms may be replaced by oxygen, nitrogen or sulfur);

provided that (a) when Ecc is carbon, nitrogen, oxygen, sulfur, sulfoxido or sulfone, Gcc is carbon; (b) when Gcc is nitrogen, Ecc is carbon or nitrogen; (c) when both of Ecc and Gcc are nitrogen, and when Gcc is carbon and Ecc is oxygen, sulfur, sulfoxido or sulfone, $R^{2cc}$ is absent; (d) the atoms located at the 1-, 2- and 3-positions on the ring Dcc each is not bound through more than one double bond; (e) when $R^{1cc}$ is oxygen, it is bound to the ring Dcc through a double bond, and when $R^{11cc}$ is other than oxygen, it is bound to the ring Dcc by a single bond; (f) when Xcc and $R^{11cc}$ both are oxygen and respectively bound to the carbon at the 1- and 3-positions or at the 3- and 1-positions on the ring Dcc, the carbon at the 2-position on the ring Dcc is replaced by nitrogen; and (g) Xcc is bound to the ring Dcc at the adjacent position at which a hydrocarbon group containing a group of the formula:

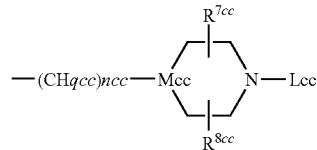

is attached, or salts thereof. Such compounds are exemplified by 2,3-dihydro-2-[[1-(phenylmethyl)-4-piperidinyl]methylene]-1H-pyrrolo[1,2-a]indol-1-one, 1,2,3,4-tetrahydro-4-methyl-2-[[1-(phenylmethyl)-4-piperidinyl]methylene]-cyclopent[b]-indol-3-one, 2,3-dihydro-2-[[1-(phenylmethyl)-4-piperidinyl]methyl]-1H-pyrrolo[1,2-a]benzimidazol-1-one, 1,2,3,4-tetrahydro-6-methyl-2-[([1-(phenylmethyl)-4-piperidinyl]-ethyl]pyrrolo[3,4-b]indol-3-one, and the like.

The above-mentioned compounds or salts thereof may be produced according to the process described in JP-A 4-234845/1992 (EP-A 441517) or its equivalent process.

5) Compounds of the formula:

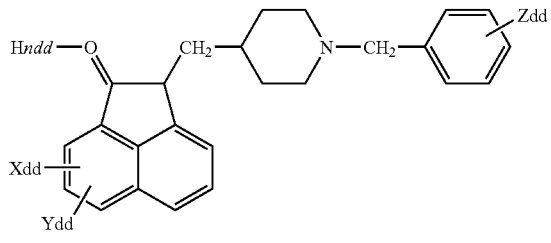

wherein Xdd is hydrogen, lower alkyl, lower alkoxy, hydroxy or nitro; Ydd is hydrogen or lower alkoxy; or Xdd and Ydd taken together form a group of —OCH$_2$O— (in this case each position of Xdd and Ydd attached on the benzene ring has to be adjacent each other); Zdd is hydrogen, lower alkyl, lower alkoxy, hydroxy, halogen or nitro; ndd is 0 or 1;

or salts thereof. Such compounds are exemplified by 2-[(N-benzylpiperidin-4-yl)methyl]-2a,3,4,5-tetrahydro-1(2H)-acenaphthylen-1-one, 2-[(N-(3-fluorobenzyl)piperidin-4-yl)methyl]-2a,3,4,5-tetrahydro-1(2H)-acenaphthylen-1-one, and the like.

The above-mentioned compounds or salts thereof may be produced according to the process described in JP-A 6-116237/1994 (EP-A 517221, U.S. Pat. No. 5,106,856) or its equivalent process.

6) Compounds of the forula:

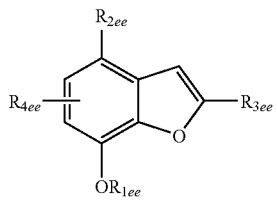

wherein $R_{1ee}$ is hydrogen, lower alkyl, aryl lower alkyl, CONHR$_{11ee}$ or CONR$_{6ee}$R$_{7ee}$;
$R_{2ee}$ is hydrogen, cyano, CH$_2$NR$_{8ee}$R$_{9ee}$, CONHR$_{5ee}$ or CONR$_{6ee}$R$_{7ee}$; $R_{3ee}$ is a group of the formula:

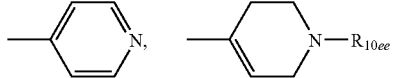

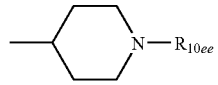

(where $R_{10ee}$ is hydrogen, lower alkyl, aryl lower alkyl, CONHR$_{5ee}$, CONR$_{6ee}$R$_{7ee}$, acyl, acyloxy lower alkyl or acyloxy-aryl lower alkyl); $R_{4ee}$ is hydrogen, halogen, lower alkyl or lower alkoxy; $R_{5ee}$ is hydrogen, lower alkyl or aryl lower alkyl; $R_{6ee}$ is lower alkyl or aryl lower alkyl; $R_{7ee}$ is lower alkyl or aryl lower alkyl; $R_{8ee}$ is hydrogen, lower alkyl, aryl lower alkyl or acyl; $R_{9ee}$ is hydrogen, lower alkyl or aryl lower alkyl; $R_{11ee}$ is lower alkyl, aryl or aryl lower alkyl; provided that when $R_{1ee}$ is hydrogen or lower alkyl, $R_{2ee}$ is not hydrogen;

or salts thereof. Such compounds are exemplified by 1-methyl-4-(4-cyano-7-methoxy-2-benzofuranyl)piperidine, 1-methyl-4-(4-N,N-diethylamido-7-methoxy-2-benzofuranyl)-piperidine, 1-methyl-4-(4-N,N-diethylaminomethyl-7-methoxy-2-benzofuranyl)piperidine, and the like.

The above-mentioned compounds or salts thereof may be produced according to the process described in JP-A 7-109275/1995 or its equivalent process.

7) Compounds of the formula:

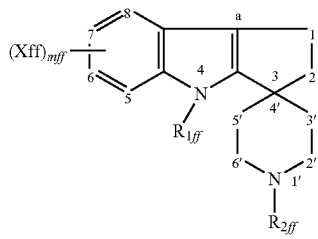

wherein Xff is hydrogen, halogen, lower alkoxy, lower alkyl, hydroxy or trifluoromethyl; mff is 1 or 2; $R_{1ff}$ is hydrogen or lower alkyl; $R_{2ff}$ is hydrogen, a group of the formula:

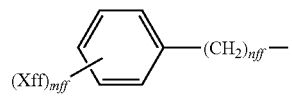

(wherein nff is 1 or 2; Xff and mff have the same meaning as mentioned above), a group of the formula:

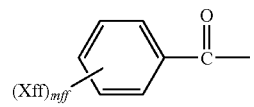

(wherein Xff and mff have the same meaning as mentioned above), or a group of the formula:

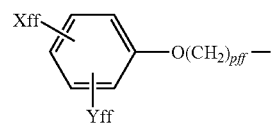

(wherein Xff has the same meaning as mentioned above; Yff is hydrogen or a group of the formula: COR$_{4ff}$ (where R$_{4ff}$ is hydrogen or lower alkyl); pff is 2 or 3);

or salts thereof. Such compounds are exemplified by 1,4-dihydro-7-methoxy-4-methyl-1'-phenylmethylspiro[cyclopent-[b]indole-3 (2H), 4'-piperidine], 1,4-dihydro-4-methyl-1'-(4-methoxyphenyl)methylspiro[cyclopent[b]indole-3 (2H), 4'-piperidine], and the like.

The above-mentioned compounds or salts thereof may be produced according to the process described in WO 97/37992 or its equivalent process.

8) Compounds of the formula:

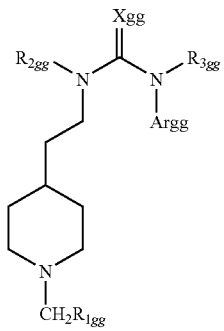

wherein $R_{1gg}$ is $C_{5-7}$ cycloalkyl, phenyl, or phenyl substituted by $C_{1-4}$ alkyl, $C_{1-4}$ alkoxy, nitro or halogen; $R_{2gg}$ and $R_{3gg}$ each is independently hydrogen or $C_{1-4}$ alkyl; $X_{gg}$ is sulfur, oxygen, CH—$NO_2$ or N—$R_{5gg}$, (where $R_{5gg}$ is hydrogen, hydroxy, $C_{1-4}$ alkoxy, $C_{1-4}$ alkyl, cyano or $C_{1-4}$ alkylsulfonyl; $A_{rgg}$ means a pyridyl or phenyl which may be substituted by 1 or more of substituents selected from halogen, $C_{1-4}$ alkyl, $C_{1-4}$ alkoxy, $C_{1-4}$ acyl, cyano, nitro, trifluoromethyl and trifluoromethoxy; or salts thereof. Such compounds are exemplified by N-phenyl-N'-[2-(1-benzyl-4-piperidyl)ethyl]-1,1-diamino-2-nitro-ethylene, 1-(2-pyridyl)-3-[2-(1-benzyl-4-piperidyl)ethyl]-thiourea, 1-phenyl-2-hydroxy-3-[2-(1-benzyl-4-piperidyl)-ethyl]guanidine, and the like.

The above-mentioned compounds or salts thereof may be produced according to the process described in JP-A 5-148228/1993 (EP-A 516520) or its equivalent process.

9) Compounds of the formula:

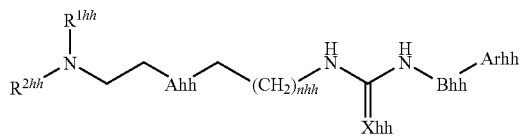

wherein $R^{1hh}$ is $C_{1-4}$ alkyl; $R^{2hh}$ is $C_{5-7}$ cycloalkyl, $C_{5-7}$ cycloalkyl-methyl, benzyl, or benzyl substituted by $C_{1-4}$ alkyl, $C_{1-4}$ alkoxy, halogen or nitro; $A_{hh}$ is oxygen or methylene; $B_{hh}$ is a direct bond, methylene or carbonyl; $A_{rhh}$ is pyridyl, a group of the following formula:

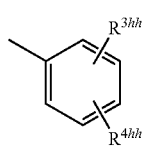

(wherein $R^{3hh}$ and $R^{4hh}$ each means independently hydrogen, halogen, nitro, $C_{1-4}$ alkyl, $C_{1-4}$ alkoxy, phenyl or trifluoromethoxy), oxofluorenyl of the following formula:

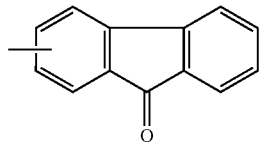

dioxoanthracenyl of the following formula:

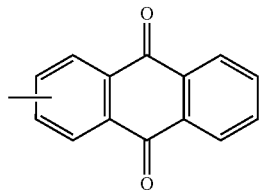

or naphthyl; $n_{hh}$ means 1 or 2; $X_{hh}$ means oxygen or sulfur; or salts thereof. Such compounds are exemplified by 1-[2-[2-(N-benzyl-N-methylamino)ethoxy]ethyl]-3-(3-nitrobenzoyl)thiourea, 1-[2-[2-(N-benzyl-N-methylamino)ethoxy]ethyl]-3-(9-oxo-2-fluorenoyl)thiourea, and the like.

The above-mentioned compounds or salts thereof may be produced according to the process described in JP-A 5-194359/1993 (EP-A 526313) or its equivalent process.

10) Compounds of the formula:

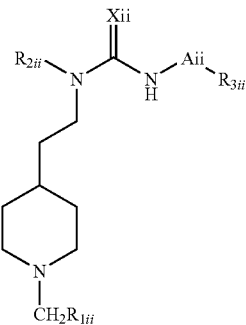

wherein $R_{1ii}$ is $C_{5-7}$ cycloalkyl, phenyl, or phenyl substituted by $C_{1-4}$ alkyl, $C_{1-4}$ alkoxy or halogen; $R_{2ii}$ is hydrogen or $C_{1-4}$ alkyl; $X_{ii}$ is oxygen or sulfur; $A_{ii}$ is methylene, carbonyl or sulfonyl; $R_{3ii}$ is (1) a group of the formula:

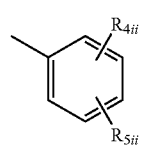

(wherein $R_{4ii}$ and $R_{5ii}$ each is independently hydrogen, halogen, nitro, $C_{1-4}$ alkyl, $C_{1-4}$ alkoxy, $C_{1-4}$ acyl, benzoyl, $C_{1-4}$ alkylsulfonyl or trifluoromethoxy, or $R_{4ii}$ and $R_{5ii}$ taken together may form methylenedioxy); (2) a group of the formula:

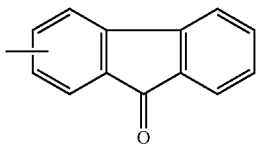

or (3) a group of the formula:

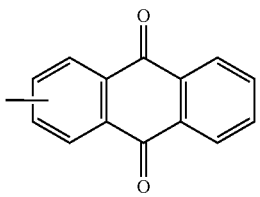

provided that when Xii is oxygen, Aii is a group other than methylene;
or salts thereof. Such compounds are exemplified by 1-(3-nitrobenzoyl)-3-[2-(1-benzyl-4-piperidyl)ethyl]thiourea, 1-(9,10-dioxo-2-anthracenoyl)-3-[2-(1-benzyl-4-piperidyl)-ethyl]thiourea, and the like.

The above-mentioned compounds or salts thereof may be produced according to the process described in PCT JP-A 6-507387/1994 (WO 92/14710) or its equivalent process.

11) Compounds of the formula:

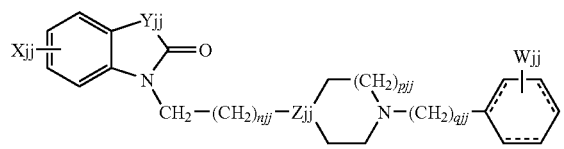

wherein njj is 1, 2 or 3; pjj is 1 or 2; qjj is 1 or 2; Xjj is independently a hydrogen atom, lower alkyl, aryl, aryloxy, CN, lower alkoxy, halogen, hydroxy, nitro, trifluoromethyl, alkylsulfonamido, NHCOR$_{jj}$ (where Rjj is lower alkyl or aryl), NR$_{1jj}$R$_{2jj}$ (where R$_{1jj}$ and R$_{2jj}$ each is independently hydrogen or lower alkyl, or they taken together may form a ring), CO$_2$R$_{jj}$ (where R$_{jj}$ is lower alkyl), or in some cases one or more of substituents selected from further lower alkyl-substituted cycloalkyl, cycloalkenyl and bicycloalkyl; Yjj is CO or CR$_{3jj}$R$_{4jj}$ (where R$_{3jj}$ and R$_{4jj}$ each is independently a hydrogen atom, lower alkyl or lower alkoxy, or they taken together form a cyclic acetal); Zjj is N or CH; and the group of the formula:

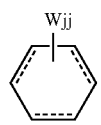

is in some cases a substituted phenyl or cyclohexyl (where Wjj is independently one or more of substituents selected from hydrogen atom, lower alkyl, lower alkoxy and halogen); (provided that the following compounds are excluded: compounds in which njj=1, pjj=1, qjj=1, Xjj=H, Yjj=CO, Zjj=N, and the group of the formula:

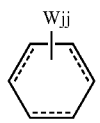

is an unsubstituted phenyl; and compound in which njj=2, pjj=1, qjj=1, Xjj=H, Yjj=CO, Zjj=N, and the group of the formula:

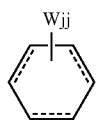

is 4-chlorophenyl);
or stereoisomers, optical isomers or racemates thereof, or their salts. Such compounds are exemplified by 5-cyclohexyl-1,3-dihydro-1-[2-[1-(phenylmethyl)-4-piperidinyl]ethyl]-2H-indol-2-one, and the like.

The above-mentioned compounds or salts thereof may be produced according to the process described in PCT JP-A 7-502272/1995 (WO 93/12085) or its equivalent process.

12) Compounds of the formula:

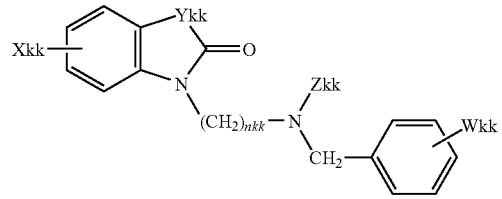

wherein nkk is 3, 4, 5, 6 or 7; Xkk is independently a hydrogen atom, lower alkyl, aryl, lower alkoxy, halogen, trifluoromethyl, nitro, —NHCOR$_{kk}$ (where R$_{kk}$ is lower alkyl or aryl), —NR$_{1kk}$R$_{2kk}$ (where R$_{1kk}$ and R$_{2kk}$ each is independently hydrogen or lower alkyl, or they taken together form a ring), or in some cases one or more of substituents selected from further lower alkyl-substituted cycloalkyl, cycloalkenyl and bicycloalkyl; Ykk is CO or CR$_{3kk}$R$_{4kk}$ (where R$_{3kk}$ and R$_{4kk}$ each is independently a hydrogen atom, lower alkyl or lower alkoxy, or they taken together form a cyclic acetal); Zkk is lower alkyl; and Wkk is one or more of substituents selected from hydrogen atom, lower alkyl, lower alkoxy and halogen;
or stereoisomers, optical isomers or racemates thereof, or their salts. Such compounds are exemplified by 5-cyclohexyl-1,3-dihydro-1-[5-(N-ethyl-N-phenyl methylamino)pentyl]-2H-indol-2-one, 5-cyclohexyl-1-[5-(N-ethyl-N-phenylmethylamino)-pentyl]-1H-indole-2,3-dione, and the like.

The above-mentioned compounds or salts thereof may be produced according to the process described in PCT JP-A 8-511515/1996 (WO 94/29272) or its equivalent process.

13) Compounds of the formula (III):

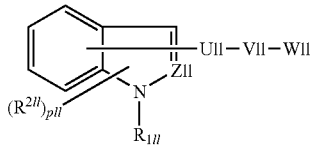

(III)

wherein $R_{1ll}$ and $R_{2ll}$ each is hydrogen, a group selected from the following substituent group All, or aryl, aralkyl, aralkyloxycarbonyl, arylamino, arylamino-alkyl, heterocyclic group, heterocyclic alkyl or heterocyclic aminoalkyl which may respectively be substituted by 1 to 3 (same or different) substituents selected from the following substituent group All; pll is an integer of 1 to 3; Ull is a group of the formula: —CO— or —CH(OR$_{3ll}$)- (where R$_{3ll}$ is hydrogen or hydroxy-protecting group); Vll is a group of the formula: —(CH=CH)mll-(CH$_2$)nll- (where mll is an integer of 0 to 2; nll is an integer of 0 to 7; provided that mll and nll are not 0 concurrently); Wll is a nitrogen-containing heterocyclic group which has an attaching point with Vll on the endocyclic nitrogen atom, a group of the formula (2ll):

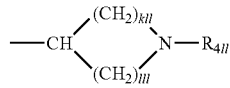

(2ll)

wherein kll and lll are the same or different representing 1 to 4; R$_{4ll}$ has the same meaning as in R$_{5ll}$ and R$_{6ll}$ as mentioned below, or, in the above-mentioned general formula (2ll), when the cyclic alkylene forms a 5- or 6-membered ring, a group in which said ethylene of the 5- or 6-membered ring is condensed with 1 or 2 benzene rings, or a group of the formula: —NR$_{5ll}$R$_{6ll}$ (where R$_{5ll}$ and R$_{6ll}$ each is hydrogen, a group selected from the following substituent group All, or an aryl, arylcarbonyl, aralkyl, heterocyclic or heterocyclic alkyl which may be substituted by 1 to 3 substituents selected from the following substituent group All);

The substituent group All is: Lower alkyl, cycloalkyl, aryl, heterocyclic group, aralkyl, halogen, amino, lower alkylamino, arylamino, amino lower alkyl, lower alkylaminoalkyl, lower alkynylaminoalkyl, nitro, cyano, sulfonyl, lower alkylsulfonyl, halogenoalkylsulfonyl, lower alkanoyl, arylcarbonyl, arylalkanoyl, lower alkoxy, lower alkoxycarbonyl, halogeno-lower alkyl, N-lower alkynyl, N-cyanoamino, N-lower alkynyl and N-methylaminomethyl;

or salts thereof. Such compounds are exemplified by 1-methyl-3-[3-(1-benzyl-4-piperidyl)propionyl]indole, 1-methyl-3-[3-[1-(3-fluorobenzyl)-4-piperidyl]propionyl]-5-fluoroindole, 1-methyl-3-[3-[1-(2-chlorobenzyl)-4-piperidyl]propionyl]-indazole, and the like.

The above-mentioned compounds or salts thereof may be produced according to the process described in JP-A 6-41070/1994 (EP-A 562832) or its equivalent process.

14) Compounds of the formula:

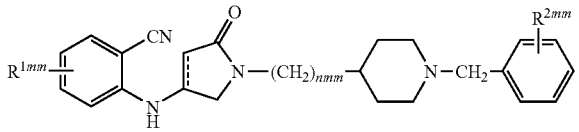

wherein $R^{1mm}$ is hydrogen, halogen, alkyl, alkoxy or alkylthio; $R^{2mm}$ is hydrogen, halogen, alkyl or alkoxy; nmm is an integer of 0-7; the broken line indicates the optional presence of a double bond;

or salts thereof. Such compounds are exemplified by N-[1-[4-(1-benzylpiperidyl)ethyl]-2-oxo-3-pyrrolin-4-yl]-2-aminobenzonitrile, N-[1-[4-(1-benzylpiperidyl)propyl]-2-oxo-3-pyrrolin-4-yl]-2-aminobenzonitrile, and the like.

The above-mentioned compounds or salts thereof may be produced according to the process described in JP-A 5-9188/1993 or its equivalent process.

15) Compounds of the formula:

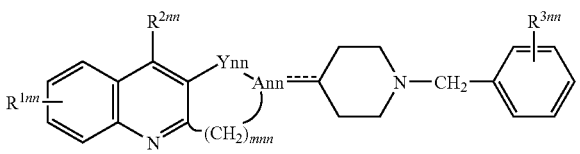

wherein >Ann $\equiv$ represents >N—(CH$_2$)nnn-, >C=, >C=CH(CH$_2$)nnn- or >CH(CH$_2$)nnn-(where nnn is an integer of 0-7); Ynn is >C=O or >CHOH; $R^{1nn}$ is hydrogen, halogen, alkyl, alkoxy or alkylthio; $R^{2nn}$ is hydrogen, halogen, hydroxy, alkyl, alkoxy, optionally substituted phenyl, phenoxy, alkanoyl or optionally substituted amino; $R^{3nn}$ is hydrogen, halogen, alkyl or alkoxy; mnn is an integer of 1-3; or salts thereof. Such compounds are exemplified by 9-amino-2-[4-(1-benzylpiperidyl)ethyl]-2,3-dihydropyrrolo[3,4-b]-quinolin-1-one, 9-amino-2-[2-(1-benzylpiperidin-4-yl)ethyl]-1,2,3,4-tetrahydroacridin-1-one, 9-methoxy-2-[4-(1-benzyl-piperidyl)ethyl]-2,3-dihydropyrrolo[3,4-b]quinoline-1-one, and the like.

The above-mentioned compounds or salts thereof may be produced according to the process described in JP-A 5-279355/1993 (EP-A 481-429) or its equivalent process.

16) Compounds of the formula:

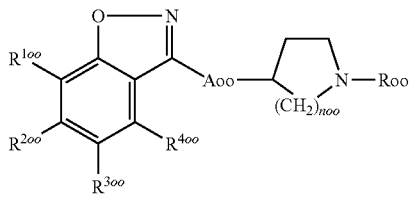

wherein $R_{oo}$ is hydrogen, alkyl, alkenyl, cycloalkylalkyl, phenylalkyl, naphthylalkyl, cycloalkylalkenyl, phenylalkenyl or naphthylalkenyl; $R^{1oo}$, $R^{2oo}$, $R^{3oo}$ and $R^{4oo}$ are the same or different each representing hydrogen atom, halogen, alkyl, phenyl, phenyl-alkyl, alkoxy, heteroaryl, heteroarylalkyl, phenylalkoxy, phenoxy, heteroarylalkoxy, heteroaryloxy, acyl, acyloxy, hydroxy, nitro, cyano, —NHCOR$^{5oo}$, —S(O)$_{moo}$R$^{5oo}$, —NHSO$_2$R$^{5oo}$, —CONR$^{6oo}$R$^{7oo}$, —NR$^{6oo}$R$^{7oo}$, —OCONR$^{6oo}$R$^{7oo}$, —OCSNR$^{6oo}$R$^{7oo}$, —SO$_2$NR$^{6oo}$R$^{7oo}$ or —COOR$^{8oo}$; or R$^{1oo}$, R$^{2oo}$, R$^{3oo}$ and R$^{4oo}$ are taken together, when they are adjacent each other, to form an optionally substituted —O(CH$_2$)poo-, —O(CH$_2$)qooO—, —O(CH$_2$)rooN(R$^{9oo}$)—, —O(CH$_2$)soo-CON(R$^{9oo}$)—, —N(R$^{9oo}$)CO—CH═CH— or a group forming benzene ring or heteroaromatic ring (where R$^{5oo}$ is alkyl, phenyl or phenylalkyl; R$^{6oo}$ and R$^{7oo}$ are the same or different each representing a hydrogen atom, alkyl, phenyl or phenylalkyl, or they taken with the adjacent nitrogen atom may form a heterocycle; R$^{8oo}$ is alkyl, phenyl or phenylalkyl; R$^{9oo}$ is hydrogen, alkyl, phenylalkyl or acyl; moo is 0, 1 or 2; poo, qoo, roo and soo are the same or different representing 1, 2 or 3); Aoo is a straight or branched chain alkylene; noo is 1, 2 or 3; in the above-mentioned definition, the alkyl, alkenyl, alkoxy, phenyl, phenoxy, cycloalkylalkyl, phenylalkyl, naphthylalkyl, cycloalkylalkenyl, phenylalkenyl, naphthylalkenyl, phenylalkoxy, heteroaryl, heteroaryloxy, heteroarylalkyl, heteroarylalkoxy, benzene ring and heteroaromatic ring may be substituted by 1 to 3 substituents selected from halogen, alkyl, alkoxy, acyl, acyloxy, hydroxy, nitro, cyano, COR$^{5oo}$, —S(O)$_{moo}$R$^{5oo}$, —NHSO$_2$R$^{5oo}$, —CONR$^{6oo}$R$^{7oo}$, —NR$^{6oo}$R$^{7oo}$, —OCONR$^{6oo}$R$^{7oo}$, —OCSNR$^{6oo}$R$^{7oo}$, —SO$_2$NR$^{6oo}$R$^{7oo}$ or —COOR$^{8oo}$; (where R$^{5oo}$, R$^{6oo}$, R$^{7oo}$, R$^{8oo}$ and moo have the same meaning as mentioned above); or salts thereof. Such compounds are exemplified by 3-[2-(1-benzyl-4-piperidyl)ethyl]-6,7-dimethoxy-1,2-benzisoxazole, 3-[2-(1-benzyl-4-piperidyl)ethyl]-6-(N-methyl-acetamino)-1,2-benzisoxazole, and the like.

The above-mentioned compounds or salts thereof may be produced according to the process described in JP-A 5-320160/1993 (WO 93/04063) or its equivalent process.

17) Compounds of the formula:

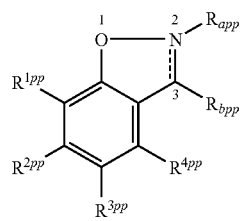

wherein when the bond between the 2- and 3-positions is a single bond, R$_{app}$ represents a group of the formula:

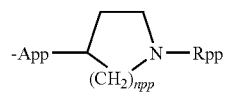

wherein Rpp is hydrogen, alkyl, alkenyl, cycloalkyl-alkyl, cycloalkylalkenyl, phenylalkyl, phenylalkenyl, naphthylalkyl or naphthylalkenyl; App is straight or branched chain alkylene; npp is 1, 2 or 3, and R$_{bpp}$ is oxygen; when the bond between the 2- and 3-positions is a double bond, then R$_{app}$ is absent, R$_{bpp}$ represents a group of the formula:

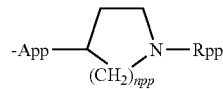

wherein each symbol has the same meaning as mentioned above, or a group of the formula:

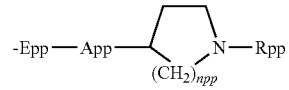

wherein Epp is oxygen or sulfur, and the other symbols have the same meaning as mentioned above; R$^{1pp}$, R$^{2pp}$, R$^{3pp}$ and R$^{4pp}$ are the same or different each representing hydrogen, halogen, alkyl, alkoxy, phenyl, phenylalkyl, phenylalkoxy, phenoxy, heteroaryl, heteroarylalkyl, heteroarylalkoxy, heteroaryloxy, acyl, acyloxy, hydroxy, nitro, cyano, —NHCOR$^{5pp}$, —S(O)$_{mpp}$R$^{5pp}$, —NHSO$_2$R$^{5pp}$, —CONR$^{6pp}$R$^{7pp}$, —NR$^{6pp}$R$^{7pp}$, —OCSNR$^{6pp}$R$^{7pp}$, —SO$_2$NR$^{6pp}$R$^{7pp}$ or —COOR$^{8pp}$ (where R$^{5pp}$ is alkyl, phenyl or phenylalkyl; R$^{6pp}$ and R$^{7pp}$ are the same or different each representing hydrogen, alkyl, phenyl or phenylalkyl, or they taken together with the adjacent nitrogen atom form a heterocycle; R$^{8pp}$ is hydrogen, alkyl, phenyl or phenylalkyl; mpp is 0, 1 or 2; in the above-mentioned definition, the alkyl, alkenyl, alkoxy, phenyl, phenylalkyl, phenylalkenyl, phenylalkoxy, phenoxy, cycloalkylalkyl, cycloalkylalkenyl, naphthylalkyl, naphthylalkenyl, heteroaryl, heteroarylalkyl, heteroarylalkoxy and heteroaryloxy may be substituted by 1 to 3 substituents selected from halogen, alkyl, alkoxy, acyl, acyloxy, hydroxy, nitro, cyano, —NHCOR$^{5pp}$, —S(O)$_{mpp}$R$^{5pp}$, —NHSO$_2$R$^{5pp}$, —CONR$^{6pp}$R$^{7pp}$, —NR$^{6pp}$R$^{7pp}$, —OCONR$^{6pp}$R$^{7pp}$, —OCSNR$^{6pp}$R$^{7pp}$, —SO$_2$NR$^{6pp}$R$^{7pp}$ or —COOR$^{8pp}$; (where R$^{5pp}$, R$^{6pp}$, R$^{7pp}$, R$^{8pp}$ and mpp have the same meaning as mentioned above);

or salts thereof. Such compounds are exemplified by 3-[2-(1-benzyl-4-piperidyl)ethyl]-6,7-dimethoxy-1,2-benzisoxazole, 6-benzoylamino-2-[3-(1-benzyl-4-piperidyl)propyl]-1,2-benzisoxazol-3(2H)-one, 6-benzoylamino-2-[2-(1-benzyl-4-piperidyl)ethyl]-1,2-benzisoxazol-3(2H)-one, and the like.

The above-mentioned compounds or salts thereof may be produced according to the process described in JP-A 6-41125/1994 (WO 93/04063) or its equivalent process.

18) Compounds of the formula:

Mqq-Wqq-Yqq-Aqq-Qqq wherein Mqq is a group of formula:

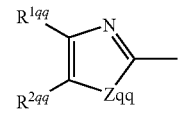

wherein R$^{1qq}$ is hydrogen, lower alkyl, optionally substituted heterocyclic group or optionally substituted aryl, and R$^{2qq}$ is hydrogen, lower alkyl, optionally substituted heterocyclic group or optionally substituted aryl, or R$^{1qq}$ and R$^{2qq}$ taken each other form a group of the formula:

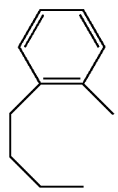

Zqq is S or O; a group of the formula:

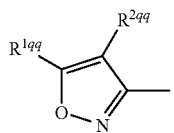

wherein $R^{1qq}$ and $R^{2qq}$ have the same meaning as mentioned above, or a group of the formula:

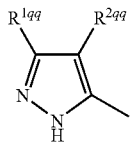

wherein $R^{1qq}$ and $R^{2qq}$ have the same meaning as mentioned above; Wqq is a bond, lower alkylene or lower alkenylene; Yqq is lower alkylene, —NH—, —CO—, a group of the formula: —$CONR^{3qq}$— (where $R^{3qq}$ is hydrogen or lower alkylene) or a group of the formula: —$CHR^{7qq}$— (where $R^{7qq}$ is hydroxy or protected hydroxy); Aqq is a bond or lower alkylene; Qqq is a group of the formula: —$NR^{8qq}R^{9qq}$ (where $R^{8qq}$ is lower alkyl; $R^{9qq}$ is ar(lower)alkyl or a group of the formula:

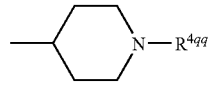

wherein $R^{4qq}$ is lower alkyl or optionally substituted ar(lower)alkyl; or salts thereof. Such compounds are exemplified by 4-(pyridin-3-yl)-5-methyl-2-[[2-(1-benzylpiperidin-4-yl)ethyl]carbamoyl]thiazole, 2-[[2-(1-benzylpiperidin-4-yl)ethyl]carbamoyl]-4-(4-chlorophenyl)-5-methyloxazole, 5-[[2-(1-benzylpiperidin-4-yl)ethyl]carbamoyl]-3-(4-nitrophenyl)pyrazole, and the like.

The above-mentioned compounds or salts thereof may be produced according to the process described in JP-A 5-345772/1993 or its equivalent process.

19) Compounds of the formula:

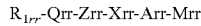

wherein $R_{1rr}$ is lower alkyl, optionally substituted heterocyclic group, optionally substituted aryl, optionally substituted ar(lower)alkyl or ar(lower)alkenyl; Qrr is oxadiazolediyl; Zrr is a bond or vinyl; Xrr is a bond, a group of the formula: —$CONR_{4rr}$— (where $R_{4rr}$ is hydrogen or lower alkyl), a group of the formula: —$CHR_{8rr}$— (where $R_{8rr}$ is hydroxy or protected hydroxy), —CO— or —NHCO—; Arr is a bond, lower alkylene or lower alkenylene; Mrr is a heterocyclic group which may be substituted by a substituent selected from lower alkyl, imino-protecting group and optionally substituted ar(lower)alkyl and which contains at least one nitrogen atom;

or salts thereof. Such compounds are exemplified by 5-(quinuclidin-3-yl)-3-[[2-(1-benzylpiperidin-4-yl)ethyl]-carbamoyl]-1,2,4-oxadiazole, 3-[[2-(1-benzylpiperidin-4-yl)ethyl]carbamoyl]-5-(4-nitrophenyl)-1,2,4-oxadiazole, and the like.

The above-mentioned compounds or salts thereof may be produced according to the process described in PCT JP-A 7-502529/1995 (WO 93/13083) or its equivalent process.

20) Compounds of the formula:

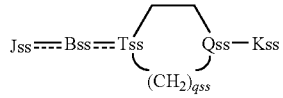

wherein Jss is (a) the following substituted or unsubstituted group: (1) phenyl, (2) pyridyl, (3) pyrazyl, (4) quinolyl, (5) cyclohexyl, (6) quinoxalyl, or (7) furyl, (b) a monovalent or divalent group selected from the following group, of which the phenyl moiety may be substituted: (1) indanyl, (2) indanonyl, (3) indenyl, (4) indenonyl, (5) indanedionyl, (6) tetralonyl, (7) benzsuberonyl, (8) indanolyl, or (9) a group of the formula:

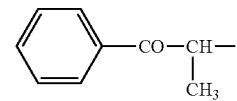

(c) a monovalent group derived from a cyclic amide compound,
(d) lower alkyl, or
(e) a group of the formula $R_{1ss}$, —CH=CH— (where $R_{1ss}$ is hydrogen or lower alkoxycarbonyl);

Bss is a group of the formula: —$(CHR_{2ss})nss$-, a group of the formula: —CO—$(CHR_{2ss})nss$-, a group of the formula: —$NR_{3ss}$, —$(CHR_{2ss})nss$- (where $R_{3ss}$ is hydrogen, lower alkyl, acyl, lower alkylsulfonyl, optionally substituted phenyl or benzyl), a group of the formula: —CO—$NR_{4ss}$—$(CHR_{2ss})nss$- (where $R_{4ss}$, is hydrogen, lower alkyl or phenyl), a group of the formula: —CH=CH—$(CHR_{2ss})nss$-, a group of the formula: —O—COO—$(CHR_{2ss})nss$-, a group of the formula: —O—CO—NH—$(CHR_{2ss})nss$-, a group of the formula: —NH—CO—$(CHR_{2ss})nss$-, a group of the formula: —$CH_2$—CO—NH—$(CHR_{2ss})nss$-, a group of the formula: —$(CH_2)_2$—CO—NH—$(CHR_{2ss})nss$-, a group of the formula: —C(OH)H—$(CHR_{2ss})nss$-(in the above formulae, nss indicates 0 or an integer of 1-10; $R_{2ss}$ means hydrogen or methyl when the alkylene of the formula —$(CHR_2SS)nss$- has no substituent or it has 1 or more of methyl), a group of the formula: =(CH—CH=CH)bss- (where bss is an integer of 1-3), a group of the formula: =CH—$(CH_2)$css- (where css is 0 or an integer of 1-9), a group of the formula: =(CH—CH) dss=(where dss is 0 or an integer of 1-5), a group of the formula: —CO—CH=CH—$CH_2$—, a group of the formula: —CO—$CH_2$—C(OH)H—$CH_2$—, a group of the formula: —C($CH_3$)H—CO—NH—$CH_2$—, a group of the formula: —CH=CH—CO—NH—$(CH_2)_2$—, a group of the formula: —NH—, a group of the formula: —O—, a group of the formula: —S—, dialkylaminoalkyl-carbonyl group or lower alkoxycarbonyl;

Tss is nitrogen or carbon atom;
Qss is nitrogen, carbon or a group of the formula >N→O;
Kss is hydrogen, substituted or unsubstituted phenyl, arylalkyl of which the phenyl moiety may be substituted, cinnamyl of which the phenyl moiety may be substituted, lower alkyl, pyridylmethyl, cycloalkylalkyl, admantanemethyl, furylmethyl, cycloalkyl, lower alkoxy-carbonyl or acyl;

qss is an integer of 1-3;

--- indicates a single bond or double bond;

or salts thereof. Such compounds are exemplified by 1-benzyl-4-[(5,6-dimethoxy-1-indanon)-2-yl]methylpiperidine, N-[4'-(1'-benzylpiperidyl)ethyl]-2-quinoxalinecarboxylic amide, 4-[4'-(N-benzyl)piperidyl]-p-methoxybutyrophenone, 1-[4'-(1'-benzylpiperidin)ethyl]-1,2,3,4-tetrahydro-5H-1-benzazepin-2-one, and the like.

The above-mentioned compounds or salts thereof may be produced according to the process described in JP-A 64-79151/1989 (U.S. Pat. No. 4,895,841) or its equivalent process.

21) Compounds of the formula:

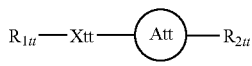

wherein $R^{1tt}$ is a mono-valent group derived from a compound selected from optionally substituted benzene, pyridine, pyrazine, indole, anthraquinone, quinoline, optionally substituted phthalimide, homophthalimide, pyridinecarboxylic imide, pyridine-N-oxide, pyrazinedicarboxylic imide, naphthalenedicarboxylic imide, optionally substituted quinazolidinedione, 1,8-naphthalimide, bicyclo[2.2.2]oct-5-ene-2,3-dicarboxylic imide and pyromellic imide; Xtt is a group of the formula: —$(CH_2)$mtt- (where mtt is an integer of 0-7), a group of the formula: —$O(CH_2)$ntt-, a group of the formula: —$S(CH_2)$ntt-, a group of the formula: —$NH(CH_2)$ntt-, a group of the formula: —$SO_2NH(CH_2)$ntt-, a group of the formula: —$NHCO(CH_2)$ntt-, a group of the formula: —$NH(CH_2)$ntt-CO—, a group of the formula: —$COO(CH_2)$ntt-, a group of the formula: —$CH_2NH(CH_2)$ntt-, a group of —$CONR_{3tt}$-$(CH_2)$ntt- (in the definition of Xtt, all of ntt in the formulae indicate an integer of 1-7; $R_{3tt}$ is lower alkyl or benzyl group), a group of the formula: —O—$CH_2CH_2CH(CH_3)$—, a group of the formula: —O—$CH(CH_3)CH_2CH_2$—, a group of the formula: —O—$CH_2CH_2CH$=, a group of the formula: —O—$CH_2CH(OH)CH_2$—; the ring Att represents a group of the formula:

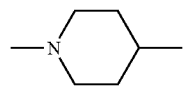

a group of the formula:

a group of the formula:

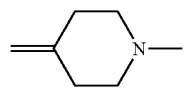

a group of the formula:

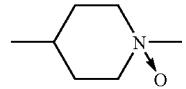

$R_{2tt}$ is hydrogen, lower alkyl, optionally substituted benzyl, optionally substituted benzoyl, pyridyl, 2-hydroxyethyl, pyridylmethyl, or a group of the formula:

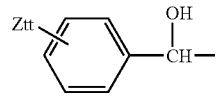

wherein Ztt means halogen;

or salts thereof. Such compounds are exemplified by N-methyl-N-[2-(1'-benzylpiperidin-4'-yl)ethyl]-4-benzylsulfonylbenzamide, N-(2-(N'-benzylpiperidin-4'-yl)ethyl]-4-nitrophthalimide, N-[2-(N'-benzylpiperidin-4'-yl)ethyl]-1,8-naphthalimide, and the like.

The above-mentioned compounds or salts thereof may be produced according to the process described in JP-A 62-234065/1987 (EP-A 229391) or its equivalent process.

22) Compounds of the formula:

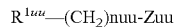

wherein $R^{1uu}$ is an optionally substituted group derived from cyclic amide compounds; nuu is 0 or an integer of 1-10; Zuu is (1) a group of the formula:

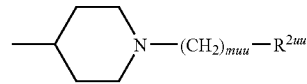

wherein $R^{2uu}$ is optionally substituted aryl, cycloalkyl or heterocyclic group; muu is an integer of 1-6 or, (2) a group of the formula:

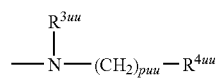

wherein $R^{3uu}$ is hydrogen or lower alkyl; $R^{4uu}$ is optionally substituted aryl, cycloalkyl or heterocyclic group; puu is an integer of 1-6; provided that the following cases are excluded: when the optionally substituted cyclic amide compound is quinazolidinone or quinazolidinedione in the definition of $R^{1uu}$, and when $R^{2uu}$ and $R^{4uu}$ are aryl in the definition of Zuu; or salts thereof. Such compounds are exemplified by 3-[2-(1-benzyl-4-piperidyl)ethyl]-5-methoxy-2H-3,4-dihydro-1,3-benzoxazin-2-one, 3-[2-[1-(4-pyridylmethyl)-4-piperidyl]-ethyl]-2H-3,4-dihydro-1,3-benzoxazin-2-one, 3-[2-[1-(1,3-dioxolan-2-ylmethyl)-4-piperidyl]ethyl]-5-methoxy-1,2,3,4-tetrahydroquinazoline-2,4-dione, 3-[2-(1-benzyl-4-piperidyl)ethyl]-6-methoxy-2H-3,4-dihydro-1,3-benzoxadine-2,4-dione, and the like.

The above-mentioned compounds or salts thereof may be produced according to the process described in JP-A 4-235161/1992 (EP-A 468187) or its equivalent process.

23) An optically active indanone derivatives of the formula:

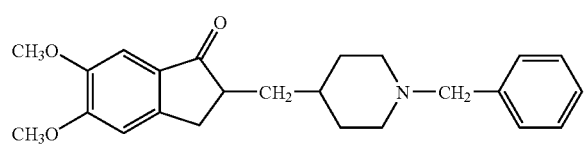

or salts thereof.

The above-mentioned compound or salts thereof may be produced according to the process described in JP-A 4-21670/1992 or its equivalent process.

24) Compounds of the formula:

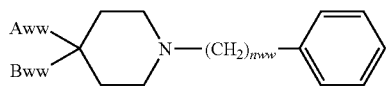

wherein nww is 0 or an integer of 1 or 2; Aww is a group of the formula:

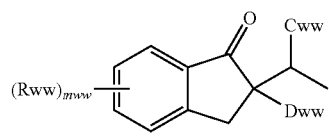

wherein Cww is hydrogen or hydroxy; Dww is hydrogen or lower hydroxyalkyl; Rww is the same or different representing a group selected from hydrogen atom, lower alkyl and lower alkoxy; mww is 0 or an integer of 1-4, or a group of the formula:

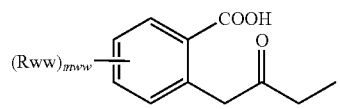

wherein each symbol has the same meaning as mentioned above; Bww is hydrogen or hydroxy; or alternatively, Aww and Bww taken together form a double bond to form a group of the formula:

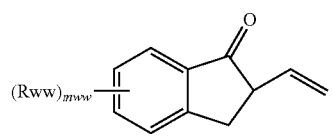

wherein each symbol has the same meaning as mentioned above;
or salts thereof. Such compounds are exemplified by 1-benzyl-4-(5,6-dimethoxy-1-indanon-2-yl)hydroxymethylpiperidine, 1-benzyl-4-(5,6-dimethoxy-2-hydroxymethyl-1-indanon-2-yl)-methylpiperidine, 1-benzyl-4-[3-(4,5-dimethoxy-2-carboxy-phenyl)-2-oxo]propylpiperidine, and the like.

The above-mentioned compounds or salts thereof may be produced according to the process described in JP-A 9-268176/1997 or its equivalent process.

25) Compounds of the formula:

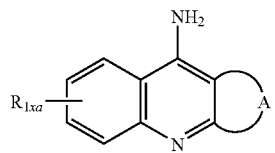

wherein $R_{1xa}$ is hydrogen, halogen, hydroxy, lower alkoxy, lower alkyl or mono(or di or tri)halo(lower)alkyl; the group of the formula:

represents a moiety of the formula:

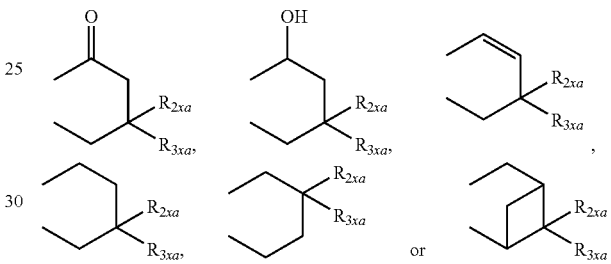

wherein $R_{2xa}$ and $R_{3xa}$ each is lower alkyl;
or salts thereof. Such compounds are exemplified by 9-amino-6-chloro-3,3-dimethyl-1,2,3,4-tetrahydroacridine, and the like.

The above-mentioned compounds or salts thereof may be produced according to the process described in JP-A 2-167267/1990 or its equivalent process.

26) Aminoazaacridine derivatives of the formula:

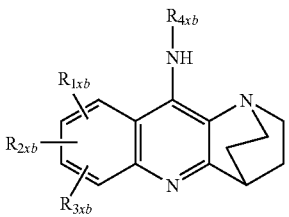

wherein $R_{1xb}$, $R_{2xb}$ and $R_{3xb}$ each is hydrogen, halogen, trifluoromethyl, lower alkyl, lower cycloalkyl, lower alkoxy, lower alkoxymethyl, lower alkylthio, nitro, amino, lower alkanoylamino, lower alkylamino, hydroxy, phenyl or phenyl substituted by halogen, lower alkyl or lower alkoxy;
$R_{4xb}$ is hydrogen, lower alkyl, aralkyl, diaralkyl, or a group of the formula: $R_{5xb}$—CO—($R_{5xb}$ is lower alkyl, lower cycloalkyl, aralkyl, phenyl or phenyl substituted by halogen, lower alkyl or lower alkoxy);
or salts thereof. Such compounds are exemplified by 9-amino-8-fluoro-1,2,3,4-tetrahydro-1,4-ethano-1-azaacridine, and the like.

The above-mentioned compounds or salts thereof may be produced according to the process described in JP-A 63-166881/1988 or its equivalent process.

27) Compounds of the formula:

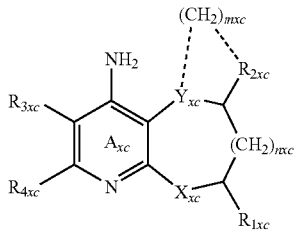

wherein $R_{1xc}$ is hydrogen or lower alkyl; $R_{2xc}$ is independently hydrogen or lower alkyl, or it taken with $R_{6xc}$ forms a cyclic alkylene chain; $R_{3xc}$ and $R_{4xc}$ each is independently hydrogen, or they taken together with the ring $A_{xc}$ form a quinoline ring or tetrahydroquinoline ring; $X_{xc}$ is oxygen, sulfur or N—$R_{5xc}$, and $R_{5xc}$ is hydrogen or lower alkyl; $Y_{xc}$ is oxygen or N—$R_{6xc}$, and $R_{6xc}$ is independently hydrogen or lower alkyl, or it taken with $R_{2xc}$ forms a cyclic alkylene; nxc is 0 or 1; mxc is an integer of 0-4; or salts thereof. Such compounds are exemplified by 4'-amino-quinolino[2,3-b]-4-methyl-5,6-dihydro-1,4-oxazine, 4'-amino-5',6',7',8'-tetrahydroquinolino[2,3-b]-4-methyl-5,6-dihydro-1,4-oxazine, and the like.

The above-mentioned compounds or salts thereof may be produced according to the process described in JP-A 2-96580/1990 or its equivalent process.

28) Compounds of the formula:

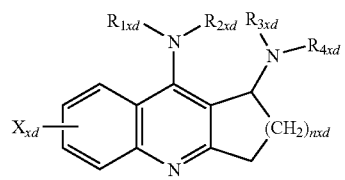

wherein nxd is 1, 2 or 3, and Xxd is hydrogen, lower alkyl, lower alkoxy, halogen, hydroxy, nitro or trifluoromethyl; $R_{1xd}$ and $R_{2xd}$ each is independently hydrogen, lower alkyl or aryl lower alkyl, but they cannot be aryl lower alkyl concurrently; $R_{3xd}$ and $R_{4xd}$ each is independently hydrogen, lower alkyl, aryl lower alkyl, formyl or lower alkylcarbonyl, or the group —$NR_{3xd}R_{4xd}$ represents the following group:

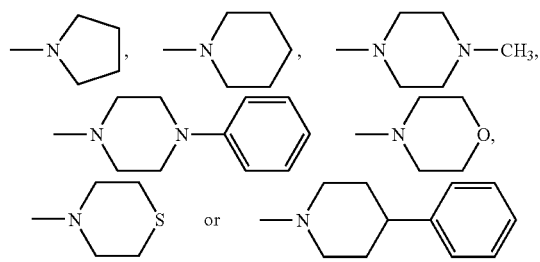

as a whole;
or stereoisomers thereof or their salts. Such compounds are exemplified by 1-(1-piperidinyl)-1,2,3,4-tetrahydro-9-acridinamine, N-1-ethyl-1,2,3,4-tetrahydro-1,9-acridine-diamine, and the like.

The above-mentioned compounds or salts thereof may be produced according to the process described in JP-A 3-15366711991 or its equivalent process.

29) Compounds of the formula:

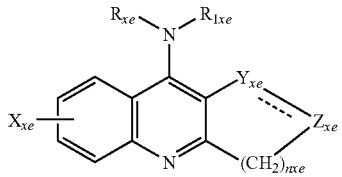

wherein nxe is 1, 2 or 3; $X_{xe}$ is hydrogen, $C_1$-$C_6$ alkyl, $C_1$-$C_6$ alkoxy, halogen, hydroxy, nitro, trifluoromethyl, $NHCOR_{2xe}$ (where $R_{2xe}$ is $C_1$-$C_6$ alkyl) or $NR_{3xe}R_{4xe}$ (where $R_{3xe}$ and $R_{4xe}$ are independently hydrogen or $C_1$-$C_6$ alkyl); $R_{xe}$ is hydrogen or $C_1$-$C_6$ alkyl; $R_{1xe}$ is hydrogen, $C_1$-$C_6$ alkyl, di-$C_1$-$C_6$ alkylamino-$C_1$-$C_6$ alkyl, aryl-$C_1$-$C_6$ alkyl, diaryl-$C_1$-$C_6$ alkyl, furyl-$C_1$-$C_6$ alkyl, thienyl-$C_1$-$C_6$ alkyl, oxygen-bridged aryl-$C_1$-$C_6$ alkyl, oxygen-bridged diaryl-$C_1$-$C_6$ alkyl, oxygen-bridged furyl-$C_1$-$C_6$ alkyl, or oxygen-bridged thienyl-$C_1$-$C_6$ alkyl; $Y_{xe}$ is C=O or $CR_{5xe}OH$ (where $R_{5xe}$ is hydrogen or $C_1$-$C_6$ alkyl); and $Z_{xe}$ is $CH_2$ or $C=CR_{6xe}R_{7xe}$ (where $R_{6c}$ and $R_{7xe}$ are independently hydrogen or $C_1$-$C_6$ alkyl), or $Y_{xe}$ and $Z_{xe}$ taken together form $CR_{5xe}$=CH (where $CR_{5xe}$ and CH respectively correspond to $Y_{xe}$ and $Z_{xe}$);
or optical antipodes thereof or their salts Such compounds are exemplified by 9-amino-3,4-dihydroacridin-1(2H)-one, 9-amino-1,2,3,4-tetrahydroacridin-1-ol, and the like.

The above-mentioned compounds or salts thereof may be produced according to the process described in JP-A 61-148154/1986 or JP-B 5-41141/1993 or its equivalent process 30) Compounds of the formula:

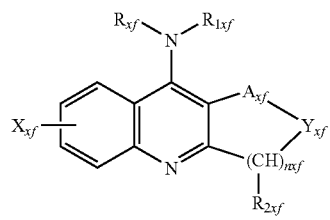

wherein nxf is 1-4; $R_{xf}$ is hydrogen, lower alkyl or lower alkylcarbonyl; $R_{1xf}$ is hydrogen, lower alkyl, lower alkylcarbonyl, aryl, di(lower)alkylamino(lower)alkyl, aryl lower alkyl, diaryl lower alkyl, oxygen-bridged aryl lower alkyl, or oxygen-bridged diaryl lower alkyl; Axf is a direct bond or $(CHR_{3xf})$mxf; mxf is 1-3; Xxf is hydrogen, lower alkyl, cyclo-alkyl, lower alkoxy, halogen, hydroxy, nitro, trifluoromethyl, formyl, lower alkylcarbonyl, arylcarbonyl, —SH, lower alkyl-thio, —$NHCOR_{4xf}$ or $NR_{5xf}R_{6xf}$; in the above formulae, $R_{4xf}$ is hydrogen or lower alkyl; $R_{5xf}$ and $R_{6xf}$ each is independently hydrogen, lower alkyl or cycloalkyl; Yxf is O, S or $NR_{7xf}$; each $R_{2f}$, each $R_{3xf}$ and $R_{7xf}$ are independently hydrogen or lower alkyl, or two of them concurrently form a methylene or ethylene group which constitutes a moiety of a ring comprising at least 5 atoms; provided that when Axf is $CH_2$, Yxf is $NCH_3$, $(CHR_{2xf})$nxf is $CH_2CH_2$, Xxf is H, $CH_3$, Cl, Br or $NO_2$, and $R_{xf}$ is H, then $R_{1xf}$ is neither H, methyl, ethyl, propyl, butyl nor benzyl; when Axf is —$CH_2$— or CHR'—, Yxf is NH or NR', and $(CHR_{2xf})$nxf is —$CH_2CH_2$— or $CH_2CHR'$—, then the group —$NR_{xf}R_{1xf}$ is neither —$NH_2$, —$NHC_6H_5$ nor di(lower) alkylamino(lower)alkylamino, and each R' is independently lower alkyl; when Axf is $CH_2$, Yxf is NH or NR', and (CHR$_2$Xf)nxf is —(CH$_2$)$_3$— or CHR'CH$_2$CH$_2$—, then the group —NR$_{xf}$R$_{1xf}$ is not —NH$_2$; when Axf is —CH$_2$CH$_2$—, Yxf is NH or NR', and (CHR$_{2xf}$) nxf is —CH$_2$CH$_2$— or CHR'CH$_2$—, then the group —NR$_{xf}$R$_{1xf}$ is not —NH$_2$;

or optical or geometrical isomers thereof or their salts. Such compounds are to exemplified by 9-amino-2,3-dihydrothieno [3,2-b]quinoline, 10-amino-3,4-dihydro-1H-thiopyrano[4,3-b]-quinoline, and the like.

The above-mentioned compounds or salts thereof may be produced according to the process described in JP-A 63-284175/1988 or its equivalent process.

31) Compounds of the formula:

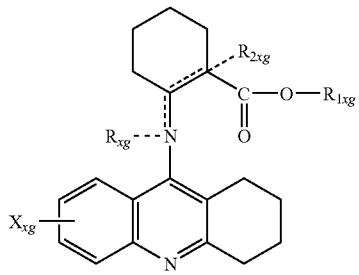

wherein Xxg is hydrogen, lower alkyl, lower alkoxy or halogen; R$_{xg}$ is, when it is present, hydrogen, lower alkyl or aryl lower alkyl; R$_{1xg}$ is hydrogen, lower alkyl or aryl lower alkyl; and R$_{2xg}$ is, when it is present, hydrogen or lower alkyl; or salts thereof. Such compounds are exemplified by 2-(1,2,3,4-tetrahydro-9-acridinimino)cyclohexanecarboxylic acid, ethyl 2-(1,2,3,4-tetrahydro-9-acridinimino)cyclohexanecarboxylate, and the like.

The above-mentioned compounds or salts thereof may be produced according to the process described in JP-A 3-95161/1991 or its equivalent process.

32) Compounds of the formula:

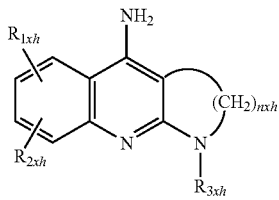

wherein R$_{1xh}$ and R$_{2xh}$ each is hydrogen, halogen, lower alkyl, trifluoromethyl, hydroxy, lower alkoxy, lower alkanoyloxy, nitro, amino or lower alkanoylamino; R$_{3xh}$ is hydrogen, alkyl of 1-15 carbon atoms, cycloalkyl, aralkyl of 7-15 carbon atoms optionally substituted by halogen, lower alkyl or lower alkoxy, alkanoyl of 2-15 carbon atoms, or benzoyl which may be substituted by halogen, lower alkyl, lower alkoxy, nitro, hydroxy or amino; nxh is an integer of 2-5;

or salts thereof. Such compounds are exemplified by 6-amino-1-benzyl-2,3,4,5-tetrahydro-1H-azepino[2,3-b] quinoline, 5-amino-6-fluoro-1,2,3,4-tetrahydrobenzo[d][1,8]naphthyridine, and the like.

The above-mentioned compounds or salts thereof may be produced according to the process described in JP-A 3-220189/1991 or its equivalent process.

33) 4-Amino-5,6,7,8-tetrahydrothieno[2,3-b]quinoline derivatives of the formula:

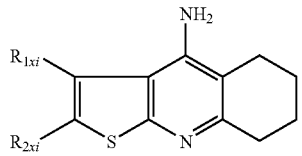

wherein R$_{1xi}$ and R$_{2xi}$ each is hydrogen or straight or branched chain alkyl of 1-4 carbon atoms, provided that they are not hydrogen concurrently;

or salts thereof. Such compounds are exemplified by 4-amino-2,3-dimethyl-5,6,7,8-tetrahydrothieno[2,3-b] quinoline, and the like.

The above-mentioned compounds or salts thereof may be produced according to the process described in JP-A 4-134083/1992 or its equivalent process.

34) 4-Amino-2,3-cycloalkenopyridine and 4-aminoquinoline derivatives of the formula:

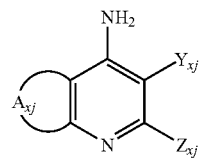

wherein Axj represents alkylene of the formula —(CH$_2$)nxj-(where nxj is an integer of 3-5), which is bound to two adjacent carbon atoms on the adjacent pyridine nucleus to form a cycloalkenone group or which is associated with two adjacent carbon atoms on the adjacent pyridine nucleus to form a benzene ring; and (i) when Axj forms a cycloalkenone group, then Yxj represents hydrogen, halogen, C$_1$-C$_6$ lower alkyl or amino, and Zxj represents hydrogen; hydroxy, halogen, amino, a group of the formula —NR$_{1xj}$R$_{2xj}$(R$_{1xj}$ and R$_{2xj}$ are the same or different representing lower alkyl or benzyl), pyrrolidyl, piperidyl, piperazyl, N-substituted piperazyl, pyridyl, or a group of the formula:

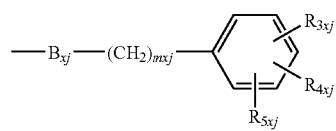

(wherein B is oxygen or sulfur; mxj is an integer of 0-2; R$_{3xj}$, R$_{4xj}$ and R$_{5xj}$ are the same or different representing hydrogen, halogen, trifluoromethyl, hydroxy, lower alkoxy, straight or branched (C$_1$-C$_6$) lower alkyl, amino, or acylamino), or Zxj represents pyridylthio; and (ii) when Axj forms a benzene ring, then Yxj represents hydrogen or C$_1$-C$_6$ lower alkyl, and Zxj represents a group of the formula —CONR$_{6xj}$R$_{7xj}$ (where R$_{6xj}$ and R$_{7xj}$ each is hydrogen or C$_1$-C$_6$ lower alkyl, or alternatively R$_{6xj}$ and R$_{7xj}$ are taken together to form a C$_3$-C$_6$ cycloalkyl), or Zxj represents a group of the formula:

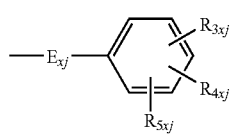

wherein Exj is $C_2$-$C_6$ alkylene or a group of the formula —(CH=CH)pxj- (where pxj is 1 or 2), and $R_{3xj}$, $R_{4xj}$ and $R_{5xj}$ have the same meaning as mentioned above;
or salts thereof. Such compounds are exemplified by 4-amino-2-(N-methylcarbamoyl)quinoline, and the like.

The above-mentioned compounds or salts thereof may be produced according to the process described in JP-A 4-66571/1992 or its equivalent process.

35) Polycyclic aminopyridine compounds of the formula:

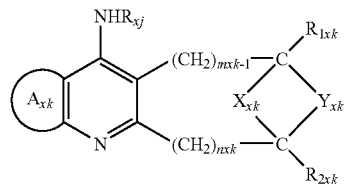

wherein $R_{xk}$ is hydrogen, alkyl, aralkyl or acyl; $R_{1xk}$ and $R_{2xk}$ each is independently hydrogen, alkyl, aralkyl, alkoxy, alkoxy-carbonyl, amino or amino substituted by 1 or 2 of alkyl, aralkyl or acyl; mxk and nxk each is 1, 2 or 3; Xxk and Yxk each is independently a bond between two carbon atoms, oxygen or sulfur, a group N—$R_{3xk}$ (where the group $R_{3xk}$ and $R_{xk}$ have the same meaning as mentioned above), or an alkylene or alkenylene crosslink which contains 1-5 carbon atoms and may contain 1 or more of the substituent $R_{4xk}$ (where $R_{4xk}$ is independently hydrogen, straight or branched chain lower alkyl of 1-4 carbon atoms, alkenyl or alkylidene, phenyl or phenyl which is substituted by 1 or more of lower alkyl of 1-4 carbon atoms, lower alkoxy of 1-4 carbon atoms or halogen, aralkyl, lower alkoxy of 1-4 carbon atoms, or hydroxy); and when Yxk is alkenylene, the latter can be condensed with a saturated or unsaturated carbocyclic or heterocyclic ring, and the above-mentioned ring may be substituted by 1 or more of groups of $R_{5xk}$ ($R_{5xk}$ is hydrogen, lower alkyl or lower alkoxy of 1-4 carbon atoms, or halogen); and the group of formula:

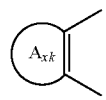

represents a moiety of the formula:

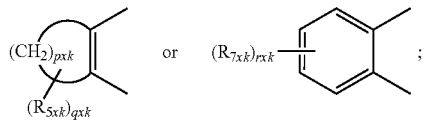

pxk, qxk and rxk each is 1 or more; and $R_{6xk}$ or $R_{7xk}$ may be independently hydrogen, halogen, lower alkoxy or lower alkyl;
or salts thereof. Such compounds are exemplified by (+)-12-amino-6,7,10,11-tetrahydro-9-ethyl-7,11-methanocycloocta-[b]quinoline, (+)-12-amino-6,7,10,11-tetrahydro-9-methyl-7,11-methanocycloocta[b]quinoline, and the like.

The above-mentioned compounds or salts thereof may be produced according to the process described in PCT JP-A 11-500144/1999 or its equivalent process.

36) Compounds of the formula:

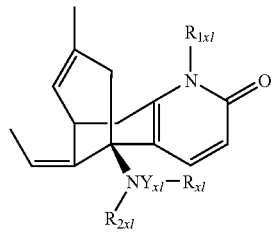

wherein $Y_{xl}$ is —C=O or —$R_{2xl}$; Y is =CH; $R_{xl}$ is $C_1$-$C_5$ lower alkyl, a group of the formulae:

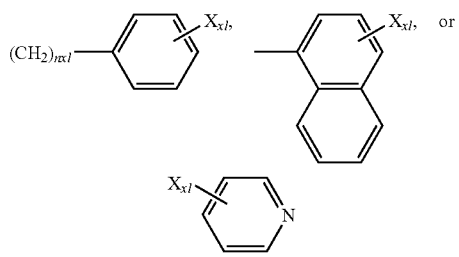

(where nxl=0 or 1; Xxl is hydrogen, $C_1$-$C_5$ lower alkyl, $C_1$-$C_5$ lower alkoxy, nitro, halogen, carboxy, alkoxycarbonyl, hydroxymethyl, hydroxy, bis-$C_1$-$C_5$ lower alkyl-substituted amino), —(CH$_2$)$_{mxl}$COOZxl (where mxl=0-5; Zxl is hydrogen or $C_1$-$C_5$ lower alkyl), —CH=CH-Gxl (where Gxl is phenyl, furanyl, carboxy, or alkoxycarbonyl), and dihydro- or tetrahydro-pyridyl substituted by $C_1$-$C_5$ lower alkyl at the nitrogen atom; $R_{1xl}$ is hydrogen, $C_1$-$C_5$ lower alkyl, pyridoyl and $C_1$-$C_5$ lower alkoxy-substituted benzoyl; $R_{2xl}$ is hydrogen or $C_1$-$C_5$ lower alkyl;
or salts thereof. Such compounds are exemplified by one of the formula:

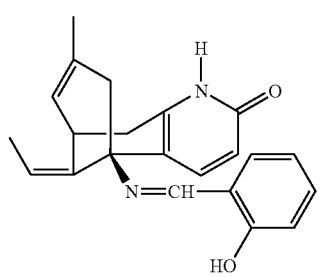

and the like.

The above-mentioned compounds or salts thereof may be produced according to the process described in PCT JP-A 10-511651/1998 or its equivalent process.

37) Compounds of the formula:

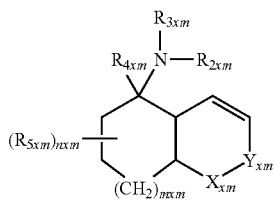

wherein Xxm-Yxm is a group of the formula:

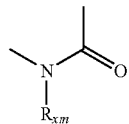

(wherein $R_{xm}$ is hydrogen, lower alkyl, lower alkenyl, lower alkynyl or aryl lower alkyl) or a group of the formula:

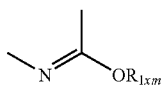

(wherein $R_{1xm}$ is hydrogen, lower alkyl or aryl lower alkyl); $R_{2xm}$ and $R_{3xm}$ each is independently hydrogen, lower alkyl, aryl lower alkyl, diaryl lower alkyl, lower cycloalkenyl lower alkyl, lower alkoxy, aryl lower alkoxy or lower alkanoyl, or $R_{2xm}$ and $R_{3xm}$ taken with the attached nitrogen atom form a group of the formula:

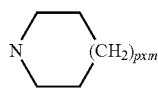

(wherein pxm is 0 or 1) or a group of the formula:

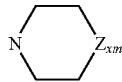

(wherein Zxm is O, S or a group of the formula $NR_{6xm}$ ($R_{6xm}$ is hydrogen, lower alkyl or aryl lower alkyl)); $R_{4xm}$ is hydrogen, lower alkyl or aryl lower alkyl; $R_{5xm}$ is hydrogen, lower alkyl or aryl lower alkyl; mxm is 0, 1 or 2; and nxm is 1 or 2; or geometrical and optical isomers thereof or their salts. Such compounds are exemplified by N-(1,2,5,6,7,8-hexahydro-5-methyl-2-oxo-5-quinolinyl)acetamide, 5-[[2-(3,4-dichlorophenyl)ethyl]amino]-5,6,7,8-tetrahydro-1-methyl-2(1H)-quinoline, and the like.

The above-mentioned compounds or salts thereof may be produced according to the process described in JP-A 4-290872/1992 or its equivalent process.

38) Compounds of the formula:

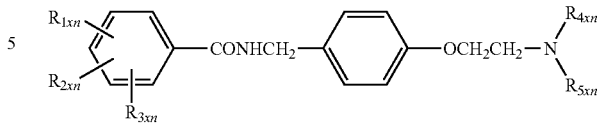

wherein $R_{1xn}$, $R_{2xn}$, and $R_{3xn}$ each is hydrogen, lower alkyl, lower alkoxy, hydroxy, halogen, nitro, cyano, amino optionally substituted by lower alkyl, or sulfamoyl optionally substituted by lower alkyl, or $R_{1xn}$, and $R_{2xn}$ taken together form methylenedioxy; $R_{4xn}$ and $R_{5xn}$ each is lower alkyl or cycloalkyl of 3 to 6 carbon atoms, or they taken together with the attached nitrogen atom may form 1-pyrrolidinyl, 1-piperidinyl, 1-piperazinyl or 4-morpholinyl, each of which may be substituted by lower alkyl;
or salts thereof. Such compounds are exemplified by N-[4-[2-(dimethylamino)ethoxy]benzyl]-2-ethoxybenzamide, 4-amino-N-[4-[2-(dimethylamino)ethoxy]benzyl]-2-methoxy-5-sulfamoyl-benzamide, and the like.

The above-mentioned compounds or salts thereof may be produced according to the process described in JP-A 2-231421/1990 or its equivalent process.

39) Compounds of the formula:

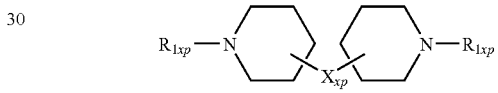

wherein Xxp is straight or branched chain alkylene of 1-10 carbon atoms or a group of the formula:

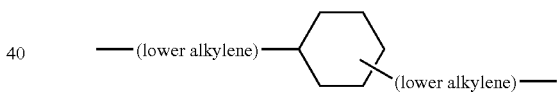

or of the formula:

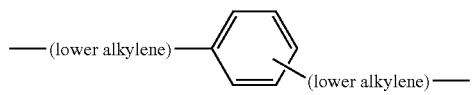

$R_{1xp}$ is Arxp-$CHR_{2xp}$ (where Arxp is unsubstituted phenyl or phenyl substituted by halogen, trifluoromethyl, lower alkyl or lower alkoxy; $R_{2xp}$ is hydrogen or lower alkyl), cinnamyl of which the phenyl moiety is unsubstituted or substituted by halogen, lower alkyl or lower alkoxy, a cycloalkylmethyl, or methyl substituted by heterocyclic aromatic group; and when one linkage of X to the two piperidine rings is placed at the 2-position, the other is at the 2'-position, and when one is at the 3-position, the other is at the 3'-position, and when one is at the 4-position, the other is at the 4'-position; or salts thereof. Such compounds are exemplified by 1,6-di-(1-benzyl-4-piperidyl)hexane, 1,5-di-(1-benzyl-4-piperidyl)-pentane, and the like.

The above-mentioned compounds or salts thereof may be produced according to the process described in JP-A 4-18071/1992 or its equivalent process.

40) Compounds of the formula:

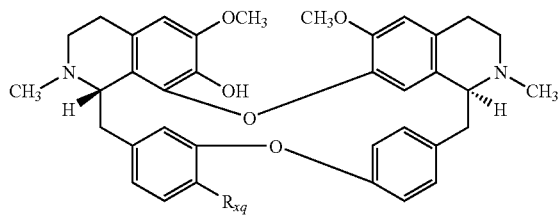

[wherein Rxq is hydroxy or methoxy]
or salts thereof.

The above-mentioned compounds or salts thereof may be produced according to the process described in JP-A 4-159225/1992 or its equivalent process.

41) 9-Amino-1,2,3,4-tetrahydroacridine represented by the following formula or salts thereof

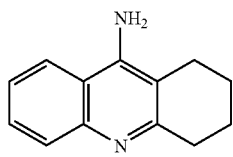

The above-mentioned compound or salts thereof may be produced according to the process described in JP-A 4-346975/1992 or its equivalent process.

42) Compounds of the formula:

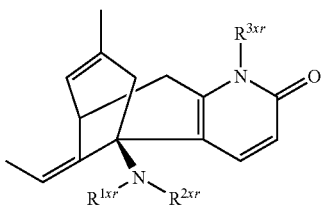

wherein $R^{1xr}$, $R^{2xr}$ and $R^{3xr}$ each is hydrogen or lower alkyl; or salts thereof.

Huperzine A represented by the following formula or salts thereof

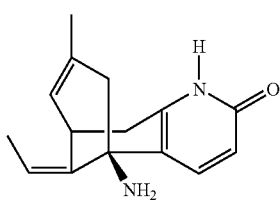

The above-mentioned compounds or salts thereof may be produced according to the process described in U.S. Pat. No. 5,177,082, J. Am. Chem. Soc., 1991, 113, p. 4695-4696, or J. Am. Chem. Soc., 1989, 111, p. 4116-4117, or its equivalent process, or obtained by extraction and isolation from a Chinese herb, Qian ceng ta (Lycopodium serratum (Huperizia serrata)Thunb).

43) Galanthamine or galanthamine derivatives represented by the following structural formula.

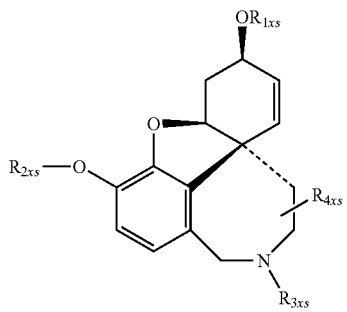

In the above formula, $R_{1xs}$ and $R_{2xs}$ are the same or different, each representing hydrogen or acyl such as lower alkanoyl, for example, acetyl, or a straight or branched alkyl, for example, methyl, ethyl, propyl, isopropyl, and the like.

$R_{3xs}$ is straight or branched alkyl, alkenyl or alkaryl, and these groups may be replaced optionally by halogen, cycloalkyl, hydroxy, alkoxy, nitro, amino, aminoalkyl, acylamino, heteroaryl, heteroaryl-alkyl, aroyl, aroylalkyl, or cyano.

$R_{4xs}$ means hydrogen or halogen attached to at least one of carbon atoms that constitute the tetra-cyclic skeletal structure; provided that when $R_4$ is placed at the adjacent position to the nitrogen atom, $R_4$ is preferably different from halogen, as well as from, for example, hydrohalides such as hydrobromide, hydrochloride, etc., methyl sulfate or methiodide.

Such a compound is exemplified by galanthamine represented by the following formula or salts thereof

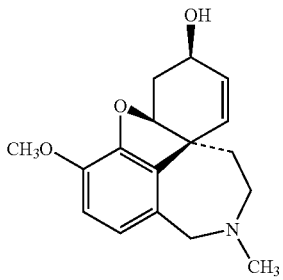

The above-mentioned compounds or salts thereof may be produced according to the process described in PCT JP-A 6-507617/1994, Heterocycles, 1977, 8, p. 277-282, or J. Chem. Soc. (C), 1971, p. 1043-1047, or its equivalent process, or obtained by extraction and isolation from a Liliaceae plant such as *Galanthus nivalis* or *Galanthus waronowii*.

44) Substituted amines of the formula:

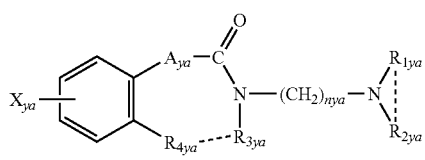

wherein $R_{1ya}$ and $R_{2ya}$ each is independently hydrogen or optionally substituted hydrocarbon residue, or they taken with the adjacent nitrogen atom form a heterocyclic group; as for $R_{3ya}$ and $R_{4ya}$, $R_{3ya}$ represents hydrogen or an optionally substituted hydrocarbon residue or acyl and $R_{4ya}$ represents hydrogen, or $R_{3ya}$ and $R_{4ya}$ taken together may form —$(CH_2)_{may}$—CO—, —CO—$(CH_2)_{mya}$— or $(CH_2)_{may+1}$— (where mya is 0, 1 or 2); $A_{ya}$ represents —$(CH_2)_{lya}$—, (lya is 0, 1 or 2) or —CH=CH—; $X_{ya}$ indicates 1 or more of substituents; nya is an integer of 4 to 7;
or salts thereof.

The above-mentioned compounds or salts thereof may be produced according to the process described in JP-A 2-91052/1990 or its equivalent process.

45) Aminoketone derivatives of the formula:

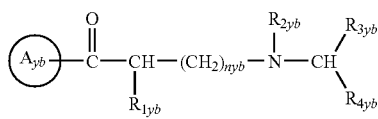

wherein the ring $A_{yb}$ is a 5- to 8-membered cyclic group which may be substituted and may contain 1 or 2 ring-constituting heteroatoms of O, S and N; $R_{1yb}$ is hydrogen or optionally substituted hydrocarbon residue; $R_{2yb}$ is hydrogen or lower alkyl; $R_{3yb}$ is an optionally substituted aromatic group; $R_{4yb}$ is hydrogen or lower alkyl or optionally substituted aromatic group; and nyb is an integer of 2-7; or salts thereof.

The above-mentioned compounds or salts thereof may be produced according to the process described in JP-A 3-95143/1991 or its equivalent process.

46) Aralkylamine derivatives of the formula:

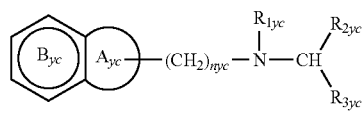

wherein $R_{1yc}$ is hydrogen or lower alkyl; $R_{2yc}$ is an optionally substituted aromatic group; $R_{3yc}$ is hydrogen or lower alkyl or optionally substituted aromatic group; nyc is an integer of 0-7; the ring $A_{yc}$ is a 5- to 8-membered cyclic group which may be substituted and may contain 1 or 2 ring-constituting heteroatoms of O and S; the ring $B_{yc}$ is an optionally substituted benzene ring;
or salts thereof.

The above-mentioned compounds or salts thereof may be produced according to the process described in JP-A 3-141244/1991 or its equivalent process.

47) Aminonaphthalene compounds of the formula:

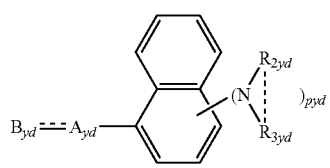

wherein $B_{yd}$ is an optionally substituted saturated or unsaturated 5- to 7-membered aza-heterocyclic group; $A_{yd}$ is a bond or hydrocarbon residue, or bivalent or trivalent aliphatic hydrocarbon residue optionally substituted by oxo, hydroxyimino or hydroxy; --- indicates a single bond or double bond (provided that when $A_{yd}$ is a bond, then --- is a single bond), $R_{2yd}$ and $R_{3yd}$ each is independently hydrogen or optionally substituted hydrocarbon residue, or they taken with the adjacent nitrogen atom may form a cyclic amino; pyd is 1 or 2;
or salts thereof.

The above-mentioned compounds or salts thereof may be produced according to the process described in JP-A 3-223251/1991 or its equivalent process.

48) Condensed heterocyclic carboxylic acid derivatives of the formula:

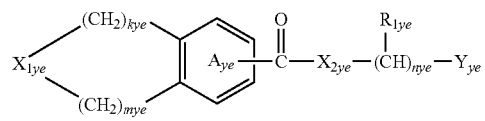

wherein $X_{1ye}$ is $R_{4ye}$—N($R_{4ye}$ is hydrogen, optionally substituted hydrocarbon group or optionally substituted acyl), oxygen or sulfur; $X_{2ye}$ is $R_{5ye}$—N($R_{5ye}$ is hydrogen, optionally substituted hydrocarbon group or optionally substituted acyl) or oxygen; the ring $A_{ye}$ is a benzene ring which may be substituted by an additional substituent; $R_{1ye}$ is hydrogen or optionally substituted hydrocarbon group; each of $R_{1ye}$ may be different according to repitition of nye; $Y_{ye}$ is optionally substituted amino or optionally substituted nitrogen-containing saturated heterocyclic group; nye is an integer of 1 to 10; kye is an integer of 0 to 3; and mye is an integer of 1 to 8;
or salts thereof.

The above-mentioned compounds or salts thereof may be produced according to the process described in JP-A 5-23902411993 or its equivalent process.

49) Unsaturated carboxylic amide derivatives of the formula:

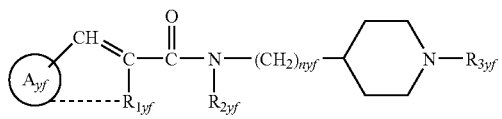

wherein the ring $A_{yf}$ is an optionally substituted aromatic ring; $R_{1yf}$ is hydrogen or optionally substituted hydrocarbon residue, or it is taken with the adjacent group of —CH=C— and the two carbon atoms constituting the ring $A_{yf}$ to form an optionally substituted carbocycle; $R_{2yf}$ is hydrogen, or optionally substituted hydrocarbon residue or acyl; $R_{3yf}$ is an optionally substituted hydrocarbon residue; and nyf is an integer of 2 to 6;
or salts thereof.

The above-mentioned compounds or salts thereof may be produced according to the process described in JP-A 2-138255/1990 or its equivalent process.

Treatable Diseases

As for "non-carbamate-type amine compounds having an acetylcholinesterase inhibiting action" used in the invention, Compounds (I) are preferably exemplified.

The non-carbamate-type amine compounds having an acetylcholinesterase inhibiting action used in the present invention, exhibit a potent effect increasing the contraction of the muscle of urinary bladder, with lesser toxicity, but not contracting the muscle of urethra. The compounds, accordingly, can be used as agents for improving excretory potency of the urinary bladder in mammals including human. The compounds can be used as prophylactic or therapeutic agents for dysuria, particularly for difficulty of urination, which is caused, for example, by the following items 1) to 6). 1)

Prostatomegaly, 2) atresia in neck of urinary bladder, 3) neuropathic bladder, 4) diabetes mellitus, 5) surgical operation, and 6) hypotonia in muscle of urinary bladder. The compounds can also be used in treatment of dysuria such as pollakiuria, incontinence of urine, etc.

The non-carbamate-type amine compounds having an acetylcholinesterase inhibiting action, when used as prophylactic and therapeutic agents in dysuria caused by prostatomegaly, particularly difficulty of urination, may be used in combination with other drugs (for example, α-blockers such as tamsulosin, and the like). These drugs may be used simultaneously or in combination of individually formulated preparations.

The α-blockers that can be used in combination with the compounds of the invention, include, for example, the following compounds or salts thereof.

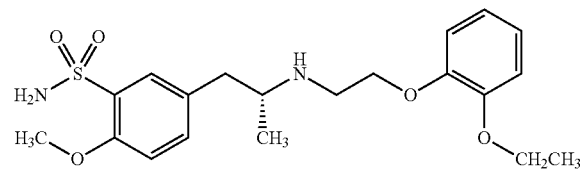

Tamsulosin: EP-A 34432, U.S. Pat. No. 4,703,063

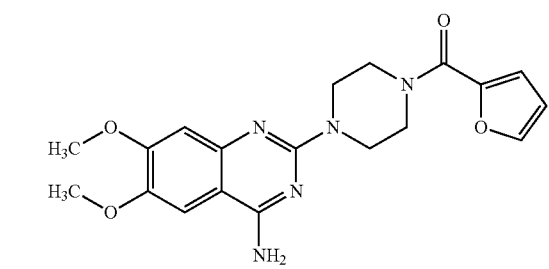

Prazosin: U.S. Pat. No. 3,511,836

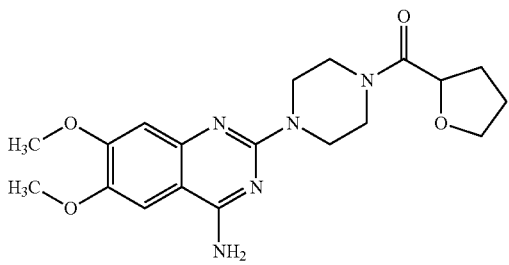

Terazosin: U.S. Pat. No. 4,026,894, U.S. Pat. No. 4,251,532

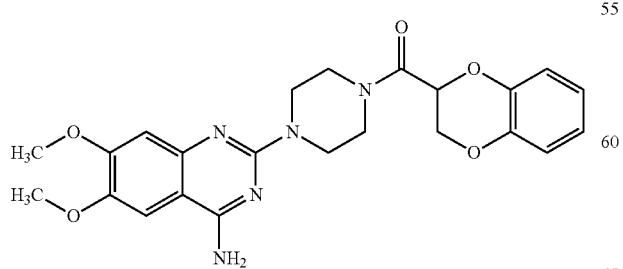

Doxazosin: U.S. Pat. No. 4,188,390

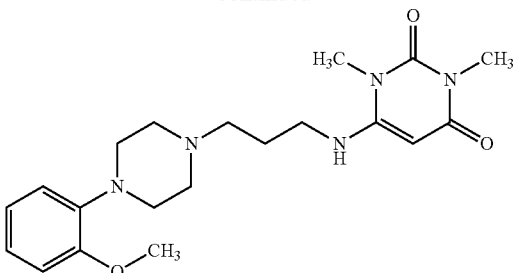

Urapidil: U.S. Pat. No. 3,957,786

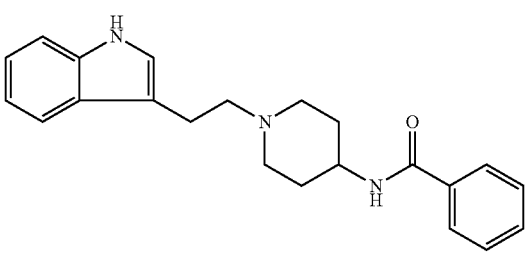

Indoramin: U.S. Pat. No. 3,527,761

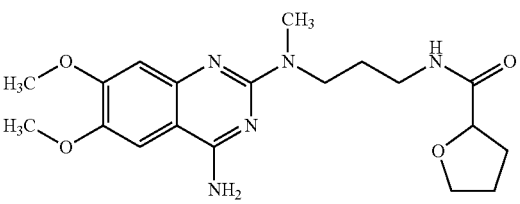

Alfuzosin: U.S. Pat. No. 4,315,007

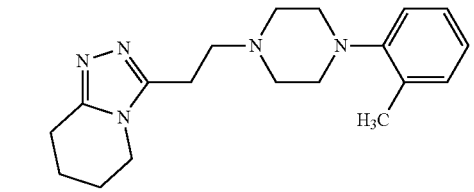

Dapiprazole: U.S. Pat. No. 4,252,721

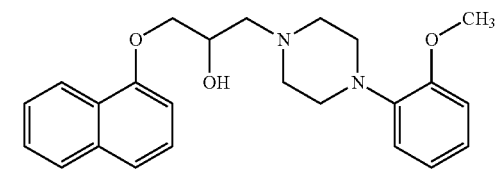

Naftopidil: U.S. Pat. No. 3,997,666

In addition, the following α-blockers are included.

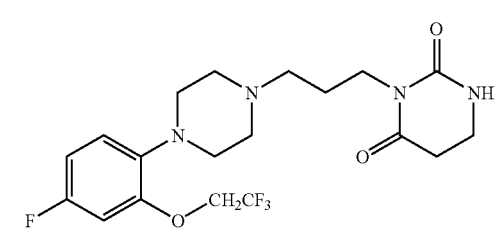

Ro 70-0004

-continued
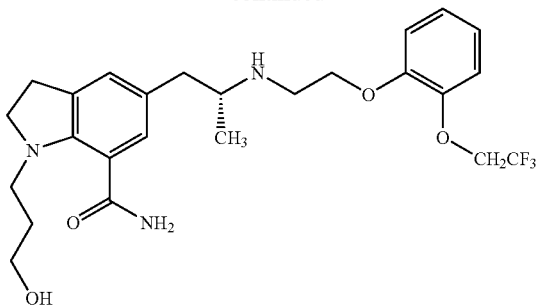
KMD-3213
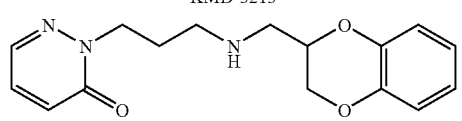
GYKI-16084
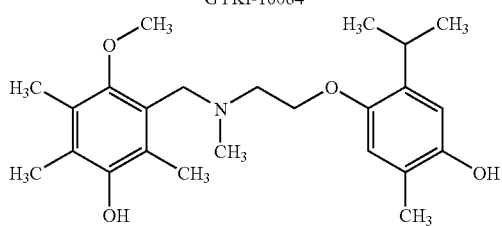
JTH-601
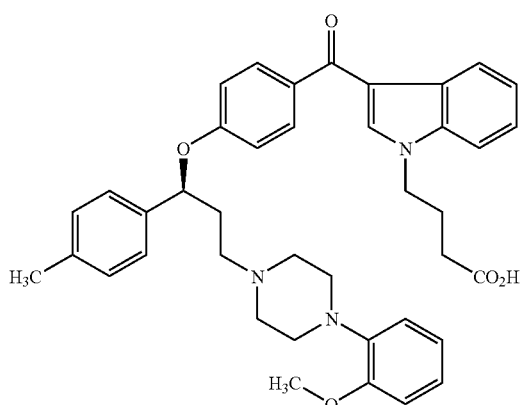
Z-350
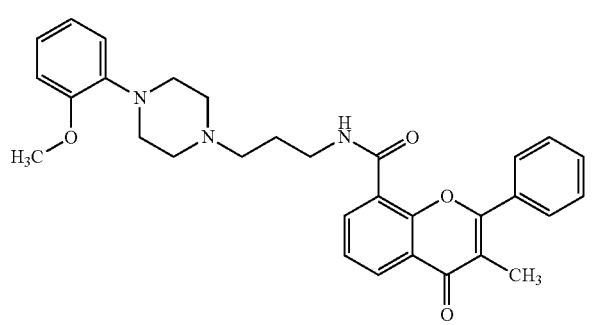
Rec-15-2739
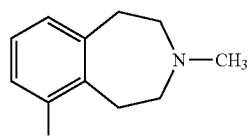
SK&F-86466
-continued
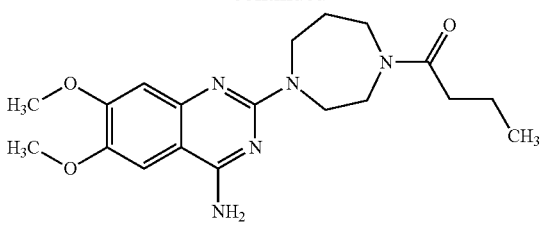
Bunazosin: U.S. Pat. No. 3,920,636
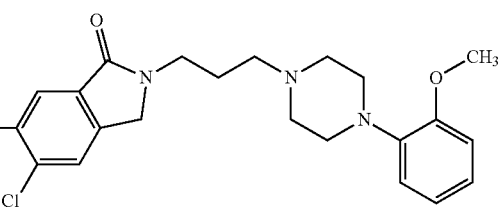
BMY-15037
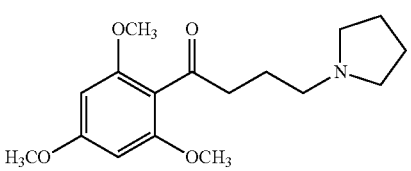
Buflomedil
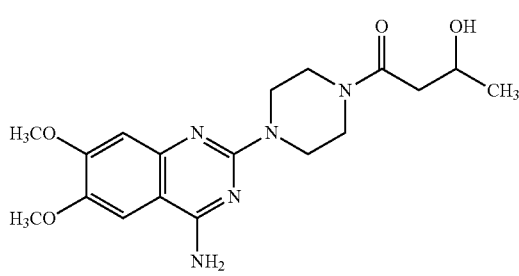
Neldazosin
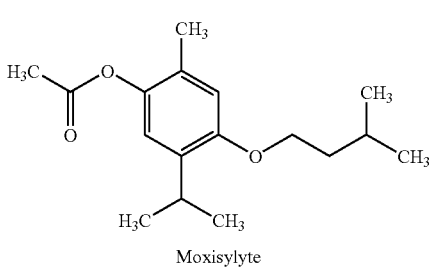
Moxisylyte
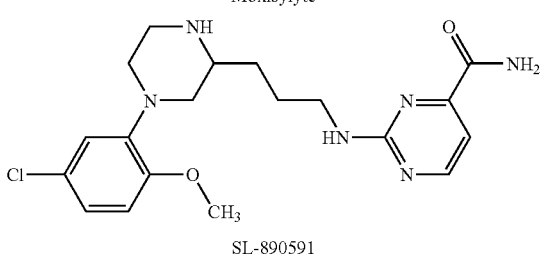
SL-890591

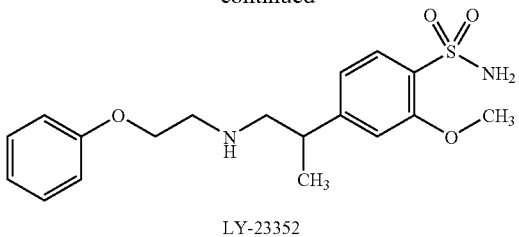

LY-23352

In addition, such α-blockers as ABT-980, AIO-8507-L, L-783308, L-780945, SL-910893, GI-231818, SK&F-106686, etc. are also included.

The crystals of the present invention have an activity to inhibit acetylcholine esterase. Therefore, the crystals of the present invention and the pharmaceutical compositions of the present invention can be used as the prophylactic and/or therapeutic agents against the senile dementia.

Also, the crystals of the present invention and the pharmaceutical compositions of the present invention can be used, for example, as agents for improving the excretory potency of urinary bladder. For instance, they can be used as the prophylactic and/or therapeutic agents against micturition disorders arising from the following 1) to 6) and the like, dysuria in particular. 1) Prostatic hypertrophy, 2) bladder neck obstruction, 3) neurogenic bladder, 4) diabetes mellitus, 5) surgery, 6) hypotonic bladder, and 7) Sjoegren's syndrome (dry eye, dry mouth, dryness of vagina, and the like).

More specifically, they can be used as the prophylactic and/or therapeutic agents against dysuria that are caused by hypotonic bladder induced by prostatic hypertrophy, hypotonic bladder induced by diabetes mellitus, hypotonic bladder induced by diabetic neuropathy, idiopathic hypotonic bladder (including age-associated hypotonic bladder), hypotonic bladder induced by multiple sclerosis, hypotonic bladder induced by Parkinson's disease, hypotonic bladder induced by spinal cord injury, postoperative hypotonic bladder, hypotonic bladder induced by brain block, neurogenic bladder induced by diabetes mellitus, neurogenic bladder induced by diabetic neuropathy, neurogenic bladder induced by multiple sclerosis, neurogenic bladder induced by Parkinson's disease, neurogenic bladder induced by spinal cord injury, neurogenic bladder induced by brain block, and the like.

Furthermore, the crystals of the present invention and the pharmaceutical compositions of the present invention can also be used as the prophylactic and/or therapeutic agents against micturition disorders such as pollakisuria, urinary incontinence, and the like.

Utilization in Combination with Another Agent

The crystals of the present invention are those of a kind of non-carbamate amine compound possessing the action to inhibit acetylcholine esterase. A non-carbamate amine compound including that for the crystals of the present invention, which possesses the action to inhibit acetylcholine esterase, can be used in combination with a drug to treat diseases inducing micturition disorders (for example, dysuria and the like) or with a drug that is administered to treat other diseases but as itself induces micturition disorders (for example, dysuria and the like).

Such a "non-carbamate amine compound possessing the action to inhibit acetylcholine esterase" may be any compound possessing the action to inhibit acetylcholine esterase and not having the carbamate structure (—OCON—) within the molecule, wherein the hydrogen atom of ammonia is substituted with a hydrocarbon group, preferably being the primary amine compound, the secondary amine compound, or the tertiary amine compound. More preferably, there are set forth compounds 1) to 49) and the like that are described in the following. Among these compounds, compounds, which have at least one 5- to 7-membered, nitrogen-containing heterocyclic ring as a partial structure, and the like are preferable, compounds 1), 20), 23), 41), and 43), which are described, hereinafter, and the like are especially preferable; and compound 1) and the like are particularly preferable.

Hereupon, because a variety of non-carbamate amine compounds described above possess the action to inhibit the acetylcholine esterase, they possess also an insecticidal action.

"A drug that treats micturition disorder-inducing diseases" is exemplified by a therapeutic agent against prostatic hypertrophy, a therapeutic agent against prostatic carcinoma, a therapeutic agent against bladder neck sclerosis, a therapeutic agent against chronic cystitis, a therapeutic agent against constipation, a therapeutic agent against colorectal cancer, a therapeutic agent against uterine cancer, a therapeutic agent against diabetes mellitus, a therapeutic agent against cerebrovascular disorders, a therapeutic agent against spinal cord injury, a therapeutic agent against spinal cord tumor, a therapeutic agent against multiple sclerosis, a therapeutic agent against dementia including Alzheimer's disease, a therapeutic agent against Parkinson's disease, a therapeutic agent against progressive supranuclear palsy, a therapeutic agent against Guillain-Barré syndrome, a therapeutic agent against acute panautonomic disorder, a therapeutic agent against olivopontocerebellar atrophy, a therapeutic agent against cervical spondylosis, or the like.

Examples of the therapeutic agent against prostatic hypertrophy include allylestrenol, chlormadinone acetate, gestonorone caproate, nomegestrol, mepartricin, finasteride, PA-109, THE-320, and the like. Also, the therapeutic agent against prostatic hypertrophy-induced micturition disorder is exemplified by α-reductase inhibitors such as YM-31758, YM-32906, KF-20405, MK-0434, finasteride, and CS-891, or the like.

Examples of the therapeutic agent against prostatic carcinoma include ifosfamide, estramustine phosphate sodium, cyproterone, chlormadinone acetate, flutamide, cisplatin, lonidamine, peplomycin, leuprorelin, finasteride, triptorelin-DDS, buserelin, goserelin-DDS, fenretinide, bicalutamide, vinorelbine, nilutamide, leuprolide-DDS, deslorelin, cetrorelix, ranpirnase, leuprorelin-DDS, satraplatin, prinomastat, exisulind, buserelin-DDS, abarelix-DDS, and the like.

Examples of the therapeutic agent against bladder neck sclerosis include α-blockers such as α-1 blockers. α-blockers include tamsulosin, prazosin, terazosin, doxazosin, urapidil, indoramin, alfuzosin, dapiprazole, naftopidil, Ro-70-0004, KMD-3213, GYKI-16084, JTH-601, Z-350, Rec-15-2739, SK&F-86466, bunazosin, BMY-15037, buflomedil, neldazosin, moxislyte, SL-890591, LY-23352, ABT-980, AIO-8507-L, L-783308, L-780945, SL-910893, GI-231818, SK&F-106686, RWJ-38063, selodosin, fiduxosin, and the like.

The therapeutic agent against chronic cystitis is exemplified by flavoxate hydrochloride or the like.

The therapeutic agent against constipation is exemplified by sennoside A and B, phenovalin, or the like.

The therapeutic agent against colorectal cancer is exemplified by chromomycin A3, fluorouracil, tegafur, krestin, or the like.

The therapeutic agent against uterine cancer is exemplified by chromomycin A3, fluorouracil, bleomycin hydrochloride, medroxyprogesterone acetate, or the like.

Examples of the therapeutic agent against diabetes mellitus include an insulin sensitizer, an insulin secretion enhancer, a biguanide, an insulin, an α-glucosidase inhibitor, a β3-adrenergic agent, and the like.

Examples of the insulin sensitizer include pioglitazone and a salt thereof (preferably hydrochloride), toroglitazone, rosiglitazone and a salt thereof (preferably maleate), JTT-501, GI-262570, MCC-555, YM-440, DRF-2593, BM-13-1258, KRP-297, CS-011, and the like.

The insulin secretion enhancer is exemplified by a sulfonylurea agent. Specific examples of said sulfonylurea agent include, for example, tolbutamide, chlorpropamide, tolazamide, acetohexamide, glyclopyramide and an ammonium salt thereof, glibenclamide, gliclazide, glimepiride, and the like. The insulin secretion enhancers other than those listed above are exemplified by repaglinide, nateglinide, KAD-1229, JTT-608, and the like.

A biguanide is exemplified by metformin, buformin, or the like.

Examples of the insulin include an animal insulin extracted from bovine and porcine pancreas; a semisynthetic insulin that is enzymatically synthesized from the insulin extracted from porcine pancreas; a human insulin synthesized by genetic engineering using *Escherichia coli* or yeast; and the like. As for the insulin, there is also used insulin zinc containing 0.4 to 0.9 (w/w) zinc; insulin zinc protamine that is produced from zinc chloride, protamine sulfate, and insulin; or the like. Furthermore, the insulin may be a fragment or derivative thereof (for example, INS-1 or the like).

The α-Glucosidase inhibitor is exemplified by acarbose, voglibose, miglitol, emiglitate, or the like.

The β3-Adrenergic agent is exemplified by AJ-9677, BMS-196085, SB-226552, SR-58611-A, CP-114271, L-755507, or the like.

The therapeutic agents against diabetes mellitus other than those listed above are exemplified by Ergoset, Pramlintide, leptin, BAY-27-9955, and the like.

Examples of the therapeutic agent against cerebrovascular disorders include nicaraven, bencyclane fumarate, eurnamonine, flunarizine, nilvadipine, ibudilast, argatroban, nizofenone, naftidrofuryl, nicergoline, nimodipine, papaveroline, alteplase, viquidil hydrochloride, moxisylyte, pentoxifylline, dihydroergotoxine mesylate, lemildipine, cyclandelate, xanthinol nicotinate, febarbamate, cinnarizine, memantine, ifenprodil, meclofenoxate hydrochloride, ebselen, clopidogrel, nebracetam, edaravone, clinprost-DDS, vatanidipine, ancrod, dipyridamole, and the like.

The therapeutic agent against spinal cord injury is exemplified by methylprednisolone, dural graft matrix, or the like.

The therapeutic agent against spinal cord tumor is exemplified by nimustine hydrochloride or the like.

The therapeutic agent against multiple sclerosis is exemplified by interferon-β-1b or the like.

Examples of the therapeutic agent against dementia including Alzheimer's disease include aniracetam, arginine pyroglutamate, nefiracetam, nimodipine, piracetam, propentfylline, vinpocetine, indeloxazine, vitamin E, cinepazide, memantine, lisuride hydrogen malate, pramiracetam, zuclopenthixol, protirelin, EGB-761, acetyl-L-carnitine, phosphatidylserine, nebracetam, taltireline, choline alphoscerate, ipidacrine, talsaclidine, cerebrolysin, rofecoxib, ST-618, T-588, tacrine, physostigmine-DDS, huperzine A, donepezil, rivastigmine, metrifonate, TAK-147, and the like.

Examples of the therapeutic agent against Parkinson's disease include talipexole, amantadine, pergolide, bromocriptine, selegiline, mazaticol hydrochloride, memantine, lisuride hydrogen malate, trihexyphenidyl, piroheptin hydrochloride, terguride, ropinirole, ganglioside-GMI, droxidopa, riluzole, gabergoline, entacapone, rasagiline, pramipexole, L-dopamethylester, tolcapone, remacemide, dihydroergocryptine, carbidopa, selegiline-DDS, apomorphine, apomorphine-DDS, etilevodopa, levodopa, and the like.

The therapeutic agent against progressive supranuclear palsy is exemplified by L-dopa, carbidopa, bromocriptine, pergolide, lisuride, amitriptyline, or the like.

The therapeutic agent against Guillain-Barré syndrome include is exemplified by a steroid agent, a TRH preparation such as protireline, or the like.

The therapeutic agent against acute panautonomic disorder is exemplified by a steroid agent, droxydopa (L-threo-DOPS), dihydroergotamine, amezinium, or the like.

The therapeutic agent against olivopontocerebellar atrophy is exemplified by a TRH preparation, a steroid agent, midodrine, amezinium, or the like.

The therapeutic agent against cervical spondylosis is exemplified by an anti-inflammatory/sedative agent or the like.

Examples of "a micturition disorder-inducing drug that is administered for the treatment of other diseases" include an analgesic agent (morphine, tramadol hydrochloride, or the like), a centrally acting muscle relaxants (baclofen or the like), a butyrophenone antipsychotic (haloperidol or the like), a therapeutic agent against pollakisuria/urinary incontinence (a muscarine antagonist such as oxybutynin chloride, propiverine hydrochloride, tolterodine, dalifenacin, YM-905/YM-537, temiverine (NS-21), KRP-197, trospium, or the like; a smooth muscle relaxant such as flavoxate hydrochloride or the like; a muscle relaxant such as NC-180 or the like; a beta2 agonist such as clenbuterol or the like; a potassium channel opener such as ZD-0947, NS-8, KW-7158, WAY-151616, or the like; a PGE2 antagonist such as ONO-8711 or the like; a vaniloid receptor agonist such as resinifera toxicin, capsaicin, or the like; a tachykinin antagonist such as TAK-637, SR-48968 (saredutant), SB-223412 (talnerant), or the like; a delta-opioid agonist; or the like), an antispasmodic agent (scopolamine butylbromide, butropium bromide, tiquizium bromide, timepidium bromide, propantheline bromide, or the like), a therapeutic agent against digestive tract ulcer (Kolantyl, Methaphyllin, cimetidine, or the like), a therapeutic agent against Parkinson's disease (trihexyphenidyl hydrochloride, biperiden, mazaticol hydrochloride, levodopa, or the like), an antihistaminic agent (diphenhydramine, chlorpheniramine maleate, homochlorcyclizine hydrochloride, or the like), a tricyclic antidepressant (imipramine hydrochloride, amitriptyline hydrochloride, clomipramine hydrochloride, amoxapine, desipramine hydrochloride, or the like), a phenothiazine antipsychotic (chlorpromazine, propericyazine, levomepromazine, thioridazine, or the like), a benzodiazepine tranquilizer/sleep inducer (diazepam, chlordiazepoxide, clotiazepam, estazolam, or the like), an antiarrhythmic agent (disopyramide or the like), a vasodilator (hydralazine hydrochloride or the like), a cerebral vasodilator (pentoxifylline or the like), a bronchodilator (theophyline, ephedrine hydrochloride, methylephedrine hydrochloride, or the like), a β-adrenergic blocker (propanol hydrochloride or the like), a common cold remedy (Danrich or the like), a peripherally acting, skeletal muscle relaxant (dantrolene sodium or the like), an antituberculous agent (isoniazid or the like), and the like.

Among these combinations, a combination of 8-[3-[1-[(3-fluorophenyl)methyl]-4-piperidinyl]-1-oxopropyl]-1,2,5,6-tetrahydro-4H-pyrrolo[3,2,1-ij]quinolin-4-one or a salt thereof and an α-blocker such as tamsulosin, prazosin, or the like is preferable.

In the case where a non-carbamate amine compound or a salt thereof is employed in combination with a drug that treats micturition disorder-inducing diseases or a micturition disorder-inducing drug, for example, (1) according to the well-known process for pharmaceutical production, a single pharmaceutical preparation is produced, as desired, together with an adequate, pharmaceutically permissible bulking agent and the like, (2) a preparation of each of the compounds and the drug is produced, as desired, together with an adequate, pharmaceutically permissible bulking agent and the like and both of the preparations are employed at the same time or with a time difference in a combination (a combined usage), or (3) both of the preparations, each of which is produced together with an adequate, pharmaceutically permissible bulking agent and the like according to a conventional process, are made in a set (a kit agent or the like) or the like. In the case of (2), the dosage times of each of the preparations may be different as far as the object of the present invention is achieved. The content amount of the active ingredient in such a preparation can be in an effective-dosage range of each active ingredient or in a pharmaceutically and pharmacologically permissible range. A specific amount is usually about 0.01 to about 100% by weight.

Formulations, Administration Routes and Dosages

The non-carbamate-type amine compounds having an acetylcholinesterase inhibiting action used in the invention, can be formulated into pharmaceutical preparations according to the per se known methods. The compounds may be formulated into pharmaceutical compositions alone or with an appropriate amount of pharmacologically acceptable carriers by properly mixing in a pharmaceutical process. Such pharmaceutical compositions include, for example, tablets (including sugar-coated tablets, film-coating tablets, etc.), powders, granules, capsules (including soft capsules), liquids and solutions, injections, suppositories, sustained release preparations; these preparations can safely be administered orally or parenterally (e.g., locally, rectally, intravenously, etc.).

In the agents for improving excretory potency of urinary bladder of the invention, the content of the non-carbamate-type amine compounds having an acetylcholinesterase-inhibiting action may be in about 0.1-about 100% by weight for the total preparation. The agent, for example, as an agent for treating difficulty of urination, may be administered orally at a dose of about 0.005-about 100 mg, preferably about 0.05-about 30 mg, more preferably about 0.2-about 10 mg, as an effective component for an adult (body weight: about 60 kg), though the dose is variable depending on the subject to be administered, route of administration, type of diseases, etc. This may be administered once a day or in several divided doses.

In the present invention, the pharmacologically acceptable carriers used in production of the agents for improving excretory potency of urinary bladder include a variety of organic or inorganic carrier materials conventionally employed as pharmaceutical materials, for example, fillers, lubricants, binders, disintegrators, etc., for solid preparations, or solvents, solubilizing agents, suspending agents, tonicity adjusting agents, buffering agents, soothing agents, etc., for liquid preparations. If required, pharmaceutical additives such as preservatives, antioxidants, coloring agents, sweeteners, adsorbents, moistening agents, and the like may be added.

The fillers include, for example, lactose, refined sugar, D-mannitol, starch, corn starch, crystalline cellulose, light anhydrous silicic acid, and the like.

The lubricants include, for example, magnesium stearate, calcium stearate, talc, colloidal silica, and the like.

The binders include, for example, crystalline cellulose, refined sugar, D-mannitol, dextrin, hydroxypropyl cellulose, hydroxypropyl methyl cellulose, polyvinylpyrrolidone, starch, sucrose, gelatin, methylcellulose, sodium carboxymethylcellulose, and the like.

The disintegrators include, for example, starch, carboxymethyl cellulose, calcium carboxymethylcellulose, sodium carboxymethyl starch, L-hydroxypropyl cellulose, and the like.

The solvents include, for example, water for injections, alcohol, propylene glycol, macrogol, sesame oil, corn oil, and the like.

The solubilizing agents include, for example, polyethylene glycol, propylene glycol, D-mannitol, benzyl benzoate, ethanol, trisaminomethane, cholesterol, triethanolamine, sodium carbonate, sodium citrate, and the like.

The suspending agents include, for example, surface activators such as stearyl triethanolamine, sodium laurylsulfate, laurylaminopropionic acid, lecithin, benzalkonium chloride, benzethonium chloride, glycerin monostearate, etc.; and hydrophilic high molecular materials such as polyvinyl alcohol, polyvinylpyrrolidone, sodium carboxymethylcellulose, methylcellulose, hydroxymethyl cellulose, hydroxyethyl cellulose, hydroxypropyl cellulose, etc.

The tonicity adjusting agents include, for example, glucose, D-sorbitol, sodium chloride, glycerin, D-mannitol, and the like.

The buffering agents include, for example, buffer solutions of phosphate, acetate, carbonate, citrate, and the like.

The soothing agents include, for example, benzyl alcohol, and the like.

The preservatives include, for example, paraoxybenzoic acid esters, chlorobutanol, benzyl alcohol, phenethyl alcohol, dehydroacetic acid, sorbic acid, and the like.

The anti-oxidants include, for example, sulfites, ascorbic acid, and the like.

The crystals of the present invention are low in the toxicity and can be employed, as they are or by formulating a pharmaceutical composition by mixing with pharmacologically permissible carriers and the like, as prophylactic and/or therapeutic drugs against a variety of diseases to be described hereinafter for a mammalian animal (for example, human, mouse, rat, rabbit, dog, cat, cattle, horse, pig, monkey, or the like).

Herein, as for the pharmacologically permissible carriers, there are used a variety of organic or inorganic carrier substances, which have been conventionally employed as formulation materials, as a bulking agent, a lubricant, a binding agent, and a disintegrator in solid formulations; a vehicle, a solubilizing agent, a suspending agent, an isotonicity agent, a buffering agent, an analgesic, and the like in liquid formulations. Also, as needed, formulation excipients such as a preservative, an antioxidant, a coloring agent, a sweetening agent, and the like can be used.

Preferred examples of the bulking agent include, for example, lactose, white soft sugar, D-mannitol, D-sorbitol, starch, pregelatinized starch, dextrin, crystalline cellulose, low-substituted hydroxypropyl cellulose, carboxymethyl cellulose sodium, gum arabic, dextrin, Pullulan, light anhydrous silicic acid, synthetic aluminum silicate, magnesium aluminometasilicate, and the like.

Preferred examples of the lubricant include, for example, magnesium stearate, calcium stearate, talc, colloidal silica, and the like.

Preferred examples of the binding agent include, for example, pregelatinized starch, sucrose, gelatin, gum arabic, methyl cellulose, carboxymethyl cellulose, carboxymethyl cellulose sodium, crystalline cellulose, white soft sugar, D-mannitol, trehalose, dextrin, Pullulan, hydroxypropyl cellulose, hydroxypropylmethyl cellulose, polyvinyl pyrrolidone, and the like.

Preferred examples of the disintegrator include, for example, lactose, white soft sugar, starch, carboxymethyl cellulose, carboxymethyl cellulose calcium, croscarmellose sodium, carboxymethyl starch sodium, light anhydrous silicic acid, low-substituted hydroxypropyl cellulose, and the like.

Preferred examples of the vehicle include, for example, water for injection, physiological saline, Ringer's solution, alcohol, propylene glycol, polyethylene glycol, sesame oil, corn oil, olive oil, cottonseed oil, and the like.

Preferred examples of the solubilizing agent include, for example, polyethylene glycol, propylene glycol, D-mannitol, trehalose, benzyl benzoate, ethanol, trisamiomethane, cholesterol, triethanolamine, sodium carbonate, sodium citrate, sodium salicylate, sodium acetate, and the like.

Preferred examples of the suspending agent include, for example, a surface active agent such as stearyltriethanolamine, sodium lauryl sulfate, laurylaminopropionic acid, lecithin, benzalkonium chloride, benzethonium chloride, glycerin monostearate, or the like; for example, a hydrophilic, high molecular substance such as polyvinyl alcohol, polyvinyl pyrrolidone, sodium carboxymethyl cellulose, methyl cellulose, hydroxymethyl cellulose, hydroxyethyl cellulose, hydroxypropyl cellulose, or the like; a polysorbate, polyoxyethylene hydrogenated castor oil, and the like.

Preferred examples of the isotonicity agent include, for example, sodium chloride, glycerin, D-mannitol, D-sorbitol, glucose, and the like.

Preferred examples of the buffering agent include, for example, a buffer solution of a phosphate, an acetate, a carbonate, a citrate, or the like and the like.

Preferred examples of the analgesic include, for example, benzyl alcohol and the like.

Preferred examples of the preservative include, for example, a paraoxybenzoic acid ester, chlorobutanol, benzyl alcohol, phenethyl alcohol, dehydroacetic acid, sorbic acid, and the like.

Preferred examples of the antioxidant include, for example, a sulfite salt, an ascorbic acid salt, and the like.

Preferred examples of the coloring agent include, for example, water-soluble food tar dyes (for examples, food dyes such as food red No. 2 and No. 3, food yellow No. 4 and No. 5, food blue No. 1 and No. 2, and the like, water-insoluble lake dyes (for examples, aluminum salts of the above-mentioned water-soluble food tar dyes and the like), natural dyes (for example, α-carotene, chlorophyll, iron oxide red, and the like), and the like.

Preferred examples of the sweetening agent include, for example, saccharin sodium, dipotassium glycyrrhizinate, aspartame, stevia, and the like.

Examples of the formulation form of the pharmaceutical composition include an oral preparation such as a tablet, a capsule (includes a soft capsule or a micro capsule), a granule, a powder, a syrup, an emulsion, a suspension, or the like; and a parental preparation such as an injection preparation (for example, a subcutaneous injection preparation, an intravenous injection preparation, an intramuscular injection preparation, an intraperitoneal injection preparation, or the like), an external preparation (for example, an intranasal dosage preparation, a transdermal preparation, an ointment preparation, or the like), a suppository preparation (for example, a rectal suppository preparation, a vaginal suppository preparation, or the like), a pellet preparation, a drip-feed preparation, and the like, where each of them are capable of being safely administered orally or parenterally.

The pharmaceutical composition can be produced according to a conventional method in the field of formulation technology, for example, a method described in The Japanese Pharmacopoeia or the like. In the following, the specific processes for production of the preparations are described in detail.

For instance, the oral preparations are produced by adding to the active ingredient, for examples, a bulking agent (for example, lactose, white soft sugar, starch, D-mannitol, or the like), a disintegrator (for example, carboxymethyl cellulose calcium or the like), a binding agent (for example, pregelatinized starch, gum arabic, carboxymethyl cellulose, hydroxypropylmethyl cellulose, polyvinyl pyrrolidone, or the like), a lubricant (for example, talc, magnesium stearate, polyethylene glycol 6000, or the like), and the like and by subjecting the resulting mixture to compression molding, as needed, followed by coating according to the well-known method by using a coating base for the purpose of masking of the taste, enteric coating, or durability.

Examples of said coating base include a sugar-coating base, a water-soluble film coating base, an enteric film coating base, a sustained-release film coating base, and the like.

As for the sugar-coating base, white soft sugar is used, which may be further used in combination with one kind or two or more kinds of materials selected from talc, precipitated calcium carbonate, gelatin, gum arabic, Pullulan, carnauba wax, and the like.

Examples of the water-soluble film coating base include a high molecular cellulose such as hydroxypropyl cellulose, hydroxypropylmethyl cellulose, to hydroxyethyl cellulose, methylhydroxyethyl cellulose, or the like; a synthetic, high molecular compound such as polyvinyl acetal diethylaminoacetate, aminoalkyl methacrylate copolymer E (Eudragit E™, Rohm Pharma Company), polyvinyl pyrrolidone, or the like; a polysaccharide such as Pullulan, and the like.

Examples of the enteric film coating base include a high molecular cellulose such as hydroxypropylmethyl cellulose phthalate, hydroxypropylmethyl cellulose acetate succinate, carboxymethylethyl cellulose, cellulose acetate phthalate, or the like; a high molecular acrylate such as methacrylate copolymer L (Eudragit L™, Rohm Pharma Company), methacrylate copolymer LD (Eudragit L-30D55™, Rohm Pharma Company), methacrylate copolymer S (Eudragit S™, Rohm Pharma Company), or the like; a natural substance such as shellac or the like, and the like.

Examples of the sustained-release film coating base include a high molecular cellulose such as ethyl cellulose or the like; a high molecular acrylate such as aminoalkyl methacrylate copolymer RS (Eudragit RS™, Rohm Pharma Company), ethyl acrylate/methyl methacrylate copolymer suspension (Eudragit NE™, Rohm Pharma Company), or the like, and the like.

The above-mentioned coating bases may be used in combination with two or more kinds of the bases in an adequate ratio. Also, a light excluding agent such as titanium oxide, iron sesquioxide, or the like may be used.

The injection preparations are produced by subjecting the active ingredient together with a dispersing agent (for example, polysorbate 80, polyoxyethylene hydrogenated castor oil 60, polyethylene glycol, carboxymethyl cellulose, sodium alginate, or the like), a preservative (for example, methylparaben, propylparaben, benzyl alcohol, chlorobutanol, phenol, or the like), an isotonicity agent (for example, sodium chloride, glycerin, D-mannitol, D-sorbitol, glucose, or the like), and the like to dissolution, suspension, or emulsion in an aqueous vehicle (for example, distilled water, physiological saline, Ringer's solution, or the like) or an oily vehicle (for example, a vegetable oil such as olive oil, sesame oil, cottonseed oil, corn oil, or the like, propylene glycol, or the like), and the like. In this case, there may be used excipients such as a solubilizing agent (for example, sodium salicylate, sodium acetate, or the like), a stabilizer (for example, human serum albumin or the like), an analgesic (for example, benzyl alcohol or the like), and the like.

The dosages of the crystals of the present invention and the pharmaceutical combination of the present invention differ depending on the administration object, the administration route, the disease, and the like, whereas, for instance, in the case where an oral preparation is administered to an adult (the body weight of about 60 kg) as a therapeutic agent against dysuria disorders, one dosage as the active ingredient is about 0.005 to about 100 mg, preferably about 0.05 to about 30 mg, more preferably about 0.2 to about 10 mg/kg of body weight, where the dosage can be administered once a day or with being divided in several times daily.

In the case where a drug is employed in a combination, the dosage can be appropriately selected depending on the administration subject, the age and the body weight of the administration subject, the symptom, the administration time, the administration method, the formulation, the combination of the drug, and the like, with reference to the minimum recommended clinical dosage of the respective drug. The dosage for a specific patient can be determined depending on the age, the body weight, the health condition, the sex, the diet, the administration time, the administration method, the excretion speed, the combination of the drug, and the degree of the condition of the disease that is treated for the patient at that time or by taking into consideration these or other factors.

Typically, respective daily dosages regarding to the combination of a non-carbamate amine compound or a salt thereof and at least one kind of compound or a salt thereof, which is selected from the therapeutic agents for a variety of diseases, are in ranges of more than about 1/50 of the minimum recommended, clinical dosage to less than the maximum recommended level regarding to the actual case where each of them is administered singly.

The invention will be explained in more detail based on the following Reference Examples, Examples, Experimental Examples, and Formulation Examples. These examples, however, are merely examples, and not intended to limit the invention.

The invention may be modified as far as the modification does not depart from the scope of the invention.

EXAMPLES INVOLVING COMPOUNDS

Reference Examples 1-30

According to per se known methods, compounds of Reference Examples 1-30 were obtained as depicted in the following Table, wherein R'=H.

TABLE 1

$$Ar-\overset{O}{\underset{\underset{R}{|}}{C}}-(CH)_n-Y$$

| Reference Example No. | Ar | R | n | Y |
|---|---|---|---|---|
| 1 | | H | 2 | |
| 2 | | H | 2 | |
| 3 | | H | 2 | |
| 4 | | H | 2 | |

TABLE 1-continued $$Ar-\overset{O}{\underset{R}{\overset{\|}{C}}}-(CH)_n-Y$$

| Reference Example No. | Ar | R | n | Y |
|---|---|---|---|---|
| 5 | [tricyclic lactam with methyl] | H | 2 | [4-methylpiperidine-CH2-4-methylphenyl] |
| 6 | [tricyclic lactam with methyl] | H | 2 | [4-methylpiperidine-CH2-3-methylphenyl] |
| 7 | [tricyclic lactam with methyl] | H | 2 | [4-methylpiperidine-CH2-2-methylphenyl] |
| 8 | [tricyclic lactam with methyl] | H | 2 | [4-methylpiperidine-CH2-4-hydroxyphenyl] |
| 9 | [tricyclic lactam with methyl] | H | 2 | [4-methylpiperidine-CH2-3-hydroxyphenyl] |
| 10 | [tricyclic lactam with methyl] | H | 2 | [4-methylpiperidine-CH2-2-methoxyphenyl] |

TABLE 2

$$Ar-\overset{O}{\underset{R}{\overset{\|}{C}}}-(CH)_n-Y$$

| Reference Example No. | Ar | R | n | Y |
|---|---|---|---|---|
| 11 | [tricyclic lactam with methyl] | H | 2 | [4-methylpiperidine-CH2-4-nitrophenyl] |

TABLE 2-continued $$Ar-\overset{O}{\underset{R}{\overset{\|}{C}}}-(CH)_n-Y$$

| Reference Example No. | Ar | R | n | Y |
|---|---|---|---|---|
| 12 | [tricyclic methyl-substituted pyrroloquinolinone] | H | 2 | [4-methylpiperidine-N-CH₂-(3-nitrophenyl)] |
| 13 | [tricyclic methyl-substituted pyrroloquinolinone] | H | 2 | [4-methylpiperidine-N-CH₂-(2-hydroxyphenyl)] |
| 14 | [tricyclic methyl-substituted pyrroloquinolinone] | H | 2 | [4-methylpiperidine-N-CH₂-(2-chlorophenyl)] |
| 15 | [tricyclic methyl-substituted pyrroloquinolinone] | H | 2 | [4-methylpiperidine-N-CH₂-(3-fluorophenyl)] |
| 16 | [tricyclic methyl-substituted pyrroloquinolinone] | H | 2 | [4-methylpiperidine-N-CH₂-(2-fluorophenyl)] |
| 17 | [tricyclic methyl-substituted pyrroloquinolinone] | H | 2 | [4-methylpiperidine-N-CH₂-phenyl] |
| 18 | [tricyclic methyl-substituted pyrroloquinolinone isomer] | H | 2 | [4-methylpiperidine-N-CH₂-phenyl] |
| 19 | [tetracyclic methyl-substituted isoindolobenzazepinone] | H | 2 | [4-methylpiperidine-N-CH₂-phenyl] |

TABLE 2-continued $$Ar-\overset{O}{\underset{R}{\overset{\|}{C}}}-(CH)_n-Y$$

| Reference Example No. | Ar | R | n | Y |
|---|---|---|---|---|
| 20 | 2-acetyl-8-methyl-2,3,4,5-tetrahydro-1H-2-benzazepine | H | 2 | 1-benzyl-4-methylpiperidine |

TABLE 3

$$Ar-\overset{O}{\underset{R}{\overset{\|}{C}}}-(CH)_n-Y$$

| Reference Example No. | Ar | R | n | Y |
|---|---|---|---|---|
| 21 | 4-benzoyl-7-methyl-2,3,4,5-tetrahydro-1,4-benzoxazepine | H | 2 | 1-benzyl-4-methylpiperidine |
| 22 | 8-methyl-2,3,4,5-tetrahydro-1H-1-benzazepine | H | 2 | 1-benzyl-4-methylpiperidine |
| 23 | 5-methylindoline | H | 2 | 1-(3-fluorobenzyl)-4-methylpiperidine |
| 24 | 1-ethyl-5-methylindoline | H | 2 | 1-benzyl-4-methylpiperidine |
| 25 | 1,7-dimethylindoline | H | 2 | 1-benzyl-4-methylpiperidine |
| 26 | 5-methylindoline | H | 2 | 1-benzyl-4-methylpiperidine |

TABLE 3-continued $$Ar-\underset{\underset{R}{|}}{C}(=O)-(CH)_n-Y$$

| Reference Example No. | Ar | R | n | Y |
|---|---|---|---|---|
| 27 | 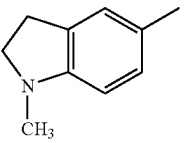 | H | 2 | 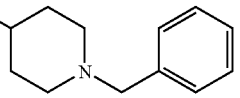 |
| 28 | 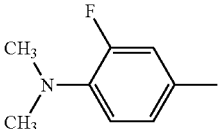 | H | 2 | 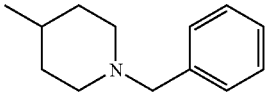 |

TABLE 4

| Reference Example No. | |
|---|---|
| 29 | 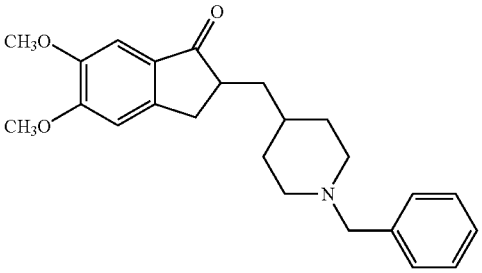 |
| 30 | 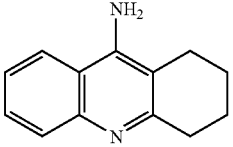 |

Reference Example 15-1

8-[3-[1-[(3-fluorophenyl)methyl]-4-piperidinyl]-1-oxopropyl]-1,2,5,6-tetrahydro-4H-pyrrolo[3,2,1-ij]quinolin-4-one (Compound of Reference Example 15)

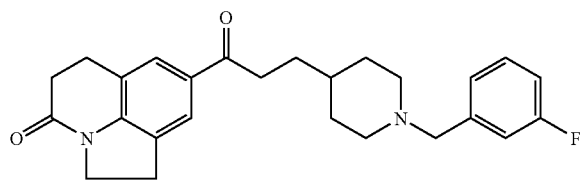

1) To thionyl chloride (300 mL) was added 3-(1-acetyl-4-piperidinyl)propionic acid (88.2 g, 0.443 mol) in small portions under ice cooling. The mixture was stirred at room temperature for 10 minutes, and then thionyl chloride was distilled off at 25° C. under reduced pressure. Diethyl ether was added to the residue and then evaporated in vacuo to give a yellow solid. Again, diethyl ether was added, and the solid was crushed with a spatula, and ether was evaporated in vacuo to give 3-(1-acetyl-4-piperidinyl)propionic acid chloride as crude light yellow powder. This light yellow powder and 1,2,5,6-tetrahydro-4H-pyrrolo[3,2,1-ij]quinolin-4-one (64.0 g, 0.369 mol) were suspended into 1,2-dichloroethane (200 mL), into which aluminum chloride (162 g, 1.21 mol) was added in small portions at room temperature. The mixture was stirred at room temperature for 12 hours, then added to ice-water, and extracted with ethyl acetate. The extract was washed with saturated brine, dried on anhydrous magnesium sulfate, and evaporated in vacuo to give a light yellow oily material. The oily material was purified by silica gel column chromatography (eluted with ethyl acetate/methanol=9:1) and crystallized from ethanol-diethyl ether to give 123.5 g of 8-[3-[(1-acetyl-4-piperidinyl)-1-oxopropyl]-1,2,5,6-tetrahydro-4H-pyrrolo[3,2,1-ij]quinolin-4-one as colorless crystals having mp. 157-159° C.

$^1$H-NMR (CDCl$_3$) δ 1.00-1.30 (2H, m), 1.50-1.95 (5H, m), 2.09 (3H, s), 2.53 (1H, dt, J=12.9, 2.4 Hz), 2.72 (2H, t, J=7.6 Hz), 2.90-3.15 (5H, m), 3.24 (2H, t, J=8.6 Hz), 3.75-3.90 (1H, m), 4.14 (2H, t, J=8.6 Hz), 4.55-4.70 (1H, m), 7.68 (1H, s), 7.73 (1H, s).

2) To 8-[3-[(1-acetyl-4-piperidinyl)-1-oxopropyl]-1,2,5,6-tetrahydro-4H-pyrrolo[3,2,1-ij]quinolin-4-one (118.7 g, 0.335 mol) obtained in 1) was added concentrated hydrochloric acid (600 mL), and the mixture was stirred at 140° C. for 4 hours. After cooling to room temperature, hydrochloric acid was distilled off under reduced pressure, and the resulting residue was made basic (pH>12) with 8N-sodium hydroxide aqueous solution and extracted with ethyl acetate. The extract was washed with saturated brine, dried on anhydrous sodium sulfate, evaporated in vacuo, and crystallized from ethyl acetate-diethyl ether to give 103.7 g of 8-[3-[(4-piperidinyl)-1-oxopropyl]-1,2,5,6-tetrahydro-4H-pyrrolo[3,2,1-ij]quinolin-4-one as colorless crystals having mp. 114-115° C.

$^1$H-NMR (CDCl$_3$) δ 1.00-1.30 (2H, m), 1.30-1.90 (7H, m), 2.59 (2H, dt, J=12.0, 2.4 Hz), 2.72 (2H, t, J=7.6 Hz), 2.85-3.15 (5H, m), 3.23 (2H, t, J=8.6 Hz), 4.14 (2H, t, J=8.6 Hz), 7.68 (1H, s), 7.73 (1H, s).

3) To a solution of 8-[3-[(4-piperidinyl)-1-oxopropyl]-1,2,5,6-tetrahydro-4H-pyrrolo[3,2,1-ij]quinolin-4-one (103.7 g, 0.332 mol)(obtained in 2)) in acetonitrile (750 mL) was added 3-fluorobenzyl bromide (65.9 g, 0.349 mol) and anhydrous potassium carbonate (80 g), and the mixture was stirred at room temperature for 12 hours. The reaction mixture was added to a mixture of ethyl acetate and water, and the organic layer was separated. The organic layer was washed with saturated brine, dried on anhydrous magnesium sulfate, and concentrated to give a light yellow oily material. The oily material was purified by silica gel column chromatography (eluted with ethyl acetate/methanol=9:1). The resulting crude crystals were recrystallized from hot ethanol to give the title compound (111.2 g) as colorless crystals having mp. 111-112° C.

$^1$H-NMR (CDCl$_3$) δ 1.20-1.50 (4H, m), 1.55-1.80 (4H, m), 1.85-2.05 (2H, m), 2.71 (2H, t, J=7.6 Hz), 2.80-3.15 (5H, m), 3.22 (2H, t, J=8.6 Hz), 3.47 (2H, s), 4.13 (2H, t, J=8.6 Hz), 6.85-7.15 (3H, m), 7.20-7.35 (1H, m), 7.67 (1H, s), 7.72 (1H, s).

Elemental analysis for C$_{26}$H$_{29}$FN$_2$O$_2$:
Calcd: C, 74.26; H, 6.95; N, 6.66.
Found: C, 74.28; H, 7.02; N, 6.58.

The above-mentioned title compound (65.4 g) was dissolved in ethanol, to which was added 1.5 equivalent of 4N-hydrochloric acid (ethyl acetate solution). The solvent and excess hydrochloric acid were distilled off to give colorless powder, which was crystallized from ethanol to give 64.1 g of the hydrochloride of title compound as colorless crystals having mp. 201-203° C. (dec.).

Elemental analysis for C$_{26}$H$_{29}$FN$_2$O$_2$.HCl:
Calcd: C, 68.34; H, 6.62; N, 6.13.
Found: C, 68.15; H, 6.66; N, 6.04.

Reference Example 15-2

8-[3-[1-(phenyl methyl)-4-piperidinyl]-1-oxopropyl]-1,2,5,6-tetrahydro-4H-pyrrolo[3,2,1-ij]quinolin-4-one (Compound of Reference Example 17)

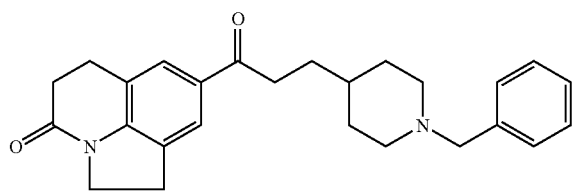

8-[3-[(4-Piperidinyl)-1-oxopropyl]-1,2,5,6-tetrahydro-4H-pyrrolo[3,2,1-ij]quinolin-4-one [obtained in section 2) of Reference Example 15-1 and benzyl bromide were treated in the same manner as in section 3) of Reference Example 15-1 to give colorless powder, which was crystallized from ether-isopropyl ether to give the title compound as colorless crystals having mp. 103-104° C.

$^1$H-NMR(CDCl$_3$) δ 1.20-1.75 (8H, m), 1.85-2.05 (2H, m), 2.71 (2H, t, J=7.6 Hz), 2.80-2.95 (3H, m), 3.02 (2H, t, J=7.6 Hz), 3.22 (2H, t, J=8.6 Hz), 3.49 (2H, s), 4.13 (2H, t, J=8.6 Hz), 7.20-7.35 (5H, m), 7.67 (1H, s), 7.71 (1H, s).

Elemental analysis for C$_{26}$H$_{30}$N$_2$O$_2$:
Calcd: C, 77.58; H, 7.51; N, 6.96.
Found: C, 77.30; H, 7.49; N, 7.20.

The above-mentioned title compound was dissolved in ethanol, to which was added 1.5 equivalent of 4N-hydrochloric acid (ethyl acetate solution). The solvent and excess hydrochloric acid were distilled off to give colorless powder, which was crystallized from ethanol to give the hydrochloride of title compound as colorless crystals having mp. 245-248° C. (dec.).

Elemental analysis for C$_{26}$H$_{30}$N$_2$O$_2$—HCl:
Calcd: C, 71.14; H, 7.12; N, 6.38.
Found: C, 70.97; H, 7.14; N, 6.18.

Formulation Example 1

Hereinafter, the hydrochloride of Compound of Reference Example 15 (8-[(3-[1-[(3-fluorophenyl)methyl]-4-piperidinyl]-1-oxopropyl]-1,2,5,6-tetrahydro-4H-pyrrolo[3,2,1-ij]-quinolin-4-one) is abbreviated to Compound A.

| | | |
|---|---|---|
| (1) | Compound A | 1 g |
| (2) | Lactose | 197 g |
| (3) | Corn starch | 50 g |
| (4) | Magnesium stearate | 2 g |

The above components (1), (2) and corn starch (20 g) were mixed, and formulated into granules with a paste prepared from corn starch (15 g) and 25 mL of water. Corn starch (15 g) and the above component (4) were added thereto, and the mixture was compressed with a compressed tablet machine to give 2000 tablets of 3 mm in diameter containing 0.5 mg/tablet of Compound A.

Formulation Example 2

| | | |
|---|---|---|
| (1) | Compound A | 2 g |
| (2) | Lactose | 197 g |
| (3) | Corn starch | 50 g |
| (4) | Magnesium stearate | 2 g |

According to the same manner as in Formulation Example 1, 2000 tablets of 3 mm in diameter containing 1.0 mg/tablet of Compound A were produced.

Formulation Example 3

| | | |
|---|---|---|
| (1) | Compound A | 5.0 mg |
| (2) | Lactose | 60.0 mg |
| (3) | Corn starch | 35.0 mg |
| (4) | gelatin | 3.0 mg |
| (5) | Magnesium stearate | 2.0 mg |

A mixture of the above components (1), (2) and (3) together with 0.03 ml of 10% gelatin aqueous solution (3.0 mg of gelation) was passed through a 1 mm mesh sieve to form granules, which were dried at 40° C. and again sieved. The resulting granules were mixed with the above component (5) and compressed. The resulting core tablets were sugar-coated with an aqueous coating suspension containing sucrose, titanium dioxide, talc and gum arabic. The coated tablets were polished with yellow beeswax to give final coated tablets.

Experimental Example 1

Measurement of Acetylcholinesterase-Inhibiting Action

Acetylcholinesterase-inhibiting action of the compounds disclosed in Reference Examples was measured using acetylcholinesterase of human erythrocyte origin according to the acetylthiocholine method (Ellman method).

Acetylcholinesterase of human erythrocyte origin (Sigma Chemical Co.) was dissolved in distilled water at a concentration of 0.2 IU/mL to give an enzyme authentic sample. To a 96-well microplate was dispensed 20 μL of drug solution, 30 μL of 80 mM Tris-HCl (pH 7.4), 50 μL of enzyme authentic sample and 50 μL of 5 mM 5,5-dithio-bis(2-nitrobenzoic acid) (Sigma Chemical Co.), and the plate was shaken for 10 seconds. Then, 50 μL of acetylthiocholine iodide (Sigma Chemical Co.) was added, and the plate was again shaken. Immediately after shaking, increase of extinction at 414 nM was measured at intervals of 30 seconds for 10 minutes. The enzyme activity was determined according to the following equation.

$$R = 5.74 \times 10^{-7} \times \Delta_A$$

(wherein R indicates an enzyme activity (mol), and $\Delta_A$ shows increase of extinction at 414 nM)

The experiment was repeated at least 3 times for each compound to obtain 50% inhibitory concentration ($IC_{50}$). Moreover, in the same manner as mentioned above, acetylcholinesterase-inhibiting activity of distigmine was measured. The following table shows the result.

TABLE 5

| Compd. No. in Reference Example (Salt) | $IC_{50}$ (nM) |
| --- | --- |
| 1 (Hydrochloride) | 13.6 |
| 4 (Hydrochloride) | 10.9 |
| 6 (Hydrochloride) | 18.9 |
| 7 (Hydrochloride) | 22.1 |
| 12 (Hydrochloride) | 8.1 |
| 13 (Hydrochloride) | 5.2 |
| 14 (Hydrochloride) | 9.9 |
| 15 (Hydrochloride) | 4.4 |
| 17 (Hydrochloride) | 7.8 |
| 18 (Hydrochloride) | 10.9 |
| Distigmine | 723.3 |

From the above results, it is found that Compounds (I) exhibit a potent acetylcholinesterase-inhibiting action.

Experimental Example 2

Potentiation Effect of the Compounds Disclosed in Reference Examples for Rhythmic Contraction of Urinary Bladder in Guinea Pig Potentiation effect of the compounds disclosed in Reference Examples for rhythmic contraction of urinary bladder was examined using Hartley male guinea pigs. Hartley male guinea pigs (SLC) weighing about 300 g were anesthetized with urethane (1.2 g/kg, i.p.), held, and incised at the midline of abdomen to expose the bladder. The urethra was ligated, and a polyethylene tube (PE-50) was inserted into the bladder. The internal pressure of the bladder was measured with a blood pressure amplifier (Nippon Koden), and the data was collected on a personal computer through an A/D converter (MP-30, Biopac Systems). A proper amount of physiological saline was injected into the bladder through a cannula to induce rhythmic contraction of the to bladder. To the animals in which occurrence of stable rhythmic contraction was confirmed at a rate of 1 time every 2 minutes to 10 minutes, a solution of the test compound dissolved in distilled water was injected intravenously, and the effect was observed.

The data was manipulated according to the following process.

The area (AUC) that is formed by a curve of the internal pressure of the bladder and a base line was calculated through analytical software (Studentlab pro 2.1.5, Biopac Systems) to evaluate the effect of the test compounds. The curve of the internal pressure is made based on the bladder contraction immediately before administration of the test compound and the first contraction 5 minutes after the administration. From the dose-dependent curve of AUC, the dose at which AUC before drug administration was increased 2 times (AUC200) was calculated to determine potency of contraction-enhancing effect of the test compounds for the muscle of urinary bladder. In addition, the potency of contraction-enhancing effect of stigmine for the muscle of bladder was determined in the same manner as mentioned above.

The following table shows the AUC200 values of each compound.

TABLE 6

| Compd. No. in Reference Example (Salt) | AUC200 (mg/kg, i.v.) |
| --- | --- |
| 1 (Hydrochloride) | 0.005 |
| 2 (Hydrochloride) | 0.059 |
| 3 (Hydrochloride) | 0.14 |
| 4 (Hydrochloride) | 0.005 |
| 5 (Hydrochloride) | 0.06 |
| 6 (Hydrochloride) | 0.0049 |
| 7 (Hydrochloride) | 0.0055 |
| 8 (Hydrochloride) | 0.076 |
| 9 (Hydrochloride) | 0.027 |
| 10 (Hydrochloride) | 0.031 |
| 11 (Hydrochloride) | 0.12 |
| 12 (Hydrochloride) | 0.006 |
| 13 (Hydrochloride) | 0.0013 |
| 14 (Hydrochloride) | 0.0016 |
| 15 (Hydrochloride) | 0.0013 |
| 16 (Hydrochloride) | 0.015 |
| 17 (Hydrochloride) | 0.0034 |
| 18 (Hydrochloride) | 0.0051 |
| 19 (Hydrochloride) | 0.065 |
| 20 (Hydrochloride) | 0.065 |
| 21 (Hydrochloride) | 0.19 |
| 22 (Fumarate) | 0.16 |
| 23 (Fumarate) | 0.073 |
| 24 (Fumarate) | 0.18 |
| 25 (Fumarate) | 0.13 |
| 26 (Fumarate) | 0.082 |
| 27 (Fumarate) | 0.1 |
| 28 (Fumarate) | 0.16 |
| 29 (Hydrochloride) | 0.16 |
| Distigmine | 0.1 |

From the above results, it is found that Compounds (I) exhibit a high potentiation effect for rhythmic contraction of urinary bladder.

Experimental Example 3

Effect on Urination Efficiency in Guinea Pigs

Effect of the compounds of Reference Examples on urination efficiency was examined using Hartley male guinea pigs. Six to ten Hartley male guinea pigs weighing 346.5±3.5 g (SLC) were employed in each treated group. Guinea pigs were anesthetized with urethane, and held, and the bladder was exposed. Two polyethylene tubes (PE-50 and PE-100) were inserted into the bladder. One (PE-50) of the tubes was used in infusion of physiological saline, and the other (PE-100) was used for measurement of the internal pressure of the bladder. Saline was infused continuously at a flow rate of 0.3 mL/min. The infusion was stopped at the time when intermittent urination was confirmed at least 3 times, and the whole saline in bladder was removed. Again, infusion was started, and stopped at the time when a rise of the pressure in bladder was confirmed immediately before urination, and the time required for infusion and the weight of excreted urine were measured. Efficiency of urination was calculated from the following equation.

Efficiency of urination (%)=100×Excreted volume (mL)/Infusion time (min)×0.3 (mL/min)

Measurement was made at least 2 times before administration of the test compound, and then the test compound was dissolved in distilled water and administered intravenously. As for distigmine, the value was measured 30 minutes after administration, and as for the compounds of Reference Examples, the measurement was made 10 minutes after administration. Effect by administration of solvents was also confirmed.

The average measured value before administration of the test compounds was regarded as the value before administration, and applied to the paired-t test for a significant difference test with the value after the administration. (** $p<0.01$, * $p<0.05$)

The following table shows the effect on efficiency of urination.

TABLE 7

| Compound | Dose (mg/kg) | Efficiency of Urination (%) Before adm. | After adm. | Improvement of Efficiency (%) |
|---|---|---|---|---|
| Vehicle | — | 77.4 ± 6.4 | 78.4 ± 6.5 | 2.4 |
| Distigmine | 0.1 | 79.1 ± 5.7 | 90.9 ± 2.7 | 20.4 |
| Distigmine | 0.3 | 67.4 ± 4.3 | 75.3 ± 3.7 | 14.7 |
| Distigmine | 1 | 78.6 ± 6.7 | 67.8 ± 4.6 | −11.6 |
| Distigmine | 3 | 68.6 ± 7.0 | 48.1 ± 8.5 | −30.9** |
| Vehicle | — | 77.4 ± 6.4 | 82.8 ± 4.7 | 12.9 |
| Compd. of Ref. Ex. 15 | 0.003 | 71.5 ± 7.9 | 79.6 ± 6.4 | 16.2 |
| Compd. of Ref. Ex. 15 | 0.01 | 60.0 ± 7.7 | 93.9 ± 3.0 | 77.0** |
| Compd. of Ref. Ex. 15 | 0.03 | 65.5 ± 9.0 | 88.9 ± 3.1 | 66.2* |
| Vehicle | — | 78.5 ± 6.0 | 73.7 ± 8.9 | −7.1 |
| Compd. of Ref. Ex. 30 | 0.3 | 62.2 ± 5.1 | 74.5 ± 5.1 | 22.0** |
| Compd. of Ref. Ex. 30 | 1.0 | 62.8 ± 7.8 | 84.9 ± 4.8 | 55.4* |
| Compd. of Ref. Ex. 30 | 3.0 | 65.8 ± 8.9 | 89.0 ± 2.7 | 64.2* |

TABLE 7-continued

| Compound | Dose (mg/kg) | Efficiency of Urination (%) Before adm. | After adm. | Improvement of Efficiency (%) |
|---|---|---|---|---|

**$p<0.01$,
*$p<0.05$

From the above results, it is found that improvement of urination efficiency by distigmine is poor and it makes the efficiency worse at a high dose, while Compounds (I) improve the efficiency greatly and significantly, and do not make the efficiency worse even at high doses.

Experimental Example 4

Effect on the Flow Rate of Urine in Guinea Pigs

Effect on the flow rate of urine by single or combined use of Compounds of Reference Examples, distigmine, prazosin, and tamsulosin was examined using Hartley male guinea pigs. Four to six Hartley male guinea pigs weighing about 350 g (SLC) were employed in each treated group. Guinea pigs were anesthetized with urethane, and held, and the bladder was exposed. Two polyethylene tubes (PE-100) were inserted into the bladder. One of the tubes was used in infusion of physiological saline, and the other used for measurement of the internal pressure of the bladder. Saline was infused continuously at a flow rate of 0.3 mL/min. The infusion was stopped at the time when intermittent urination was confirmed at least 3 times, and the whole saline in bladder was removed. Again, infusion was started, and stopped at the time when a rise of the pressure in bladder was confirmed immediately before urination. Excreted urine was weighed on an electronic force balance (HX-400, A&D). Analogue data of the internal pressure of the bladder and urine weight were input in an AD converter (MP-30, Biopac Systems) and the digital signal was analyzed by means of purpose-made software (Student lab pro 2.1.5, Biopac Systems). Sampling interval of the date was fixed at 0.1 second, and the value of urine weight was differentiated to determine the flow rate of urine. In order to remove data noise of the excretion volume and flow rate of urine, the data was adapted to a lowcut filter at 0.5 Hz.

Measurement was made 2 times before administration of the test compound, and then the test compound was administered intravenously. Again, measurement was made 10 minutes after administration of the test compound. Effect by administration of solvents was also confirmed as a control experiment.

The average measured value before administration of the test compounds was regarded as the value before administration, and the rate of change of the values from the ante-administration to the post-administration was calculated to compare between the groups by means of the Dunnet's test.

Effect on the flow rate of urine is summarized in the following table.

TABLE 8

| | Dose (mg/kg) | n | Flow Rate (mL/sec) Ante-admn. | Post-admn. | Improvement (%) |
|---|---|---|---|---|---|
| DMSO (Control) | — | 5 | 0.34 ± 0.05 | 0.30 ± 0.05 | −13.85 ± 6.48 |
| Prazosin | 0.1 | 5 | 0.18 ± 0.03 | 0.17 ± 0.02 | 0.97 ± 10.32 |
| Distigmine | 1.0 | 6 | 0.25 ± 0.05 | 0.22 ± 0.05 | −8.31 ± 11.13 |
| Distigmine + | 1.0 | 4 | 0.30 ± 0.07 | 0.25 ± 0.09 | −24.17 ± 12.31 |

TABLE 8-continued

| | Dose (mg/kg) | n | Flow Rate (mL/sec) | | Improvement (%) |
| --- | --- | --- | --- | --- | --- |
| | | | Ante-admn. | Post-admn. | |
| Prazosin | 0.1 | | | | |
| Compd. of Ref. Ex. 15 | 0.01 | 5 | 0.27 ± 0.03 | 0.29 ± 0.05 | 6.81 ± 7.84 |
| Compd. of Ref. Ex. 15 + Prazosin | 0.01 0.1 | 5 | 0.180 ± 0.01 | 0.25 ± 0.03 | 42.37 ± 15.25** |

**p < 0.01 vs DMSO (Control)

TABLE 9

| | Dose (mg/kg) | Flow Rate (mL/sec) | | Improvement (%) |
| --- | --- | --- | --- | --- |
| | | Ante-admn. | Post-admn. | |
| Distilled Water (Control) | — | 11 0.16 ± 0.01 | 0.12 ± 0.01 | −22.0 ± 6.5 |
| Tamsulosin | 0.1 | 11 0.16 ± 0.01 | 0.14 ± 0.02 | −11.8 ± 4.8 |
| Compd. of Ref. Ex. 15 | 0.001 | 9 0.17 ± 0.03 | 0.15 ± 0.02 | −6.5 ± 12.1 |
| Compd. of Ref. Ex. 15 + Tamsulosin | 0.001 0.1 | 10 0.15 ± 0.01 | 0.16 ± 0.01 | 11.3 ± 9.2* |

*p < 0.05 vs distilled water (Control)

From the above result, it is found that improvement of the flow rate of urine by distigmine alone is poor and not enhanced even in combination with an α-blocker prazosin. On the other hand, it is recognized that Compound (I) per se improves the flow rate of urine, which is further increased considerably in combination with α-blockers, prazosin and tamsulosin.

From the result of the above-mentioned Experimental Examples 2, 3 and 4, it is found that non-carbamate-type amine compounds showing an acetylcholinesterase-inhibiting action, particularly, Compounds (I) have a potent effect for improving excretory potency of the urinary bladder.

Examples Involving Crystals

The following Examples are drawn to the embodiments of the present invention involving crystals. The melting points were measured by using a Type-535 melting point apparatus produced by Buechi Company and a NP-500D apparatus manufactured by Yanako Kiki Kailiatsu Kenkyusyo Kabushiki Kaisya. The data on the powder X-ray crystal diffractometry are determined by using Type-RINT 1100 (Rigalcu Denki Kabushiki Kaisya) using the Cu—Kα radiation as the radiation source. Also, in the following Reference Examples and Examples, % indicates the percent by weight, unless otherwise specified.

Reference Example 31

8-[3-(4-Piperidinyl)-1-oxopropyl]-1,2,5,6-tetrahydro-4H-pyrrolo[3,2,1-ij]quinolin-4-one

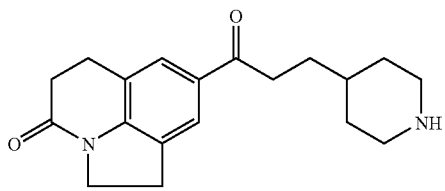

1) Into thionyl chloride (300 ml) was added 3-(1-acetyl-4-piperidinyl)propionic acid (88.2 g, 0.443 mol) in small portions under ice cooling. After the resulting mixture was stirred at room temperature for 10 minutes, the thionyl chloride was evaporated under reduced pressure at 25° C. The resulting residue was mixed with diethyl ether and was evaporated under reduced pressure to leave a yellow solid residue. An additional diethyl ether was added to the residue and the solid substance was subjected to pulverization by the use of a spatula, followed by evaporation under reduced pressure to obtain a crude product of 3-(1-acetyl-4-piperidinyl)propionyl chloride as a yellow powder. To a suspension of this yellow powder and 1,2,5,6-tetrahydro-4H-pyrrolo[3,2,1-ij]quinoline-4-one (64.0 g, 0.369 mol) in 1,2-dichloroethane (200 ml) was added aluminum chloride (162 g, 1.21 mol) in small portions at room temperature. After stirring at room temperature for 12 hours, the reaction mixture was poured into ice water and extracted with ethyl acetate. The extract was washed with a saturated aqueous solution of sodium chloride, dried with anhydrous magnesium sulfate, and then evaporated under reduced pressure to remove the solvents, thereby obtaining an oily pale yellow substance. This oily substance was purified by column chromatography on silica gel (eluent: ethyl acetate-methanol=9:1) and crystallization from ethanol and diethyl ether to obtain 123 g of 8-[3-(1-acetyl-4-piperidinyl)-1-oxopropyl]-1,2,5,6-tetrahydro-4H-pyrrolo-[3,2,1-ij]quinolin-4-one, as colorless crystals having the melting point of 157-159° C.

$^1$HNMR (CDCl$_3$) δ 1.00-1.30 (2H, m), 1.50-1.95 (5H, m), 2.09 (3H, s), 2.53 (1H dt, J=12.9, 2.4 Hz), 2.72 (2H, t, J=7.6 Hz), 2.90-3.15 (5H, m), 3.24 (2H, t, J=8.6 Hz), 3.75-3.90 (1H m), 4.14 (2H, t, J=8.6 Hz), 4.55-4.70 (1H, m), 7.68 (1H, s), 7.73 (1H, s).

Elemental Analysis for C$_{21}$H$_{26}$N$_2$O$_3$,

Calcd.: C, 71.16; H, 7.39; N, 7.90.

Found: C, 71.12; H, 7.18; N, 7.80.

2) To 8-[3-(1-acetyl-4-piperidinyl)-1-oxopropyl]-1,2,5,6-tetrahydro-4H-pyrrolo-[3,2,1-ij]quinolin-4-one (118.7 g, 0.335 mol), which was obtained in 1), was added 37% hydrochloric acid (600 ml) and the resulting mixture was stirred at 140° C. for 4 hours. After cooling to room temperature, hydrochloric acid was evaporated under reduced pressure and the resulting residue was basified (pH 12) with an 8N aqueous solution of sodium hydroxide and extracted with ethyl acetate. The extract was washed with a saturated aqueous solution of sodium chloride, dried with anhydrous sodium sulfate, and concentrated under reduced pressure to remove the solvent. The residue was crystallized from ethyl acetate and diethyl ether to obtain 103.7 g of the title compound as colorless crystals having the melting point of 114-115° C.

$^1$H NMR (CDCl$_3$) δ 1.00-1.30 (2H, m), 1.30-1.90 (7H, m), 2.59 (2H, dt, J=12.0, 2.4 Hz), 2.72 (2H, t, J=7.6 Hz), 2.85-3.15 (5H, m), 3.23 (2H, t, J=8.6 Hz), 4.14 (2H, t, J=8.6 Hz), 7.68 (1H, s), 7.73 (1H, s).

Elemental Analysis for C$_{19}$H$_{24}$N$_2$O$_2$,
Calcd.: C, 73.05; H, 7.74; N, 8.97.
Found: C, 72.96; H, 7.48; N, 9.15.

Reference Example 32

8-[2-fluoro-3-[1-[(3-fluorophenyl)methyl]-4-piperidinyl]-1-oxopropyl]-1,2,5,6-tetrahydro-4H-pyrrolo[3,2,1-ij]quinolin-4-one

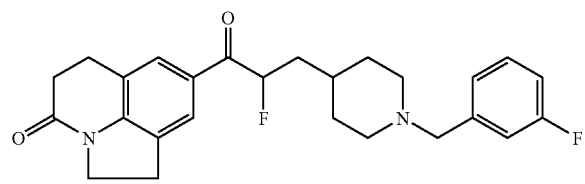

Into a nitrogen-flushed, three-necked flask, a solution of 1,1,1,3,3,3-hexamethyldisilazane (1.38 g, 8.60 mmol) in tetrahydrofuran (50 ml) was placed and the resulting mixture was cooled in a dry ice/acetone bath. Thereto was added dropwise a solution of n-butyl lithium in hexane (1.6 M)(5.4 ml, 8.6 mmol) and then the resulting solution was stirred at −20° C. for 10 minutes. To this solution, which was cooled again in a dry ice/acetone bath, was added dropwise a solution of 8-[3-[1-[(3-fluorophenyl)methyl]-4-piperidinyl]-1-oxopropyl]-1,2,5,6-tetrahydro-4H-pyrrolo-[3,2,1-ij]quinolin-4-one (3.0 g, 7.1 mol), which was obtained in Example 1, in tetrahydrofuran (20 ml). The resulting mixture was stirred at −20° C. for 20 minutes and then cooled again in a dry ice/acetone bath. To this solution was added dropwise a solution of N-fluorobenzenesulfonimide (1.38 g, 8.6 mmol) in tetrahydrofuran (20) and the temperature was gradually raised to room temperature. The reaction mixture was mixed with water and was extracted with ethyl acetate. Then, the organic layer was washed with a saturated aqueous solution of sodium chloride, dried with anhydrous sodium sulfate, and concentrated to remove the solvent. The resulting residue was purified by column chromatography on silica gel (eluent: ethyl acetate) to obtain of the title substance as a colorless oily substance (42 mg).

$^1$HNMR (300 MHz, CDCl$_3$) δ 1.20-1.40 (3H, m), 1.60-1.80 (4H, m), 1.85-2.00 (2H, m), 2.80-2.95 (2H, m), 2.93 (2H, t, J=7.5 Hz), 3.25-3.45 (4H, m), 3.47 (2H, s), 4.18 (2H, t, J=8.7 Hz), 5.21 (1H, dt, J=46.5, 6.6 Hz), 6.90-7.10 (3H, m), 7.20-7.30 (1H, m), 7.73 (1H, s), 7.76 (1H, s).

Example 1

8-[3-[1-[(3-fluorophenyl)-methyl]-4-piperidinyl]-1-oxopropyl]-1,2,5,6-tetrahydro-4H-pyrrolo-[3,2,1-ij]quinolin-4-one

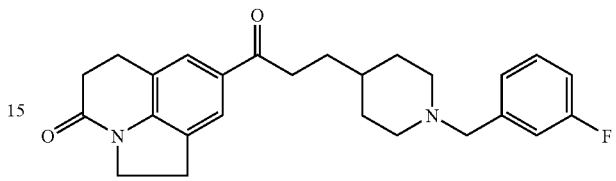

To a solution of 8-[3-(4-piperidinyl)-1-oxopropyl]-1,2,5,6-tetrahydro-4H-pyrrolo-[3,2,1-ij]quinolin-4-one (103.7 g, 0.332 mol) in acetonitrile (750 ml), which was obtained in Reference Example 31, were added 3-fluorobenzyl bromide (65.9 g, 0.349 mol) and anhydrous potassium carbonate (80 g) and the resulting solution was stirred at room temperature for 12 hours. The reaction solution was concentrated and poured into a solvent mixture of ethyl acetate (250 ml), tetrahydrofuran (250 ml), and water (200 ml). The organic layer was separated and the aqueous layer was extracted twice with a solvent mixture of ethyl acetate (80 ml) and tetrahydrofuran (50 ml). The combined organic layers were washed with a saturated aqueous solution of sodium chloride (150 ml), dried with anhydrous magnesium sulfate, and then concentrated under reduced pressure to obtain of crude colorless crystals (130.6 g). A half amount of the crude crystals was dissolved into a solvent mixture of ethyl acetate (140 ml), methanol (10 ml), and chloroform (150 ml) with heating at 40° C. and purified by column chromatography on silica gel (silica gel: 300 g, eluent: ethyl acetate-methanol=10:1). The same step was repeated to obtain crude crystals in a total amount of 115.4 g. To 115.4 g of the thus-obtained crystals was added ethanol (500 ml) and the resulting mixture was heated to reflux with stirring until it became a homogeneous solution. Ethanol (250 ml) was evaporated under an atmospheric pressure with heating and then the heating was stopped to gradually cool the mixture with stirring for 6 hours. The precipitated crystals were collected by filtration, washed with cold ethanol (250 ml), and then dried at room temperature to obtain 111.3 g of the title compound as colorless crystals having the melting point of 114-117° C. Its X-ray powder diffraction pattern was shown in FIG. 1.

$^1$HNMR (CDCl$_3$) δ 1.20-1.50 (4H, m), 1.55-1.80 (4H, m), 1.85-2.05 (2H, m), 2.71 (2H, t, J=7.6 Hz), 2.80-3.15 (5H, m), 3.22 (2H, t, J=8.6 Hz), 3.47 (2H, s), 4.13 (2H, t, J=8.6 Hz), 6.85-7.15 (3H, m), 7.20-7.35 (1H, m), 7.67 (1H, s), 7.72 (1H, s).

Elemental analysis for C$_{26}$H$_{29}$N$_2$O$_2$,
Calcd.: C, 74.26; H, 6.95; N, 6.66.
Found: C, 74.28; H, 7.02; N, 6.58.
Data of X-ray powder diffraction analysis

| Diffraction angle: 2 θ(°) (angstrom) | Spacing: d value |
|---|---|
| 5.08 | 17.4 |
| 10.2 | 8.68 |

| Diffraction angle: 2 θ(°) (angstrom) | Spacing: d value |
|---|---|
| 16.8 | 5.27 |
| 17.8 | 4.97 |
| 18.6 | 4.76 |
| 20.6 | 4.31 |
| 23.1 | 3.85 |

Formulation Example 4

| (1) Crystals in Example 1 | 1 g |
|---|---|
| (2) Lactose | 197 g |
| (3) Corn starch | 50 g |
| (4) Magnesium stearate | 2 g |

The above-described (1), (2), and corn starch (20 g) were compounded and granulated together with a paste prepared from corn starch (15 g) and 25 ml of water. To the granules were added corn starch (15 g) and the above-described (4) and the resulting mixture was pressed by the use of a compressed tablet making machine to produce 2,000 tablets of 3 mm in diameter, each of which contains 0.5 mg of the crystals obtained in Example 1.

Formulation Example 5

| (1) | Crystals obtained in Example 1 | 2 g |
|---|---|---|
| (2) | Lactose | 197 g |
| (3) | Corn starch | 50 g |
| (4) | Magnesium stearate | 2 g |

According to a procedure similar to that used in Formulation Example 4, there were prepared 2,000 tablets of 3 mm in diameter, each of which contains 1.0 mg of the crystals obtained in Example 1.

Formulation Example 6

| (1) | Crystals in Example 1 | 5.0 mg |
|---|---|---|
| (2) | Lactose | 60.0 mg |
| (3) | Corn starch | 35.0 mg |
| (4) | Gelatin | 3.0 mg |
| (5) | Magnesium stearate | 2.0 mg |

By the use of 0.03 ml of a 10% aqueous solution of gelatin (containing 3.0 mg of gelatin), a mixture of the above-described substances (1), (2), and (3) was granulated by passing through a sieve with a 1-mm mesh and the resulting granules were dried at 40° C. and then sieved again. The thus-obtained granules were mixed with the above-described (5) and pressed. The thus-obtained core tablets were sugar-coated by treatment with a suspension of sucrose, titanium dioxide, talc, and gum arabic in water. The resulting sugar-coated tablets were glazed with wax to obtain the coated tablets.

Experimental Example 5

Determination of the Activity to Inhibit the Acetylcholine Esterase

The activity to inhibit the acetylcholine esterase of the crystals obtained in Example 1 was determined according to the acetylthiocholine method (the Ellman method) by the use of a human erythrocyte-derived acetylcholine esterase.

A human erythrocyte-derived acetylcholine esterase (Sigma Chemical Company) was dissolved into distilled water to obtain a standard enzyme preparation with an enzyme concentration of 0.2 IU/mL. To a 96-well titer plate were dispensed 20 μl of the drug-containing solution, 30 μl of an 80-mM solution of Tris-HCl (pH 7.4), 50 μl of the standard enzyme preparation, and 50 μl of a 5-mM solution of 5,5-dithio-bis(2-nitrobenzoic acid) (Sigma Chemical Company) and the microplate was shaken for 10 seconds. As soon as 50 μl of a 4-mM solution of acetylthiocholine iodide (Sigma Chemical Company) was added and shaking was started again, every increment in According to a procedure similar to that used in Formulation Example 4, there were prepared 2,000 tablets of 3 mm in diameter, each of which contains 1.0 mg of the crystals obtained in Example 1.

Formulation Example 6

| (1) | Crystals in Example 1 | 5.0 mg |
|---|---|---|
| (2) | Lactose | 60.0 mg |
| (3) | Corn starch | 35.0 mg |
| (4) | Gelatin | 3.0 mg |
| (5) | Magnesium stearate | 2.0 mg |

By the use of 0.03 ml of a 10% aqueous solution of gelatin (containing 3.0 mg of gelatin), a mixture of the above-described substances (1), (2), and (3) was granulated by passing through a sieve with a 1-mm mesh and the resulting granules were dried at 40° C. and then sieved again. The thus-obtained granules were mixed with the above-described (5) and pressed. The thus-obtained core tablets were sugar-coated by treatment with a suspension of sucrose, titanium dioxide, talc, and gum arabic in water. The resulting sugar-coated tablets were glazed with wax to obtain the coated tablets.

Experimental Example 5

Determination of the Activity to Inhibit the Acetylcholine Esterase

The activity to inhibit the acetylcholine esterase of the crystals obtained in Example 1 was determined according to the acetylthiocholine method (the Ellman method) by the use of a human erythrocyte-derived acetylcholine esterase.

A human erythrocyte-derived acetylcholine esterase (Sigma Chemical Company) was dissolved into distilled water to obtain a standard enzyme preparation with an enzyme concentration of 0.2 IU/mL. To a 96-well titer plate were dispensed 20 μl of the drug-containing solution, 30 μl of an 80-mM solution of Tris-HCl (pH 7.4), 50 μl of the standard enzyme preparation, and 50 μl of a 5-mM solution of 5,5-dithio-bis(2-nitrobenzoic acid) (Sigma Chemical Company) and the microplate was shaken for 10 seconds. As soon as 50 μl of a 4-mM solution of acetylthiocholine iodide (Sigma Chemical Company) was added and shaking was started again, every increment in absorbance at the wavelength of 414 nm at an interval of 30 seconds was determined for 10 minutes.

$$R=5.74\times10^{-7}\times\Delta_A$$

(wherein R indicates an enzyme activity (mol) and $\Delta_A$ indicates an increment in absorbance at the wavelength of 414 nM). The experiment was repeated at least three times with each compound to determine the 50% inhibitory concentration ($IC_{50}$). Furthermore, the activity to inhibit the acetylcholine esterase of distigmine was determined in a manner similar to that described in the above method. The results obtained are shown in the following Table.

| Compounds | $IC_{50}$ (nM) |
|---|---|
| Example 1 | 6.6 |
| Distigmine | 651.9 |

The results described above reveal that the crystals of the present invention possess an excellent activity to inhibit the acetylcholine esterase.

Experimental Example 6

Hygroscopicity Test

In weighing vessels, 0.3 g of the crystals, which were obtained in Example 1, was weighed and the vessels were stored for the period of 14 days in the desiccators of the relative humidity (RH) of 75% (a saturated aqueous solution of sodium chloride) and of 93% (a saturated aqueous solution of potassium nitrate), with the vessels being opened. After this period, the percent changes in the weight were determined. The results obtained are shown in the following table.

| | Percent change in weight (%) | |
|---|---|---|
| Period of storage (days) | 25° C./75% RH | 25° C./93% RH |
| 4 | +0.11 | +0.06 |
| 7 | +0.11 | +0.09 |
| 14 | +0.18 | +0.15 |

The results described above reveal that no changes were observed in the weight of the crystals of the present invention, thereby proving a nonhygroscopic property of the crystals.

In addition, the X-ray powder diffraction images of the crystals remained almost the same before and after their storage, thereby proving a persistence of the crystal form of the crystals.

Experimental Example 7

Stability Test

A number of specimens of the crystals obtained in Example 1 were stored under the following conditions and then their changes in the property and the remaining percent were determined.
Storing conditions: 1. 60° C. for 3 months (in a brown glass bottle, closed); 2. 45° C., the relative humidity of 75% for 3 months (in a brown glass bottle, closed); 3. 40° C., the to relative humidity of 75% for 3 months (in a brown glass bottle, opened); 4. irradiated with a xenon lamp (60000 lux) for 20 hours (1.2 million lux/hour) (on a Petri dish covered with a polyvinylidene chloride film).

The results obtained are shown in the following table.

| Storing condition | Property | Remaining percent (%) |
|---|---|---|
| 1 (60° C./3 months) | white crystals | 99.8 |
| 2 (40° C./75% RH, closed) | white crystals | 101.6 |
| 3 (40° C./75% RH, open) | white crystals | 100.2 |
| 4 (Xenon lamp/20 hs.) | white crystals | 100.1 |

The results described above reveal that any change in the property and any decrease in the remaining percent were not observed on the crystals of the present invention, thereby being stable.

In addition, the X-ray powder diffraction images of the crystals remained almost the same before and after their storage, thereby proving persistence of the crystal form of the crystals.

INDUSTRIAL APPLICABILITY

The amine compounds used in the present invention show a high effect increasing the contraction potency of the muscle of urinary bladder but no effect of contracting the muscle of urethra. They are, accordingly, useful as agents for improving excretory potency of the urinary bladder with high efficiency of urination. In addition, they are useful as prophylactic or therapeutic agents for dysuria, particularly for difficulty of urination.

CONCLUSION

The crystals of the present invention possess an excellent action to inhibit acetyleholine esterase and an action to improve the excretory potency of urinary bladder and are low in the toxicity, thereby being useful as drugs. Also, the crystals of the present invention are high in the purity, high in the quality, low in the hygroscopic property, and extremely excellent in the stability without being deteriorated upon a long-term storage under the usual conditions.

The entire specification and claims of parent U.S. application Ser. No. 09/787,288 and JIP 2001-85190 are incorporated by reference herein.

The invention claimed is:

1. A method for improving excretory potency of a urinary bladder which comprises administering a therapeutically effective amount of a compound represented by the formula:

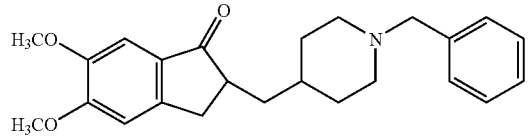

or a salt thereof to a patient in need thereof.

2. A method for treating dysuria which comprises administering a therapeutically effective amount of a compound represented by the formula:

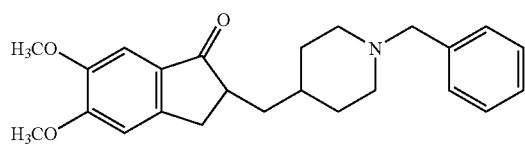
or a salt thereof to a patient in need thereof.
3. A method for treating difficulty of urination which comprises administering a therapeutically effective amount of a compound represented by the formula:
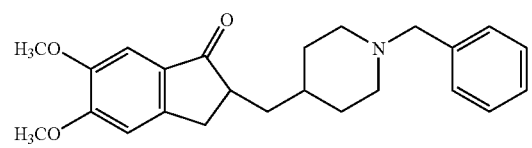
or a salt thereof to a patient in need thereof.